United States Patent
Tutunji et al.

(10) Patent No.: US 6,337,568 B1
(45) Date of Patent: Jan. 8, 2002

(54) SYSTEM AND METHOD FOR ENHANCED VERTICAL RESOLUTION MAGNETIC RESONANCE IMAGING LOGS

(76) Inventors: Tarek A. Tutunji, 15255 Gray Ridge #337, Houston, TX (US) 77082; Teruhiko Hagiwara, 9415 Bassoon Dr., Houston, TX (US) 77025; Peter Ian Day, 2015 Dryden Rd., Houston, TX (US) 77030

( * ) Notice: Subject to any disclaimer, the term of this patent is extended or adjusted under 35 U.S.C. 154(b) by 0 days.

(21) Appl. No.: 09/545,353

(22) Filed: Apr. 7, 2000

Related U.S. Application Data

(63) Continuation-in-part of application No. 09/425,926, filed on Oct. 25, 1999.

(51) Int. Cl.[7] ................................................. G01V 3/00
(52) U.S. Cl. ....................................... 324/303; 324/300
(58) Field of Search ................................ 324/303, 300; 250/256; 345/430; 382/156

(56) References Cited

U.S. PATENT DOCUMENTS

| | | | | |
|---|---|---|---|---|
| 5,675,147 A | * | 10/1997 | Ekstrom et al. | 250/256 |
| 5,689,581 A | * | 11/1997 | Nakao et al. | 382/156 |
| 6,011,557 A | * | 1/2000 | Keskes et al. | 345/430 |

OTHER PUBLICATIONS

Ekstrom et al, Formation ImagingWith Micro Electrical Scanning Arrays, The Log Analyst, vol. 28(3), pp. 294–206, 1987.*

* cited by examiner

Primary Examiner—Jay Patidar
Assistant Examiner—Brij B. Shrivastav

(57) ABSTRACT

An interpretation method and system for NMR echo-train data in thinly laminated sequences. The invention uses geological information obtained at higher vertical resolution, such as using Electric Micro Imaging, to enhance the vertical resolution of echo-train data, and thus avoids log interpretations in which the hydrocarbon potential of the formation can be misread because low resolution logs tend to provide an average description of the formation. Such averaging is especially problematic in thinly laminated sequences that consist of highly permeable and porous sand layers and less permeable silt or essentially impermeable shale layers. In a preferred embodiment, using the additional high-resolution formation information one can estimate the typical $T_2$-spectra of lithological laminae, and significantly enhance the permeability estimate in the laminated sequences. In another aspect the system and method of the preferred embodiment use neural network(s) to further enhance the resolution of a particular log measurement. The method and system are applicable to any temporal data from other logging tools, such as the thermal neutron decay log and others. The system and method enable proper evaluation of the high potential of thinly laminated formations, which may otherwise be overlooked as low permeable formations.

30 Claims, 44 Drawing Sheets

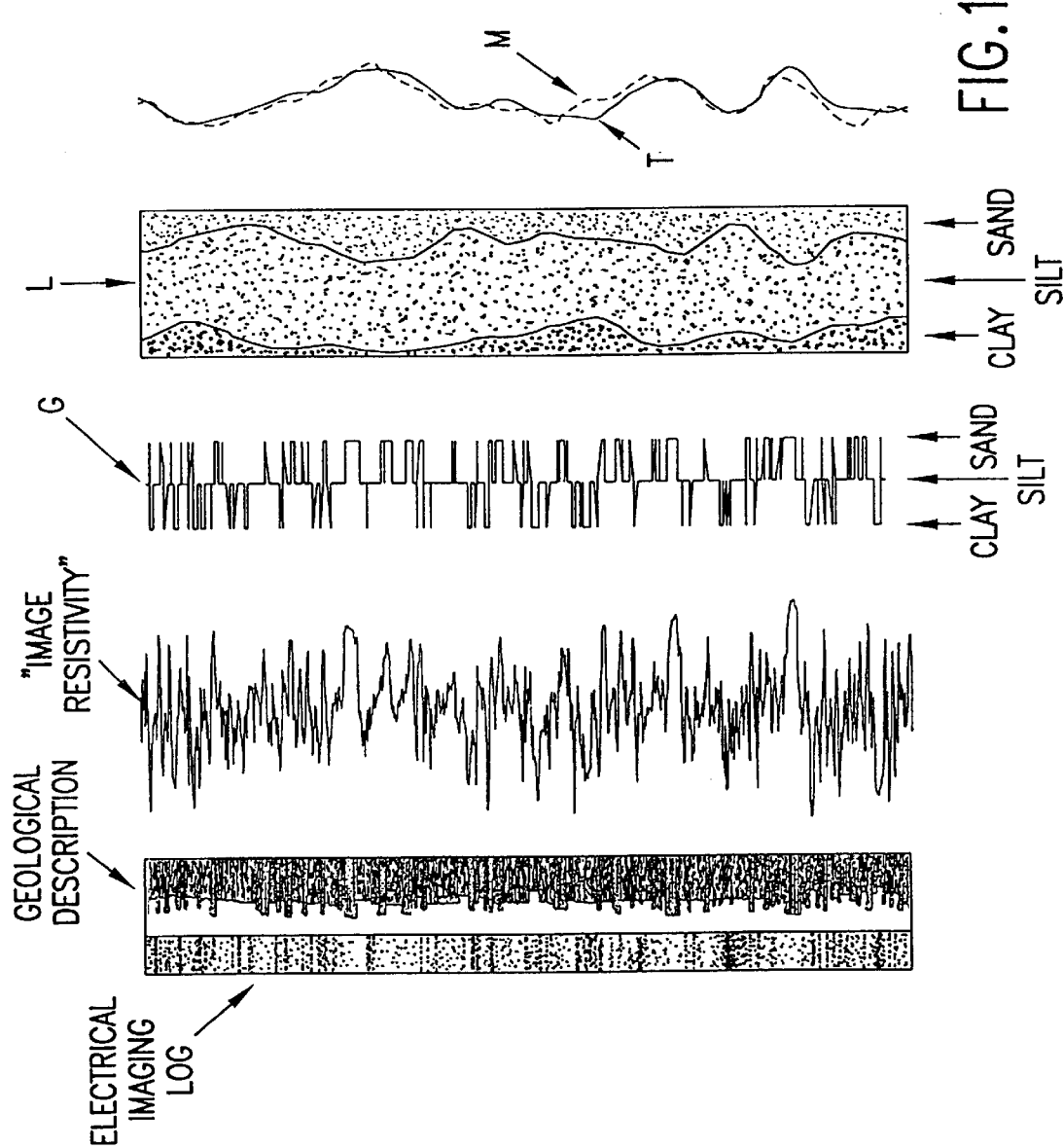

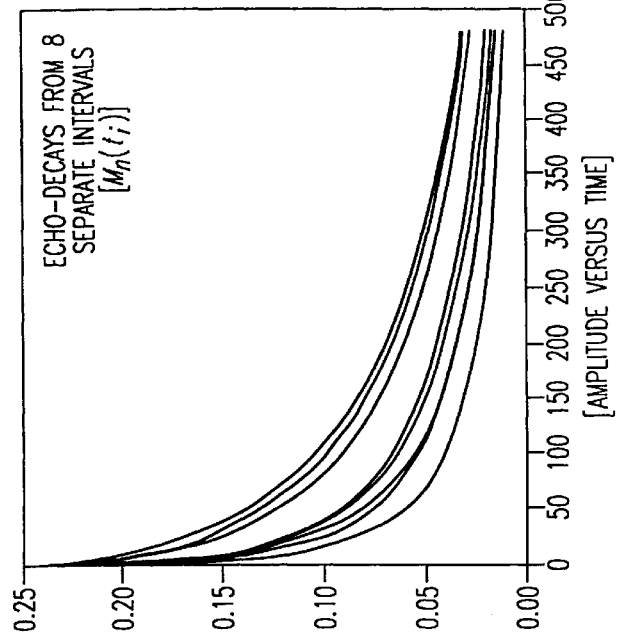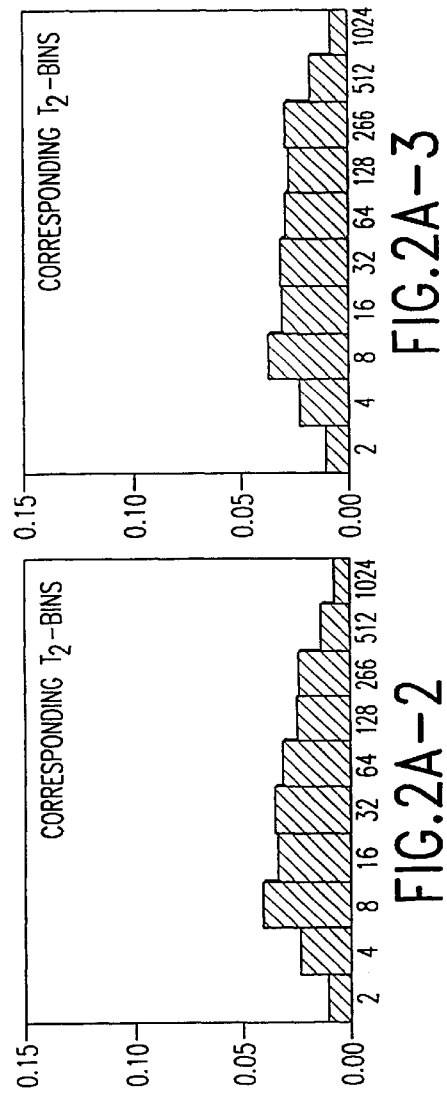

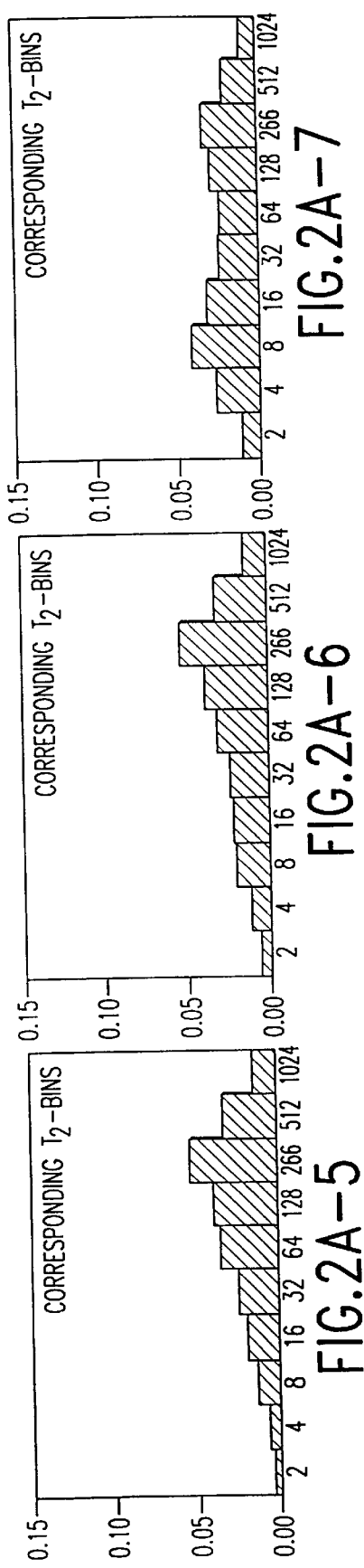
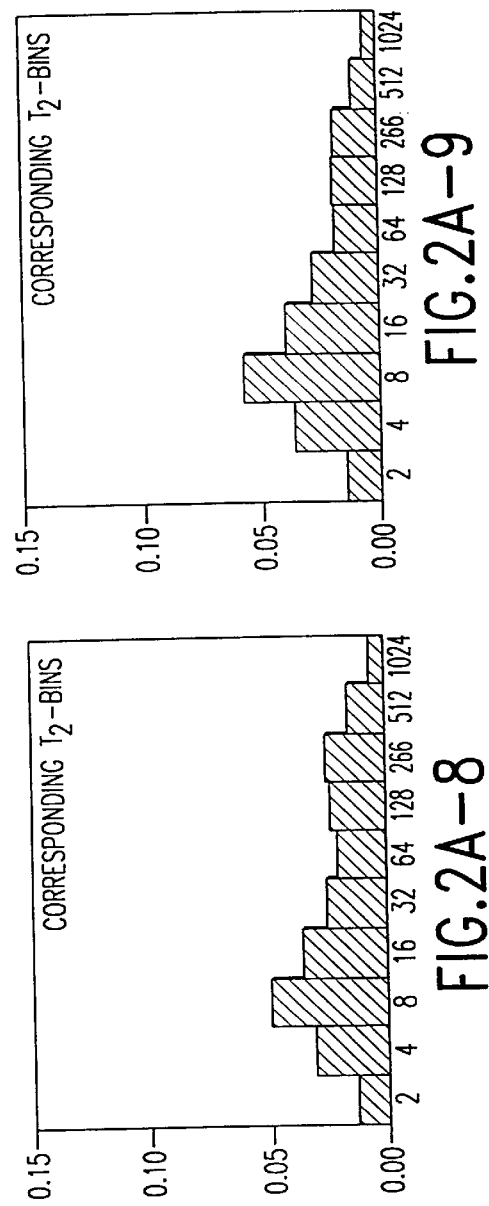
FIG.2A-5
FIG.2A-6
FIG.2A-7
FIG.2A-8
FIG.2A-9

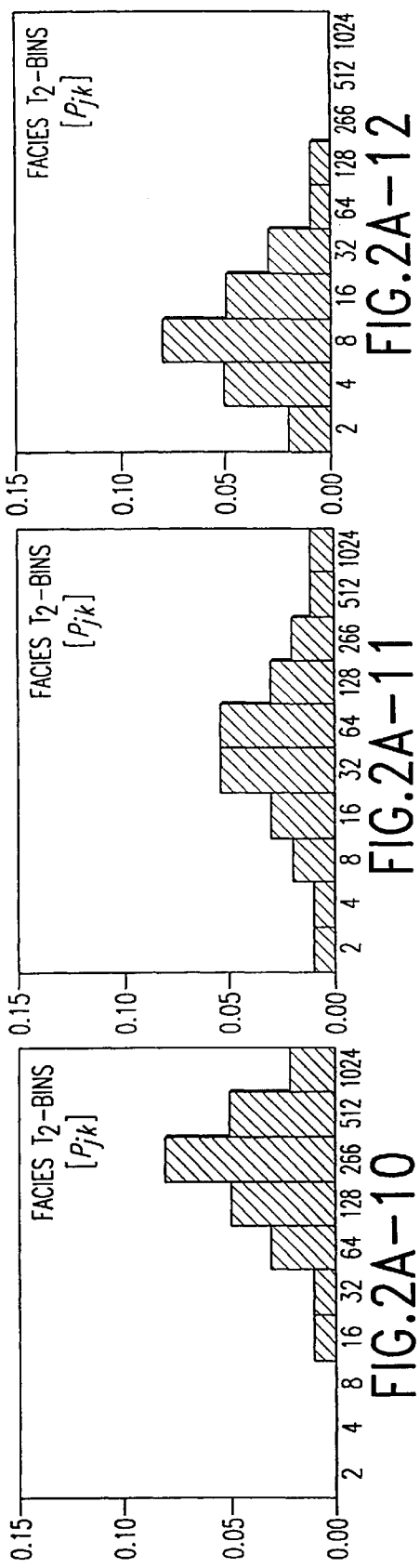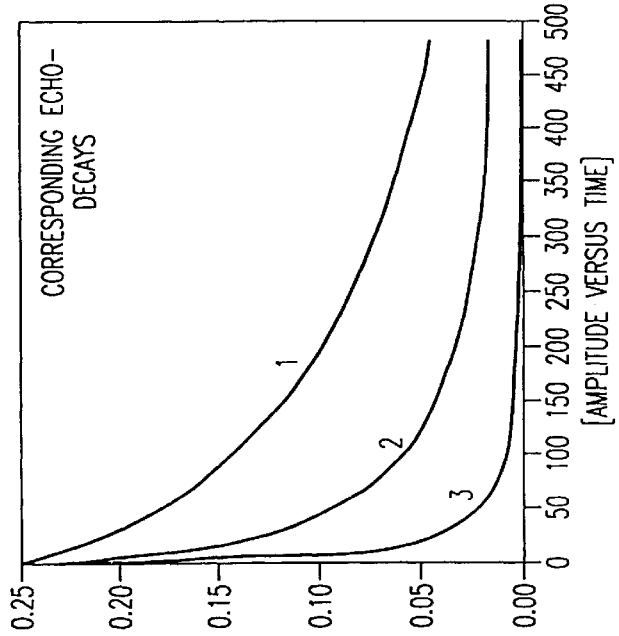

| $L_{nj}$ ECHO-DECAY | FACIES | | |
|---|---|---|---|
| | 1 | 2 | 3 |
| 1 | 0.2 | 0.4 | 0.4 |
| 2 | 0.3 | 0.3 | 0.4 |
| 3 | 0.5 | 0.3 | 0.2 |
| 4 | 0.6 | 0.3 | 0.1 |
| 5 | 0.6 | 0.2 | 0.2 |
| 6 | 0.4 | 0.1 | 0.5 |
| 7 | 0.3 | 0.1 | 0.6 |
| 8 | 0.2 | 0.1 | 0.7 |

FIG.2B

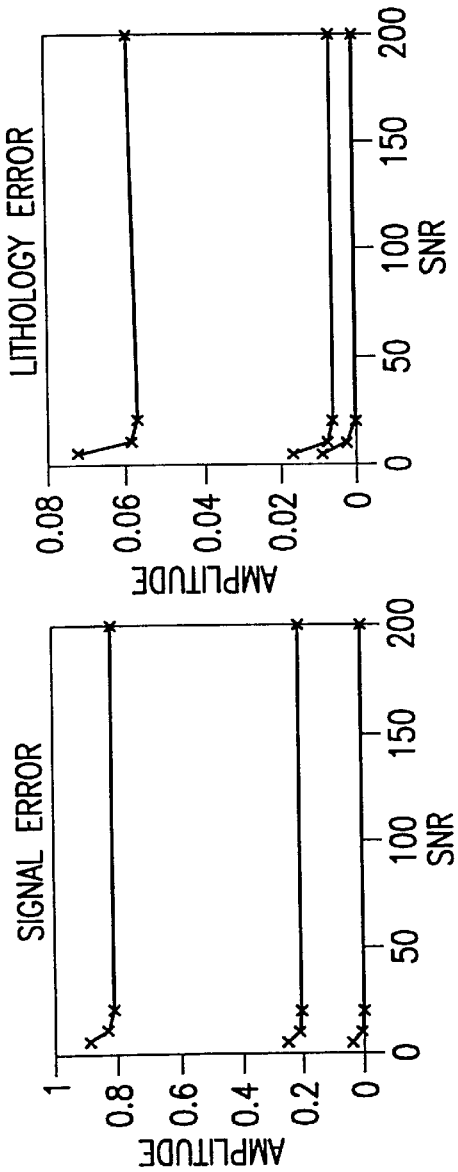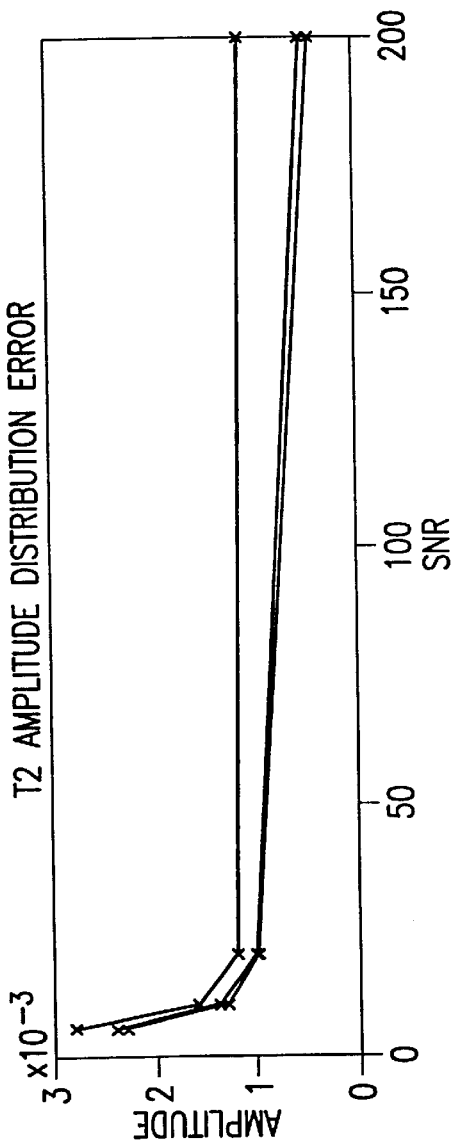
FIG.5A
FIG.5B
FIG.5C

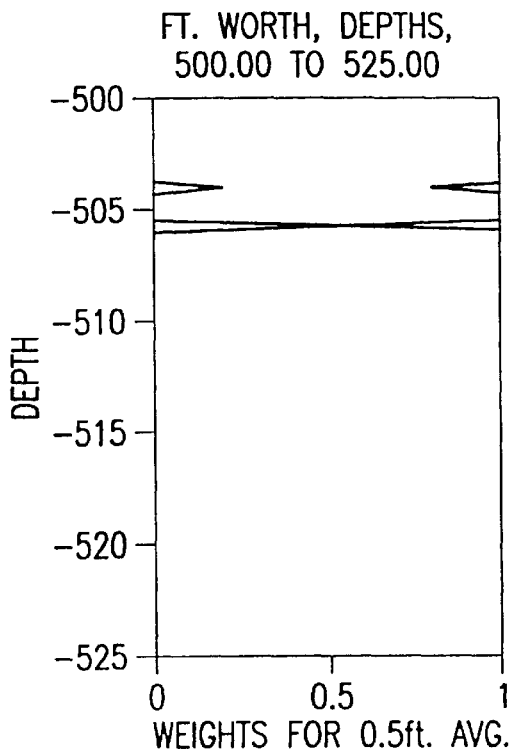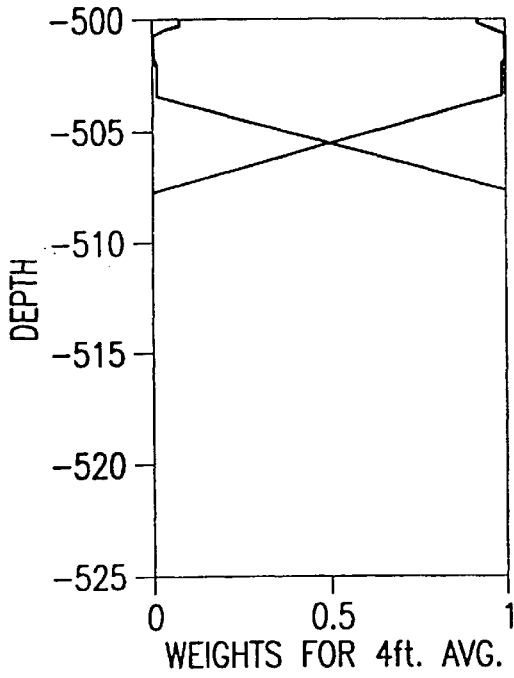
FIG.8E-1
FIG.8E-2
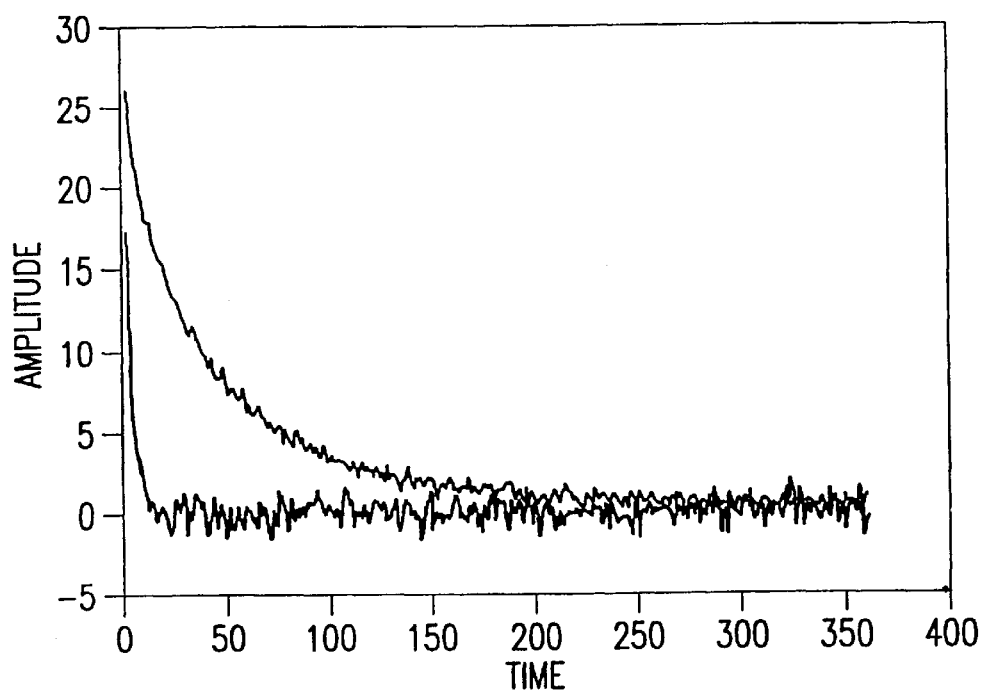
FIG.8F

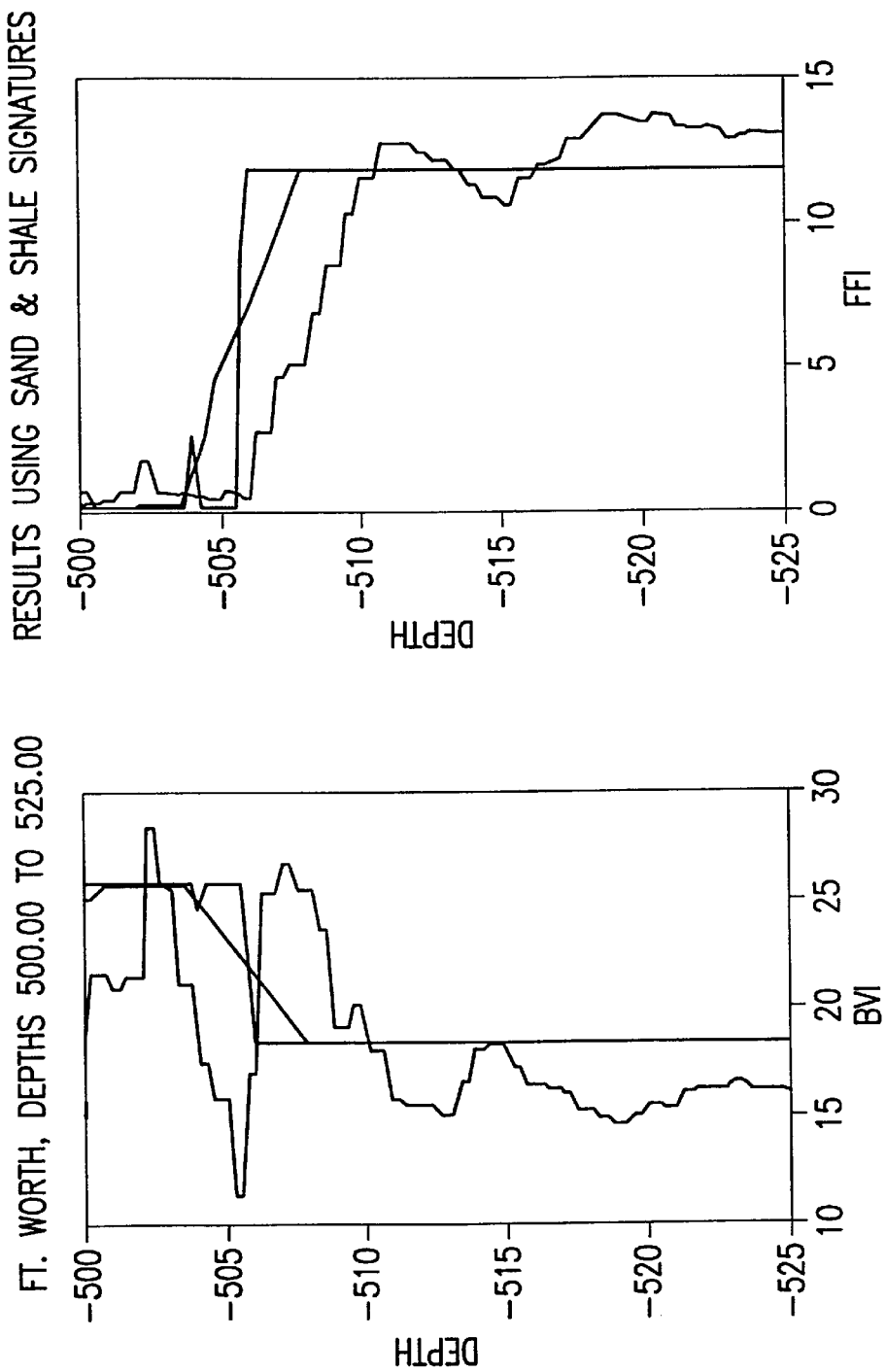

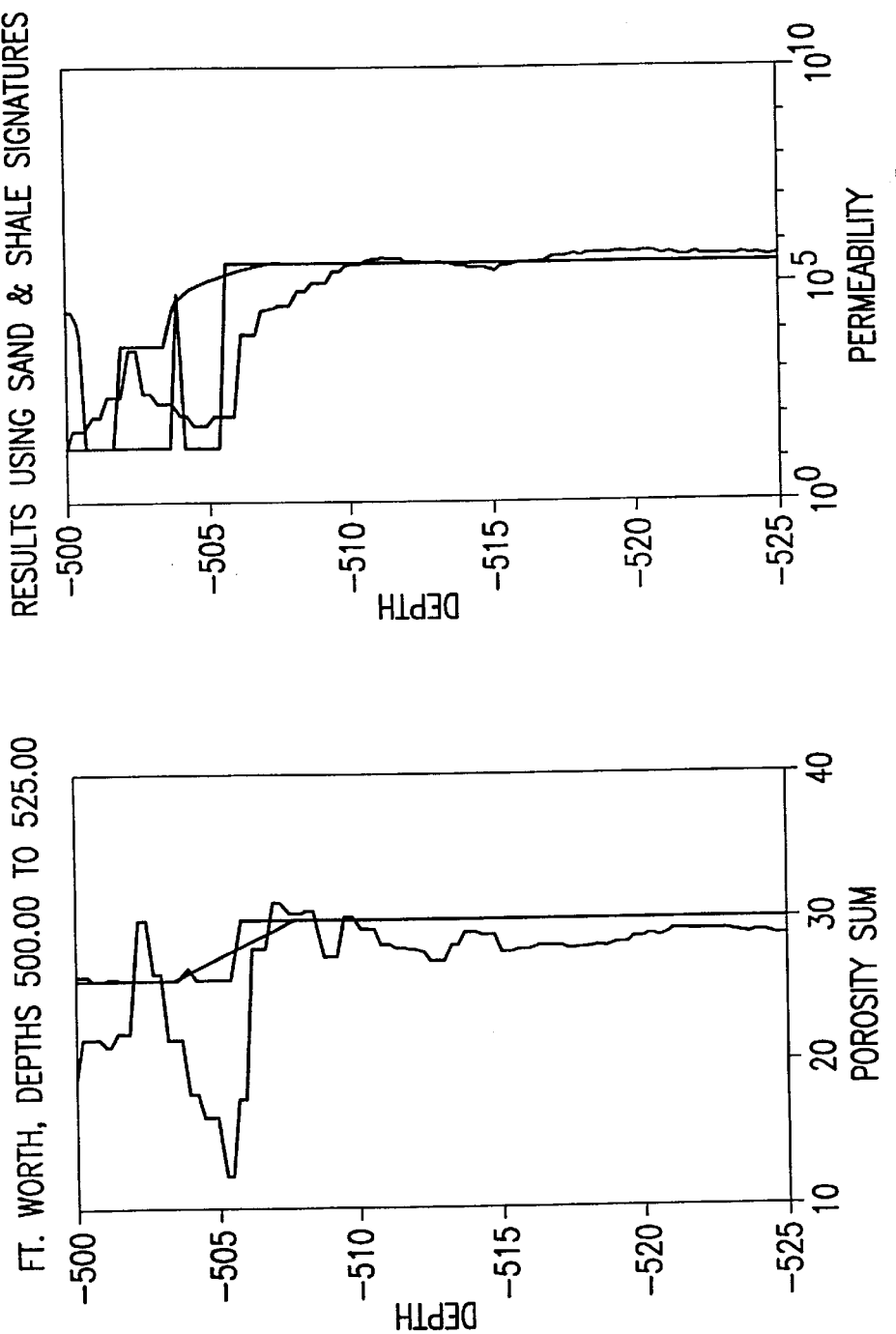

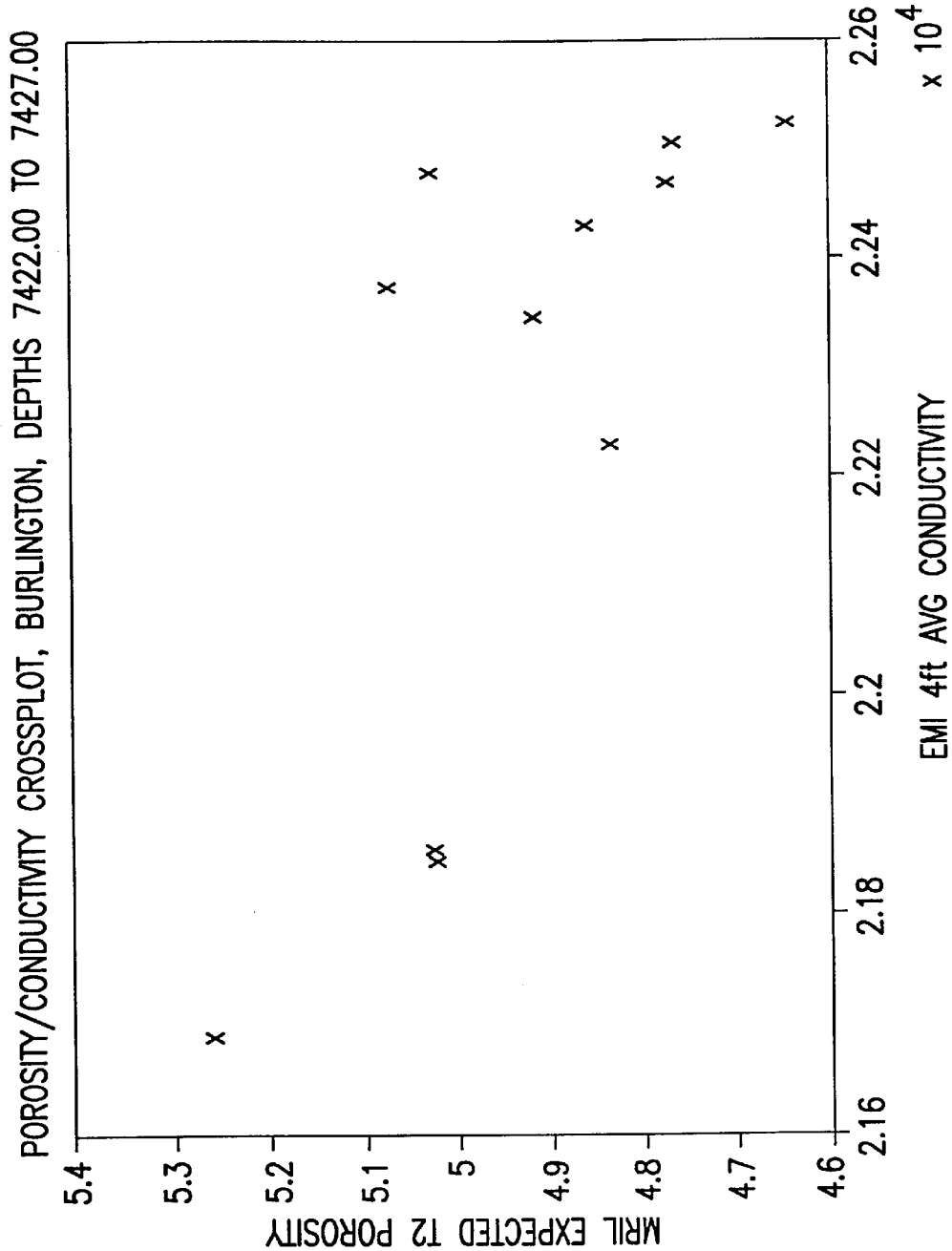

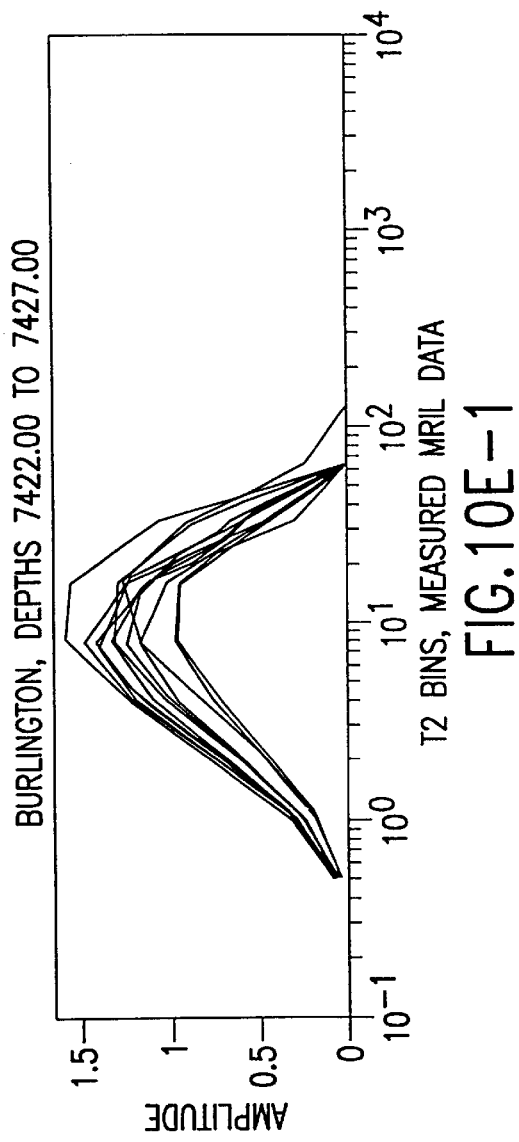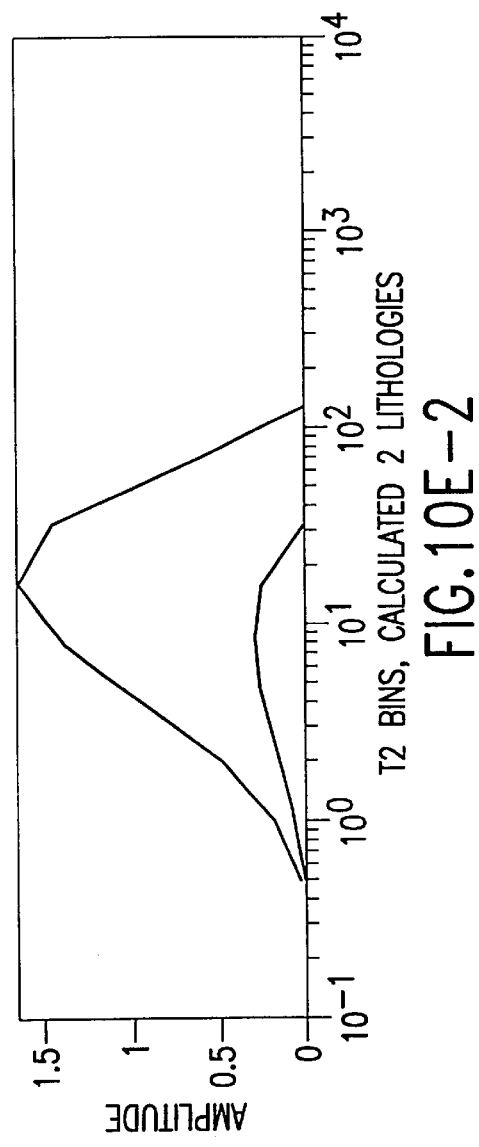
FIG.10E-1
FIG.10E-2

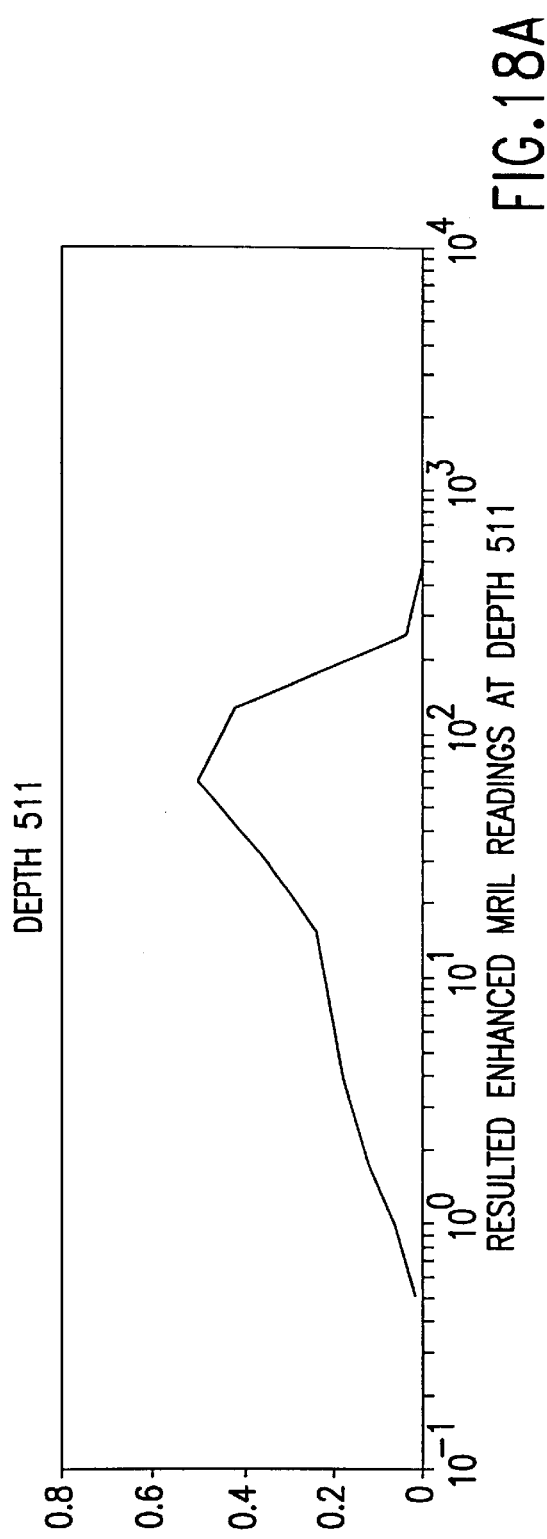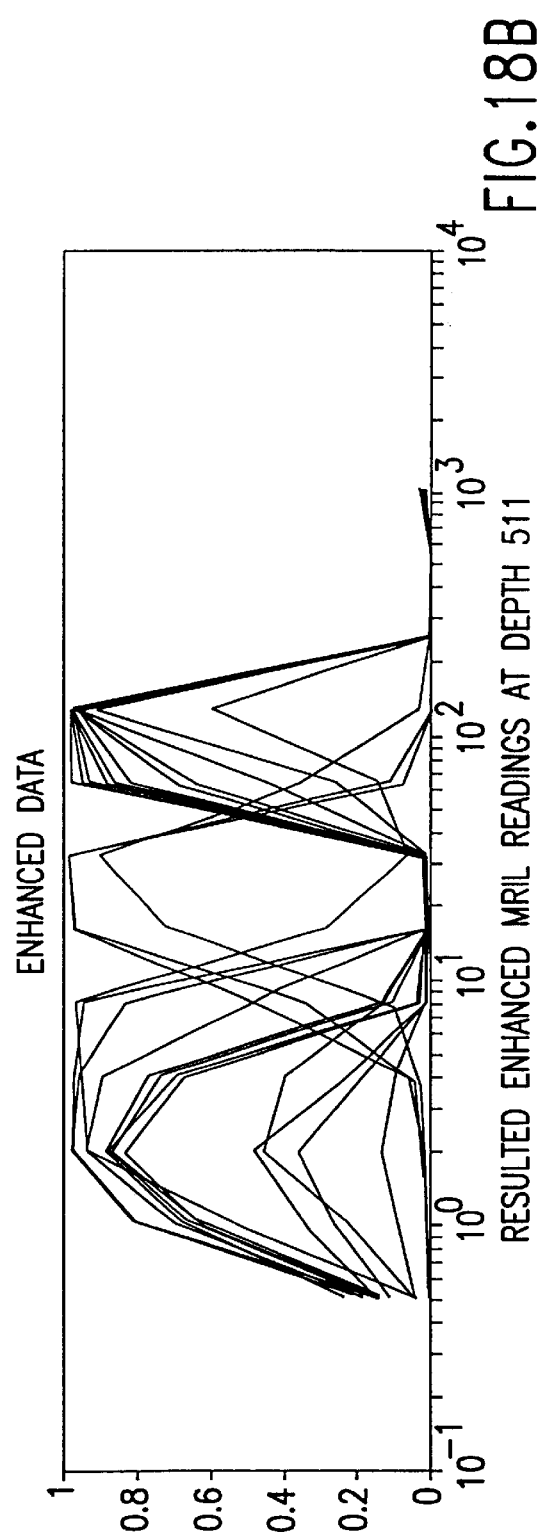

SYSTEM AND METHOD FOR ENHANCED VERTICAL RESOLUTION MAGNETIC RESONANCE IMAGING LOGS

This application is a C-I-P of Ser. No. 09/425,926 filed Oct. 25, 1999

FIELD OF THE INVENTION

This invention generally relates to borehole logging and logging-while-drilling (LWD), and in particular to a system and method for determining the properties of layered geological formations. A specific embodiment relates to a system and method for determining layer composition using a high-resolution log, and deriving associated high-resolution formation layer properties using time-dependent data, such as nuclear magnetic resonance (NMR) logs. In addition, or as an alternative, neural networks can be used to generate finer resolution data.

BACKGROUND OF THE INVENTION

In oil and gas exploration it is always desirable to understand the structure and properties of the geological formation surrounding a borehole, in order to determine if the formation contains hydrocarbon resources (oil and/or gas), to estimate the amount and producibility of hydrocarbon contained in the formation, and to evaluate the best options for completing the well in production. A significant aid in this evaluation is the use of wireline logging and/or logging-while-drilling (LWD) measurements of the formation surrounding the borehole (referred to collectively as "logs" or "log measurements"). Typically, one or more logging tools are lowered into the borehole and the tool readings or measurement logs are recorded as the tools traverse the borehole. These measurement logs are used to infer the desired formation properties.

In evaluating the hydrocarbon production potential of a subsurface formation, the formation is described in terms of a set of "petrophysical properties." Such properties may include: (1) the lithology or the rock type, e.g., amount of sand, shale, limestone, or more detailed mineralogical description, (2) the porosity or fraction of the rock that is void or pore space, (3) the fluid saturations or fractions of the pore space occupied by oil, water and gas, and others. Wireline logging tools do not directly measure petrophysical properties, they measure "log properties", for example, bulk density, electrical resistivity, acoustic velocity, or nuclear magnetic resonance (NMR) decay. Log properties are related to petrophysical properties via a set of mathematical or statistical relations, which are generally known in the art. In practice, frequently several different logging tools are combined and used simultaneously to obtain an integrated set of measurements. Thus, different tools may be used to obtain information about the same set of formation properties using different techniques, or different tools may be used to obtain information about different formation properties. Due to differences in physical measurement mechanisms and other factors, different logging tools have different volumes or zones of investigation, hence different measurement resolutions.

Subsurface formations are generally heterogeneous, so that porosity, saturation and lithology vary with position. A common example of heterogeneity is the presence in the formation of geological layers, or beds. Because logging tools have a nonzero volume of investigation, more than one layer may lie within the volume of investigation of a tool. In such cases, the petrophysical evaluation of one layer may be distorted by the presence of another layer falling within the larger volume of investigation of the tool.

The above phenomenon leads to a specific problem in the analysis of subsurface formations that include one or more underground layers, especially when the layers are thin compared with the vertical resolution of the measuring tool. Relatively thin layers (for example, less than about one foot) frequently come in groups of sometimes hundreds of layers, and have become subject to significant commercial interest because of their production potential. Any knowledge about the composition and properties of such layered formations that helps better estimate their production potential has thus become increasingly valuable.

As noted above, however, many of the standard wireline and LWD logs record data with a resolution along the borehole (generally this is the vertical resolution)—that is coarser than the geological layering of the formation. The effect of having low-resolution logs is that an interpretation of the data tends to be an average description of the formation that can seriously mislead the users of the interpretation. This "averaging" presents a particular problem in formations that contain a small fraction of thin, highly permeable and porous sand layers incorporated within a formation that consists predominantly of low permeability silts or essentially impermeable shales. In such formations the log properties that would reveal the sand layers are dominated, and thus masked, by the opposite log properties of the silts and shales. Accordingly, the averaging which is due to the low resolution of the measuring tool leads to underestimating of the production potential of the formation.

For example, many of the low resistivity and low contrast pay sands are known to be thinly laminated sand/silt or shale sequences. Most commercially available resistivity logging tools have coarse vertical resolution and fail to read resistivity of individual sand or shale layers. Instead, they read only the averaged horizontal resistivity that is low and dominated by the high conductivity of silt and shale layers, although individual sand layers can be highly resistive. As a result, the low resistivity of the layer sequence may be incorrectly interpreted as poor hydrocarbon potential of the formation.

Similar difficulty exists for NMR logging in thinly laminated formations. NMR logging tools have proved very useful in formation evaluation. Tools of this type include, for example, the centralized MRIL® tool made by NUMAR Corporation, a Halliburton company, and the sidewall CMR tool made by Schlumberger. The MRILL tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994. Certain details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200; 5,696,448; 5,936,405, 6,005,389 and 6,023,164. The structure and operation of the Schlumberger CMR tool is described, for example, in U.S. Pat. Nos. 4,939,648; 5,055,787 and 5,055,788 and further in "Novel NMR Apparatus for Investigating an External Sample," by Kleinberg, Sezginer and Griffin, J. Magn. Reson. 97, 466–485, 1992. The content of the above patents is hereby expressly incorporated by reference for all purposes, and all non-patent references are incorporated by reference for background.

Generally, although the NMR tools respond only to a very limited zone in the radial direction, their vertical resolution is not sharp enough to identify individual layers. The vertical resolution of the tools gets worse when NMR echo-trains are stacked over multiple events to improve the signal-to-noise ratio (SNR). Consequently, the echo-trains obtained from NMR logging reflect the average properties of the laminated sequences, so that the properties of non-productive silt or shale layers may mask those of productive sand layers.

One way to address the issue of layering identification is by visual inspection of cores, which inspection can identify the boundaries for different layers. Further, there are several logging tools that are capable of identifying the geological layering and classifying the various layer types. These are imaging tools, such as the Borehole Televiewer (BHTV), CAST, the Electric Micro Imaging (EMI) Tool, the Formation Micro Scanning (FMS) Tool, and others. Similarly, other fine resolution tools such as a dipmeter, high resolution Pe log, and high frequency dielectric log HFDT, may also be used to provide high-resolution layering information, when laminae are thicker than a few inches. It has been determined that the EMI tool, for example, is capable of identifing the geological layering and also, with some care, of classifying the various layer types.

Having available geological information from high vertical resolution logs, it is desirable to estimate sand properties out of the averaged measurements. In the case of echo-train data from a NMR logging tool, it is desirable to determine the echo-trains specific to particular lithological types, which can then be used to estimate the lithology-specific $T_2$-distribution for the formation layers. Using well-known mathematical transformations one can then obtain much more accurate permeability estimates for each lithology type, and thus obtain a realistic evaluation of the producibility potential of the formation. Such high-resolution estimates are very desirable, because otherwise the producibility potential of certain laminated formations, which may appear to have low permeability, may be overlooked.

PRIOR ART

Several attempts have been made in the prior art to address the issue of improving the vertical resolution of certain logs. With reference to FIG. 1, for example, if the formation can be classified into a number of discrete layer types, then a discrete log "G" can be created that describes the lithologic layering. In this particular case, an electric micro imaging (EMI) log of the geological formation is assumed, illustrated in the left-most track in FIG. 1. The geological description provided by the EMI log can be processed to obtain image resistivity (second track from the left), to which appropriate thresholds can be applied as to obtain the discrete log G. In the example illustrated in FIG. 1, the discrete log G corresponds to a three-component layering model, consisting of clay, silt and sand. Assuming next that each layer is assigned a property-value [P], mathematically one can create a high-resolution log that describes the true formation property, denoted in a vector notation as GxP. Next, if there is a logging tool that responds linearly to the formation properties, i.e., if the tool response can be modeled as a convolution filter [F], one can create a theoretical log [T] for this tool, given by the expression:

$$T = F \otimes (G \times P),$$

where $\otimes$ denotes the convolution operation. Since the process defined in the above expression is linear, it can be re-arranged as follows:

$$T = L \times P; \text{ where } L = F \otimes G,$$

in which the result of the convolution term L can be regarded as the lithology actually "seen", or "interrogated" by the logging tool, which is illustrated in the next-to-last track in FIG. 1.

Assuming that the properties of identically classified layers remain substantially constant over an interval of interest, it is possible to estimate property values $P_i$ for the layers by matching the theoretical log as closely as possible to a measured log [M], as illustrated in the last track in FIG. 1. In practice, this means solving for the properties vector P in the equation:

$$M = L \times P.$$

As seen in the last track in FIG. 1, the theoretical log T, matches quite closely the actual measurement log M over most of the interval of interest for the illustrated example. It should be noted that in practical applications for this process to work with accuracy, the formation interval being characterized must exhibit significant variations in the fractions of the lithologic-types seen by the log.

In accordance with the approach outlined above, the following method has been proposed by one of the co-inventors of this application for use in identifying log properties of the individual layer-types:

1. Classify the lithologies into lithology-types using a high-resolution (EMI-type) log;
2. Create a high-resolution lithology log [G] in which each depth is assigned membership to one lithology-type;
3. Create of a "convolution filter" [F] appropriate to the vertical resolution of the log whose layer-properties one wishes to determine;
4. Create of the log-specific lithology log [L] by convolving the high-resolution lithology-log with the log-specific convolution filter [L=F$\otimes$G]; and
5. Estimate the layer-properties [P] over an interval of interest from a best-fit match between the measured log data [M] and the theoretical log constructed from the filtered lithologies—e.g., by solving M=LxP to determine P.

In a least-square sense, the solution to the equation M=LxP can be found by determining the values of $P_j$ that minimize the error function:

$$\sum_{n=1}^{N} \left[ M_n - \sum_{j=1}^{J} \{L_{nj} \cdot P_j\} \right]^2$$

where $M_n$ is the value of the actual measurement at a specific depth in the logged interval (1,N), $L_{nj}$ is the fraction of the lithology-type seen at this depth, and $P_j$ is the property-value of this lithology-type. Refinements to this process can be made, such that the layer properties are allowed to vary within the larger interval in order to ensure a better match between the theoretical and the measured logs.

Once the values of the properties vector P have been determined, it is trivial to create a high-resolution version of the theoretical logged property, using the expression T=LxP. At the user's discretion, a log can be created at different resolution by applying a user-defined filter to T.

An alternative method employing an iterative method that minimizes the error between measured logs and predicted logs computed by a forward model is described in U.S. Pat. No. 5,675,147 to Ekstrom et al. The content of this patent is hereby incorporated by reference for all purposes.

While prior art methods, such as discussed above, address to some extent the issues associated with generating high-resolution petrophysical maps, they have a number of drawbacks, some of which are discussed below, and more specifically fail to exploit information available from time-dependent log sequences, such as NMR logs. In addition, the prior art fails to utilize the potential of certain processing techniques, such as the use of neural networks, to enhance the resolution of log data.

SUMMARY OF THE INVENTION

The above limitations of current formation evaluation techniques are addressed by the system and method of the present invention, which uses a set of measured wireline and/or LWD logs and, knowledge of the associated tool response models to estimate various properties of a geologic formation of interest. In the important case of a stack of thinly layered formations, the layer compositions and the formation properties inside each layer are estimated in a computationally efficient manner, using time-dependent logs. In one important aspect, the present invention is used to improve the vertical resolution of time-dependent logs, such a NMR logs.

In particular, according to this invention a system and method are proposed for the interpretation of NMR echo-train data. Because of the improved vertical resolution, the method is especially suitable for the formation evaluation of thinly laminated sequences. To this end, geological information is obtained at a high vertical resolution, which is then used to enhance the vertical resolution of the echo-train data. In a preferred embodiment, an Electric Micro Imaging (EMI) tool can be used to provide such information, although various different approaches can be used in alternative embodiments. In accordance with the invention, the high-resolution geological information is used to provide a model of the a time-dependent log data, such as a NMR log of the formation, and is compared with an actual measurement log in order to estimate lithology-specific data representations, such as the typical $T_2$-spectra of each lithological laminae. The lithology-specific data representations are then used to obtain petrophysical parameters of the formation, including enhanced permeability estimates in the laminated sequences. The method of this invention is applicable to any temporal data (i.e., time-varying data associated with a particular logging depth) from other logging tools, such as the thermal neutron decay log, and others.

In particular, in one aspect the present invention is a method for determining petrophysical properties of layered geologic formations, comprising: classifying layers in a portion of a geologic formation into two or more discrete layer types; providing numerical data about layer compositions in said portion of the formation using one or more log measurements; inputting provided numerical data to a neural network trained to detect patterns of classified layers; and enhancing the resolution of at least one log measurement using the output of the trained neural network.

In specific embodiments, the method is applied to discrete layer types, which may comprise sand and shale layer types. Generally, the step of providing information about layer compositions is performed using a high-resolution tool, such as an Electric Micro Imaging (EMI) Tool.

In a preferred embodiment, the petrophysical properties of layers that are determined using the method are in the group including but not limited to: permeability, bulk volume irreducible (BVI) and free fluid index (FFI).

In another aspect, the invention is a geological formation interpretation system comprising a system for interpretation of geological formations, comprising a specially programmed computer having: a first memory for storing one or more actual time-dependent measurement logs of a geological formation; a second memory for storing at least one measurement model based on a formation description, said formation description comprising two or more layer compositions; a neural network trainable to recognize patterns of layer compositions; a processor for generating enhanced lithology-specific measurement log data representations corresponding to said two or more geological layer types from an actual time-dependent measurement log of a geological formation processed using the neural network; and a display for communicating to a user the enhanced lithology-specific measurement log data representations.

BRIEF DESCRIPTION OF THE DRAWINGS

FIGS. 5A, 5B and 5C illustrate signal (FIG. 5A), lithology (FIG. 5B) and $T_2$ distribution (FIG. 5C) errors for the simulated NMR signals illustrated in FIGS. 3 and 4

FIGS. 16–19 illustrate the application of the neural network resolution enhancement approach in accordance with the present invention in field examples;

DETAILED DESCRIPTION OF THE PREFERRED EMBODIMENTS

Figure 8A:
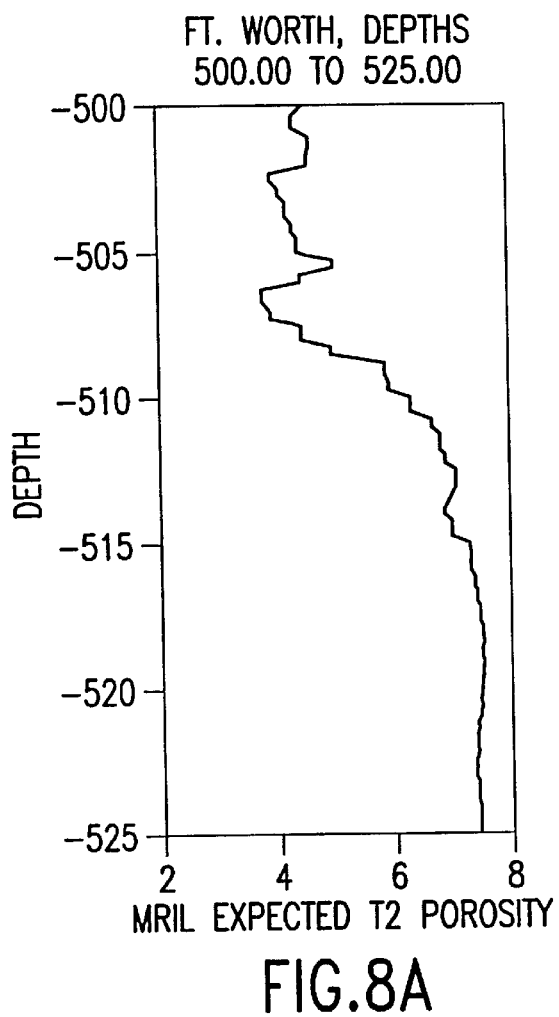
FIGS. 8(A–K), 9(A–C) and 10(A–J) illustrate the application of the method in accordance with the present invention in field examples.
Figure 8B:
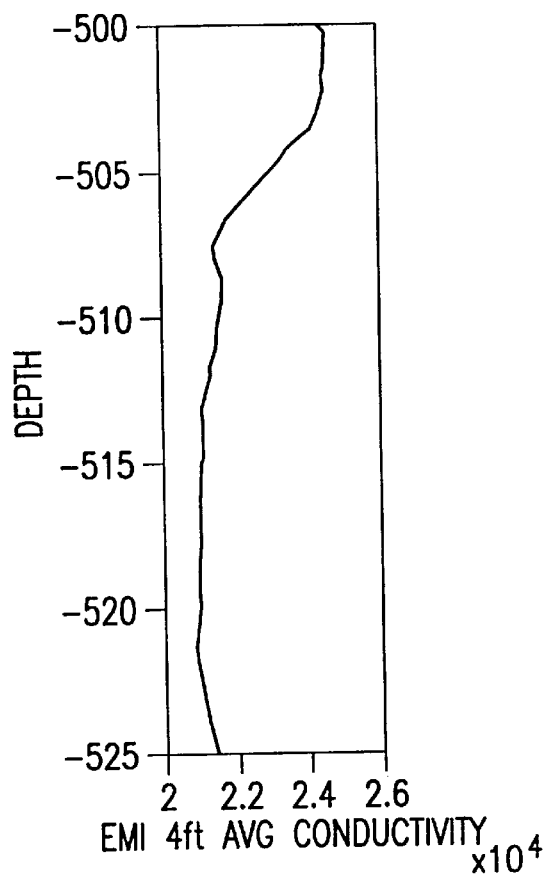
Figure 8C:
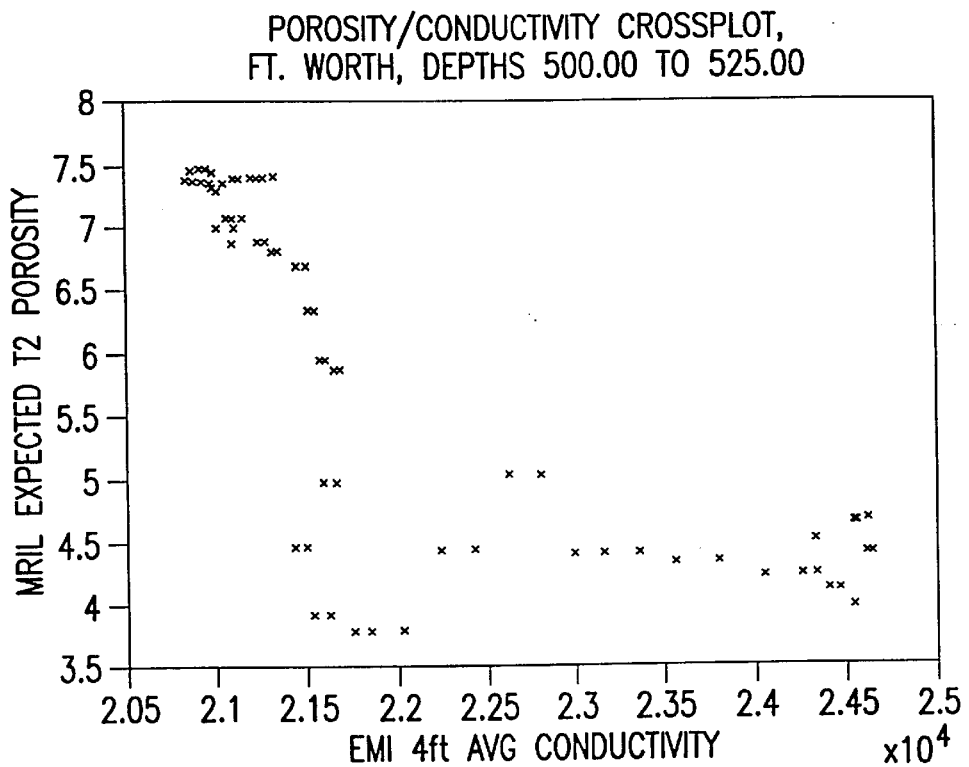
Figure 8D:
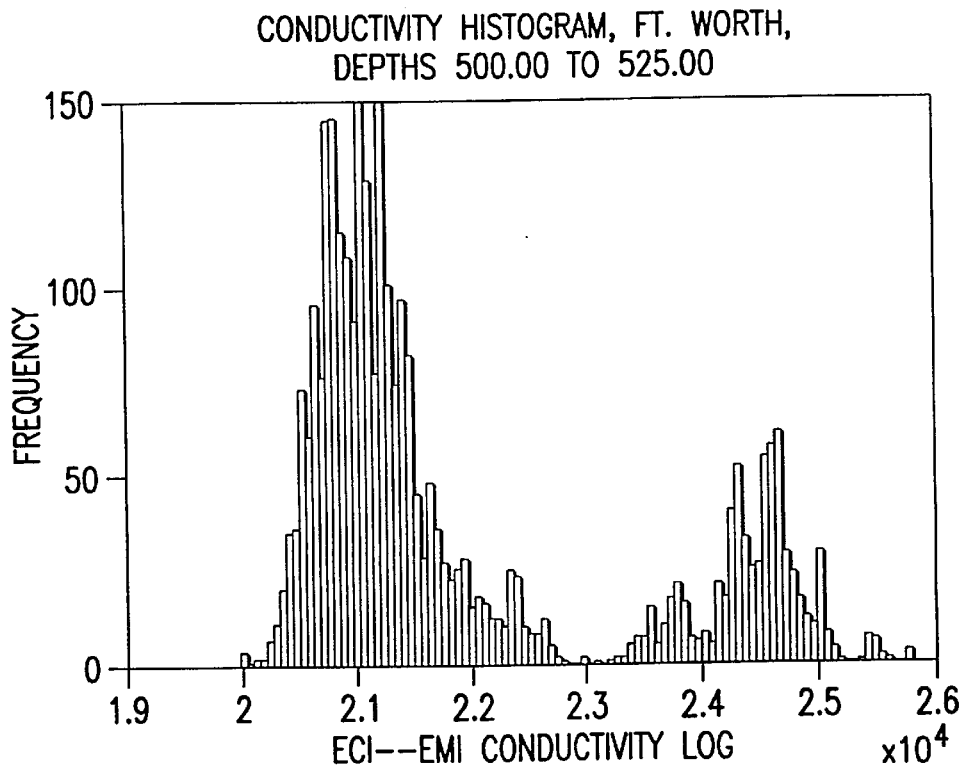
Figures 1, 8G:
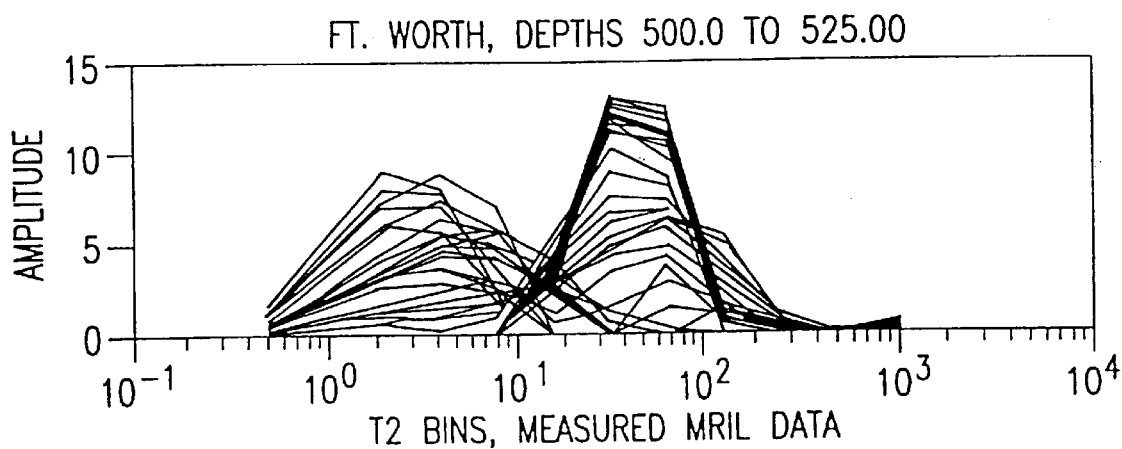
FIG. 1 is an example of a method for creating a high-resolution log describing the properties of a formation comprising three discrete layer types, when single-valued data, such as a resistivity log is used.

Prior art approaches to creating high-resolution versions of certain logged properties in layered formations, as illustrated in FIG. 1, work reasonably well for logs that have a single value at any given depth in the wellbore. However, there are several log types that record multiple values at a given depth. For example, as discussed in the background of this disclosure, nuclear-spectroscopy logs record an energy-dependent spectrum; acoustic-waveform logs record a time-dependent waveform; Nuclear Magnetic Resonance (NMR) logs record a time-dependent signal-decay.

In a preferred embodiment, this invention addresses the specific problem of how to extend high-resolution lithology property determination to multi-valued signal decay of the type provided by NMR logging tools. However, it should be understood that the process could be generalized to handle any multi-valued data gathering mechanism, such as the ones mentioned above.

Considering next for purposes of illustration NMR log data, as known in the art, it is recorded as a time-dependent signal decay, which corresponds to the relaxation properties of the formation. The raw measurement data generally cannot be interpreted directly, and must therefore be transformed into a representation that is meaningful for the analyst, i.e., in which the sought-after information is explicit. In particular, it is known in the art that the NMR time-dependent signal decay, which reflects the relaxation properties of the formation materials can be modeled as a multi-exponential process. It is now standard to extract from the raw measurement data amplitude and relaxation-time pairs that comprise the signal-decay. Thus, a theoretical signal-decay, T(t), can be described by:

$$T(t) = \sum_{k=1}^{K} P_k \cdot e^{-t/T_{2k}}$$

where $P_k$ is the amplitude of the component with a relaxation-time $T_{2k}$. In practice, the $T_{2k}$ relaxation-times are assumed, a priori, to lie in an exponential sequence—e.g., 1, 2, 4, 8, 16, 32, 64, 128, 256 . . . —and only the amplitudes associated with each "$T_2$-bin" are calculated. 30 Various ways of computing and interpreting the $T_2$ spectrum associated with NMR relaxation data are known in the art. In a preferred embodiment, one can use the MAP algorithm disclosed in U.S. Pat. No. 5,517,115, the content of which is incorporated herein by reference for all purposes, or refer to Prammer, M.G.: "NMR Pore Size Distributions and Permeability at the Well Site," paper SPE 28368 presented at the 1994 SPE Annual Technical Conference and Exhibition, New Orleans, September 25–28, which publication is incorporated herein for background.

In accordance with this invention, since the amplitude in each $T_2$-bin can be assumed to be an independent variable, the $T_2$-bin process NMR data could be treated as if it were multiple single-valued logs obtained from materials having different relaxation properties. In a specific embodiment, one can thus approach the problem of characterizing NMR decay signals as follows:

1. Create the log-specific lithology log for the particular NMR log;
2. Derive the $T_2$-bin amplitudes, $P_k$, for all the measured waveforms in an interval of interest;
3. Determine the characteristic $T_2$-bin amplitude for each lithology-type by separately treating each $T_2$-bin amplitude as a single-valued log.

It should be apparent that in general this approach will only work if the $T_2$-bin amplitudes behave linearly. In other words, if the derived $T_2$-bin amplitudes for a formation composed of multiple layer-types is simply the weighted-sum of the $T_2$-bin amplitudes for each layer-type. Generally, however, the process is only linear if the measured signal decays are essentially noise-free. Therefore, since the echo decays measured using NMR logging tools have a relatively poor signal-to-noise ratio (SNR), the $T_2$-bin amplitudes do not combine linearly and, more specifically, separate bins will tend to merge into a single composite bin—a process known as "bin creep".

As a result of the non-linearity of the $T_2$-bin amplitudes, it is necessary that the measured data be processed at the level of the time-dependent signal-decay, where data is truly multi-valued.

In accordance with this invention, conceptually the steps in the process to handle multi-valued data are similar to those used to analyze single-value data. The difference is in the step of matching the measured and theoretical logs, since one now has to match measured and theoretical signal decays.

As stated earlier, the NMR time-dependent signal decay can be described by a multi-exponential form:

$$T(t) = \sum_{k=1}^{K} P_k \cdot e^{-t/T_{2k}}$$

If a formation actually comprises several lithology-types, each with a characteristic $P_k$ distribution, then the theoretical signal-decay should be simply a composite of the signal-decays in each individual layer-type, weighted according to the fraction of each lithology-type "seen" by the NMR tool. Mathematically, this is expressed as follows:

$$T(t) = L_j \cdot \sum_{k=1}^{K} P_{jk} \cdot e^{-t/T_{2k}}; \sum_{j=1}^{J} L_j = 1$$

where $P_{jk}$ is the $T_2$-bin amplitude for the $k^{th}$ bin of the $j^{th}$ lithology-type, $L_j$ is the fraction of the $j^{th}$ lithology "seen" by the measurement.

In practice, rather than being measured continuously, the signal-decays are recorded at discrete times $t_i$, and the above expression is modified as follows:

$$T(t_i) = L_j \cdot \sum_{k=1}^{K} P_{jk} \cdot e^{-t/T_{2k}}$$

Given a number of measured echo-decays over an interval of formation, the determination of the characteristic bin distributions for a number of different layers can be defined as the determination of the parameters $P_{jk}$ that best match the measured signal-decays to the theoretical time-dependent signal-decays determined from the separate multi-exponential decays. Mathematically, the problem can be formulated as determining the elements $P_{jk}$ that minimize the following error function:

$$\sum_{n=1}^{N}\sum_{i=1}^{I}\left[M_n(t_i)-\sum_{j=1}^{J}\left\{L_{nj}\cdot\sum_{k=1}^{K}P_{jk}\cdot e^{-t_i/T_{2k}}\right\}\right]^2$$

where $P_{jk}$ is the $T_2$-bin amplitude for the $k^{th}$ bin in the $j^{th}$ lithology-type; $T_{2k}$ is the relaxation time associated with the $k^{th}$ bin; $M_n(t_i)$ is the measured amplitude at time $t_i$ of the $n^{th}$ echo-decay; and $L_{nj}$ is the fraction of the $j^{th}$ layer causing the $n^{th}$ echo-decay. In this example, there are K $T_2$-bins, J discrete layers, I echoes in each time-dependant signal-decay, and N measured signal-decays.

In accordance with this invention different methods can be used for solving for the $P_{jk}$ elements. In principal, any one of the standard techniques described in the literature can be used. The interested reader is directed, for example, to "Numerical Recipes: The Art of Scientific Computing", Chapter 10, Cambridge University Press, 1986, the content of which is incorporated by reference. Several commercially available numerical packages, such as MATLAB, can also be applied. It should be apparent that additional constraints on the form of $P_{jk}$ can be applied to produce results consistent with $T_2$-bin estimation methods currently in use.

Figures 2, 8G:
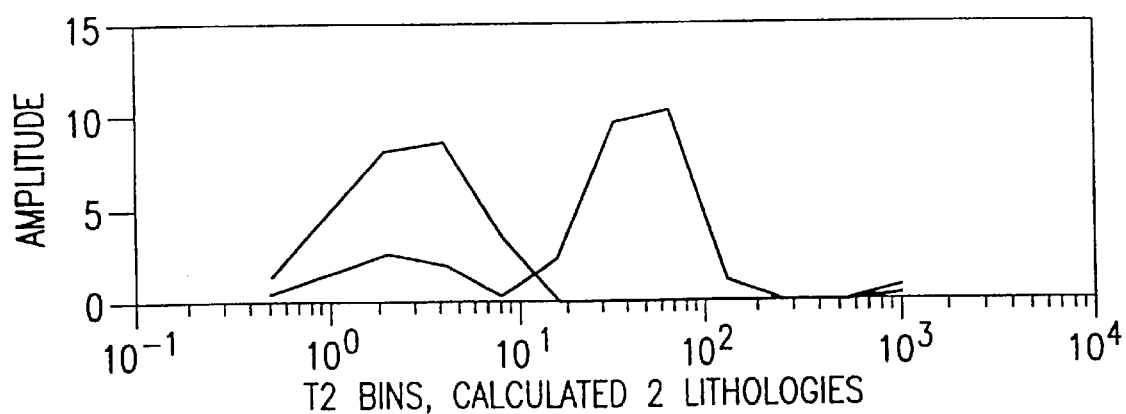
FIG. 2A illustrates conceptually the multi-valued process in accordance with the present invention, using ideal, i.e., no-noise echo-decays.
FIG. 2B is a table that shows the relative fractions ($L_{nj}$) of the three different layer types associated with each echo-decay, as illustrated in FIG. 2A.

FIG. 2A illustrates conceptually the multi-valued process of the present invention, using ideal (no-noise) echo-decays. In the left-hand side of FIG. 2A are shown eight echo-decays, next to which are illustrated the corresponding $T_2$-bins. FIG. 2B is a table that shows the relative fractions ($L_{nj}$) of the three different layer types associated with each echo-decay. The set of three $T_2$-bins, and the corresponding echo-decays, illustrated in FIG. 2A show the characteristics of the three facies types—with the $T_2$-bins being determined by minimizing the errors between the measured and theoretical waveforms.

In accordance with the present invention, once the $P_{jk}$ values have been determined, it is trivial for the user to generate a high-resolution log of either the theoretical waveforms or theoretical $T_2$-bin amplitudes. Naturally, as in the single-valued problem, the high-resolution theoretical displays can be filtered to any user-defined resolution.

ILLUSTRATIVE EMBODIMENTS

Following are several illustrative embodiments of using the method of this invention, which is referred to next as Geologically Enhanced Vertical Resolution (GEVR) method.

GEVR for Conductivity Data

The first illustration of the GEVR method of the present invention relates in fact to single-valued data, but is considered in some detail to introduce notations and to illustrate the conceptual continuity from a single-value to multi-value cases in accordance with the principles of the present invention. Consider for example an induction log data in a thinly laminated sand/shale sequence. When laminae are much thinner than the vertical resolution of an induction log, the tool registers a constant conductivity value $\sigma^{log}$. It is well known that induction logs read average laminae conductivity, which can be expressed mathematically as:

$$\sigma^{log}=\sum_i h_i\sigma_i \text{ where } \sum_i h_i=1$$

and $\sigma_i$ is the lamina conductivity of the i-th lithology, whose relative volumetric abundance is $h_i$. In the case of sand/shale (or any binary) sequences, only two lithological types, i.e., sand and shale, are considered. Accordingly, the above expression reduces to:

$$\sigma^{log}=h_{sand}\sigma_{sand}+h_{shale}\sigma_{shale}$$

$$h_{sand}+h_{sand}=1$$

For purposes of hydrocarbon exploration, of primary interest is the conductivity of the sand layers $\sigma_{sand}$. The volumetric abundance of the sand $h_{sand}$, a quantity referred to in the art as net-to-gross (N/G) ratio (which is the percentage of sand thickness in the formation) may be known either from core examination or from measurements using various logging tools. The N/G ratio is considered in further detail below. Using the above expression, if $\sigma_{shale}$ is known or can be estimated, then the desired quantity $\sigma_{sand}$ can be obtained from the above equation as follows:

$$\sigma_{sand}=\frac{\sigma^{log}-(1-h_{sand})\sigma_{shale}}{h_{sand}}$$

In the above expression it is assumed that $\sigma^{log}$ remains essentially constant and the entire sequence is regarded as one homogeneous formation described by one constant N/G ratio.

Suppose next that $\sigma^{log}$ varies significantly in such formations. If the conductivity for each lithological lamina remains relatively constant, the change of log conductivity in depth is attributed to the change in lamina abundance, i.e.:

$$\sigma^{log}(z)=\sum_i h_i(z)\sigma_i$$

$$\sum_i h_i(z)=1$$

The lithological weight $h_i(z)$ is a geological information that can be estimated from petrographical inspection of cores or from high-resolution image-logs, such as CAST and EMI. It can be also determined from high-resolution tools such as the Pe tool, HFDT dielectric log, and dip meter. Naturally, it is important to ensure that $h_i(z)$ is measured with the vertical resolution of the induction log.

If the lithological weight and hence the log conductivity change sufficiently over an interval, the lamina conductivity of each lithology $\sigma_i$ can be determined from the log by minimizing the error, $$S=\int dz\left|\sigma^{log}(z)-\sum_i h_i(z)\sigma_i\right|^2$$

In accordance with the present invention, the lamina conductivity for the i-th layer is determined by $$\sigma_i=\sum_k [A]_{ik}^{-1}B_k$$

where $[A]^{-1}$ denotes matrix inversion; the elements $[A]_{ik}$ of the matrix A are computed as follows:

$$[A]_{ik}=\int dz h_i(z)h_k(z)$$

and $$B_i=\int dz h_i(z)\sigma^{log}(z)$$

If the conductivity profile at a better vertical resolution is needed, it can be constructed from the lamina conductivity simply by, $$\tilde{\sigma}^{\log}(z) = \sum_i \tilde{h}_i(z)\sigma_i \quad \text{Eq. (5)}$$

$$\sum_i \tilde{h}_i(z) = 1$$

where $\tilde{h}_i(z)$ is the lithological weight calculated over the desired vertical resolution and can be generated from high-resolution data.

GEVR for MRIL Data

Following is an illustration of the method of this invention for multi-valued data corresponding to each depth mark. As noted above, some logging tools collect spectral data at each logging depth. For instance, Spectral Gamma Log samples gamma ray energy spectrum at each depth. Thermal Neutron Decay log measures time decay spectrum of thermal neutron population. Magnetic Resonance Imaging tool measures nuclear magnetic resonance (NMR) echo-trains, the temporal decay spectrum of polarized hydrogen nuclei. In accordance with the present invention substantially the same method of geological resolution enhancement may be applied to different multi-valued logging data.

Consider a laminated formation, where each lithological layer is characterized by its own echo train $M_i(t)$. In this case, in accordance with the principles discussed above, in a referred embodiment the echo train data $M^{log}(z;t)$ observed by the logging tool at a logging depth z is given by the expression:

$$M^{\log}(z;t) = \sum_i h_i(z)M_i(t) \quad \text{Eq. (1)}$$

In the above expression it is assumed that the lithology-specific echo train $M_i(t)$ remains substantially constant among the layers in the formation. Variations on the order of 10–20% or even higher can be tolerated for practical purposes. Then, in the same way as discussed above, the lithology-specific echo train can be determined using the expression:

$$M_i(t) = \sum_k [A]_{ik}^{-1} B_k(t) \quad \text{Eq. (2)}$$

where $$[A]_{ik} = \int dz h_i(z) h_k(z) \quad \text{Eq. (3)}$$

$$B_i(t) = \int dz h_i(z) M^{\log}(z;t) \quad \text{Eq. (4)}$$

It should be apparent that if the echo train at a better vertical resolution is needed to match to other logging data, it can be constructed from the lithology-specific echo trains using the expression $$\tilde{M}^{\log}(z;t) = \sum_i \tilde{h}_i(z)M_i(t) \quad \text{Eq. (5)}$$

where $\tilde{h}_i(z)$ is the lithological weight calculated over the matching vertical resolution.

In an alternative embodiment of the present invention, instead of time-domain echo train data, one case use the corresponding mapped $T_2$-distribution data. In this alternative embodiment, each lithological layer is characterized by its own $T_2$-distribution, designated $C_i(T_2)$. Then, the $T_2$-distribution data observed by the logging tool $C^{log}(z;T_2)$ at a logging depth z is given by $$C^{\log}(z;T_2) = \sum_i h_i(z)C_i(T_2) \quad \text{Eq. (6)}$$

Again, it is assumed that the lithology-specific $T_2$-distribution remains reasonably constant among the layers in the formation. Then, in the same way as discussed above, the lithology-specific $T_2$-distribution can be determined by, $$C_i(T_2) = \sum_k [A]_{ik}^{-1} D_k(T_2) \quad \text{Eq. (7)}$$

where $$[A]_{ik} = \int dz h_i(z) h_k(z) \quad \text{Eq. (8)}$$

and $$D_i(T_2) = \int dz h_i(z) C^{\log}(z;T_2) \quad \text{Eq. (9)}$$

As before, if the $T_2$-distribution data at a still better vertical resolution is needed to match to other logging data, it can be constructed from the lithology-specific $T_2$-distributions using the expression:

$$\tilde{C}^{\log}(z;t) = \sum_i \tilde{h}_i(z)C_i(t) \quad \text{Eq. (10)}$$

where $\tilde{h}_i(z)$ is the lithological weight calculated over the matching vertical resolution.

In accordance with another aspect of this invention, instead of considering the entire $T_2$-distribution in Eq. (6) above, some specific but relatively small number of quantities derived from the $T_2$-distribution (or the original echo-train data) may be used. For instance, the following bulk volume irreducible (BVI) and free fluid index (FFI) relations can be used in alternate embodiments of the present invention to estimate lithology-specific BVI and FFI:

$$BVI^{\log}(z) = \sum_i h_i(z)BVI_i \quad \text{Eq. (11)}$$

$$FFI^{\log}(z) = \sum_i h_i(z)FFI_i \quad \text{Eq. (12)}$$

In this case, similarly to Eq. (6), lithology-specific BVI and FFI can be estimated.

In accordance with the present invention it is preferable to use time-domain echo data, because in alternative embodiments the original echo-train data has to be mapped (or inverted) to $T_2$-distributions, in which process some information is lost, resulting in reduced processing accuracy.

Figure 6:
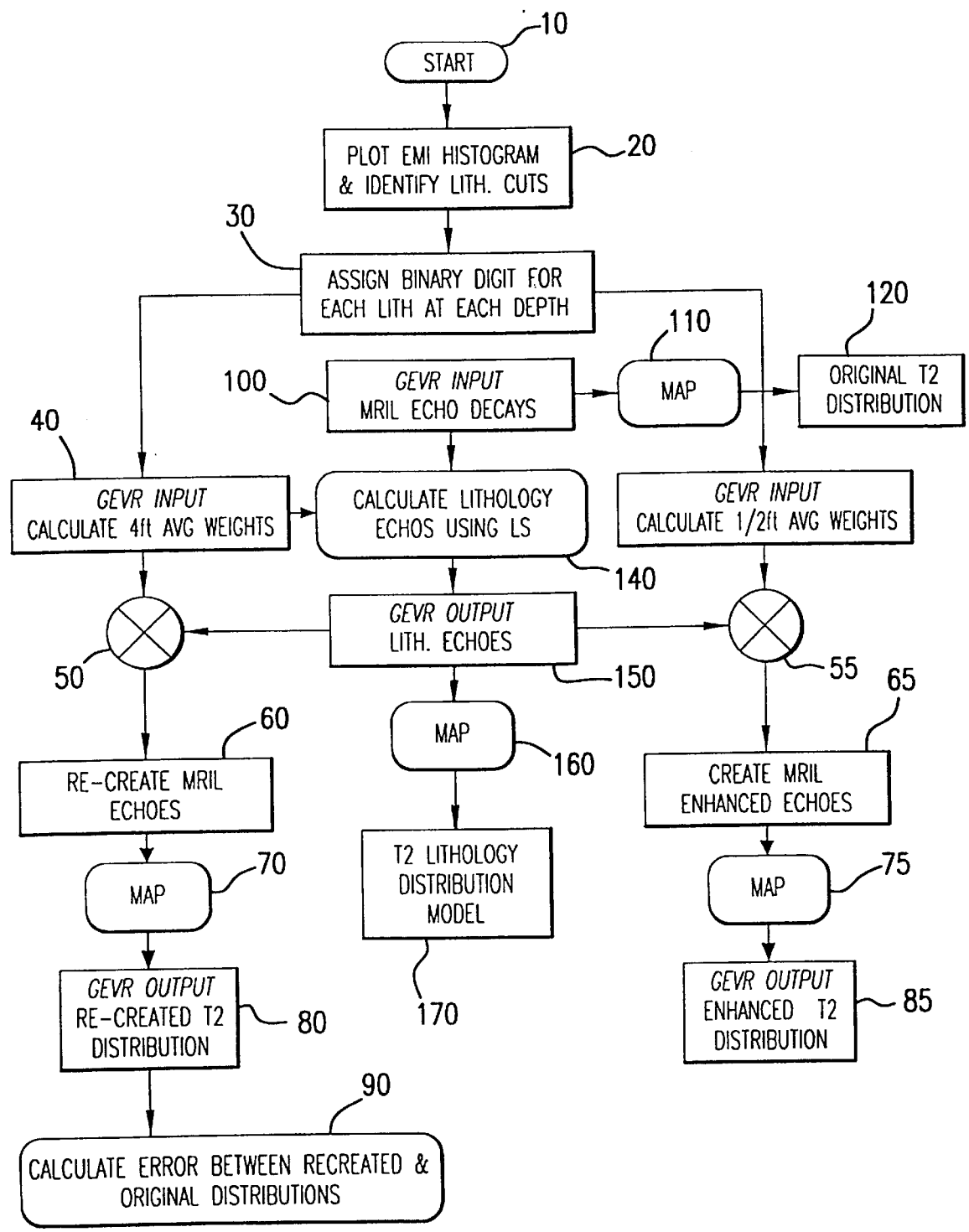
FIG. 6 is a flow diagram of the method used in accordance with a preferred embodiment of the present invention.

The processing algorithm used in a preferred embodiment of the present invention is illustrated in FIG. 6. Processing starts at step 10. The GEVR method used in accordance with this invention is initiated using two types of data. The first type of data can be designated broadly as the GEVR weight input data, and is obtained, in a preferred embodiment, in processing steps 20, 30 and 40. In particular, at step 20 in a specific embodiment a high-resolution log data, such as one obtained from a EMI tool is used to provide accurate layer composition. In a specific embodiment, illustrated also in FIG. 7A, at this processing step is determined a histogram (for example a conductivity histogram) in which individual layers identified by the high-resolution tool are assigned to two or more layer classes. FIG. 7A shows an example in which only two layer classes are used. In the following step 30, in a specific embodiment, class assignment is made by assigning a binary digit for each lithology at each depth. Once all lithology class assignments are made, in the following step 40 (or 45 in the parallel processing branch directed to different-resolution data), is computed the GEVR weight input for a given resolution, which in this embodiment is illustrated as a computation over a four-foot interval. Further, for the two-layer composition illustrated in the figure, the calculated weight is the net-to-gross (N/G) ratio. For example, in a particular case of two lithology classes of which one is sand, the N/G ratio is simply the percentage of sand thickness over the length of the formation.

The other input to the GEVR processing algorithm in accordance with the present invention is a time-dependent sequence. In a preferred embodiment illustrated at step 100 in FIG. 6, this GEVR input is a NMR echo train sequence (raw data). As shown in FIG. 6, at step 110 a standard mapping is applied from the time domain to the $T_2$ spectrum domain using well known algorithms such as MAP, which is described in detail, for example, in U.S. Pat. No. 5,517,115, the content of which is incorporated by reference for all purposes. The application of the MAP processing algorithm results, at step 120, in the original $T_2$ distribution of the input sequence.

As illustrated at steps 140, 150, both the NMR echo decay data and the GEVR weight data are processed using Eqs. (1)–(5) above to calculate lithology-specific echo trains $M_i(t)$, which are then separately subjected to MAP processing in step 160 to obtain lithology-specific $T_2$ spectrum distributions in step 170. Not illustrated in FIG. 6, in the final step of the method various petrophysical properties, such as permeability, are estimated from the lithology-specific echo and/or $T_2$-spectrum information. For instance, in practical applications discussed below, the permeability estimate is shown to be significantly enhanced in the laminated sequences.

As illustrated in processing block 50, in a specific embodiment the GEVR input weights are combined with the GEVR lithology-specific echos to re-create, in step 60, theoretical echos (corresponding to the originally measured NMR echo data). In step 70 these echo sequences are passed through a mapping to obtain a theoretical GEVR output re-created $T_2$ distribution, which is then compared at step 90 with the original distribution (computed in step 120) to estimate the error between the recreated and the original distributions. In a specific embodiment, the error between the re-created and measured $T_2$ distributions (as indicated in the flow chart) is used as a confidence criteria of the model used. Ideally, (the averaged over four feet) recreated $T_2$ spectrum should match the original MRIL $T_2$ spectrum reading. A comparison of the measured and the calculated lithologies in accordance with the method of this invention is illustrated in FIG. 7B, and shows very close match between the actual (measured) values and those computed using the method of this invention. In a specific embodiment, an error measure providing a quantitative expression of how well the model fits the measurement can also be provided.

In a specific embodiment, a least square error measure can be used with satisfactory results, although recursive algorithms can also be used in alternate embodiments. In accordance with another specific embodiment, if the computed error is above certain threshold, some of the model parameters can be changed, such as the size of the processed measurements and/or the lithology cut, to obtain better agreement between theoretical and actual measurement data. The right-hand side in FIG. 6 illustrates another processing branch of the method, in which a different resolution, i.e., selected over a half-foot interval can be used.

Model Example

To examine how the above-illustrated GEVR processing algorithm works, a simulated model-formation consisting of three distinct lithology types, labeled a, b and c was considered. Assuming different values for the lithological weights, a synthetic echo-train data was generated for the model formation. Applying the abGEVR algorithm in accordance with this invention allowed to retrieve three echo-trains and three $T_2$-distributions from the synthetic echo-train data, assuming that the litho-weight values were known, as illustrated below.

A. Input Lithology Model and Synthetic Echo-train Log

Figure 3A:
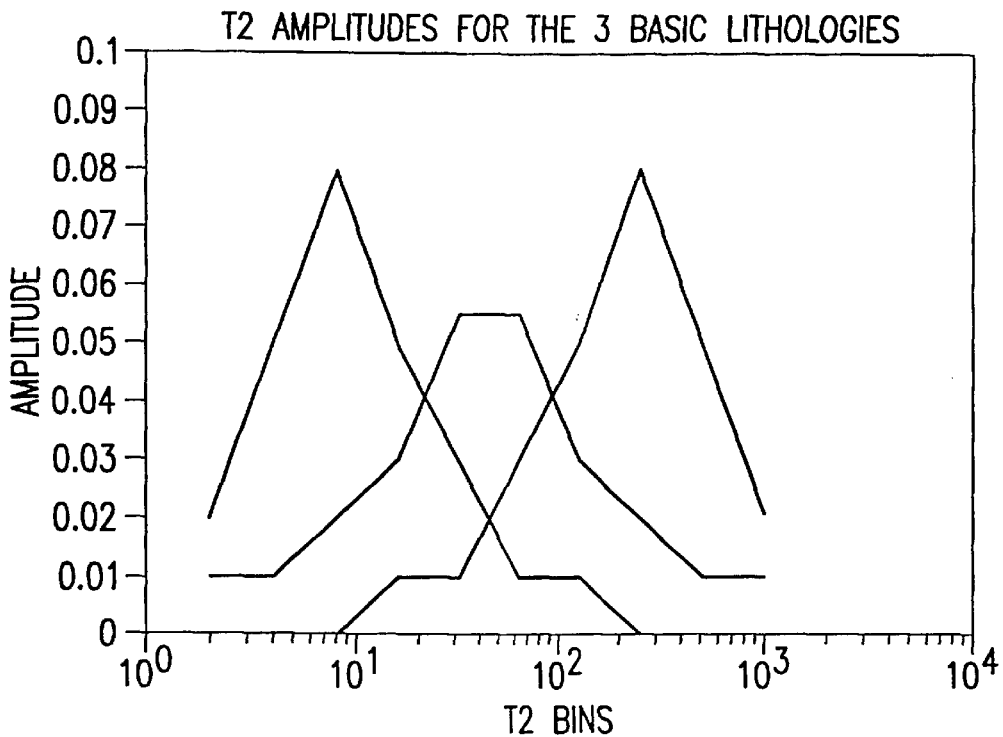
FIGS. 3A, 3B, 3C and 3D illustrate an input lithology model and synthetic echo-train log generated in accordance with the present invention.
Figure 3B:
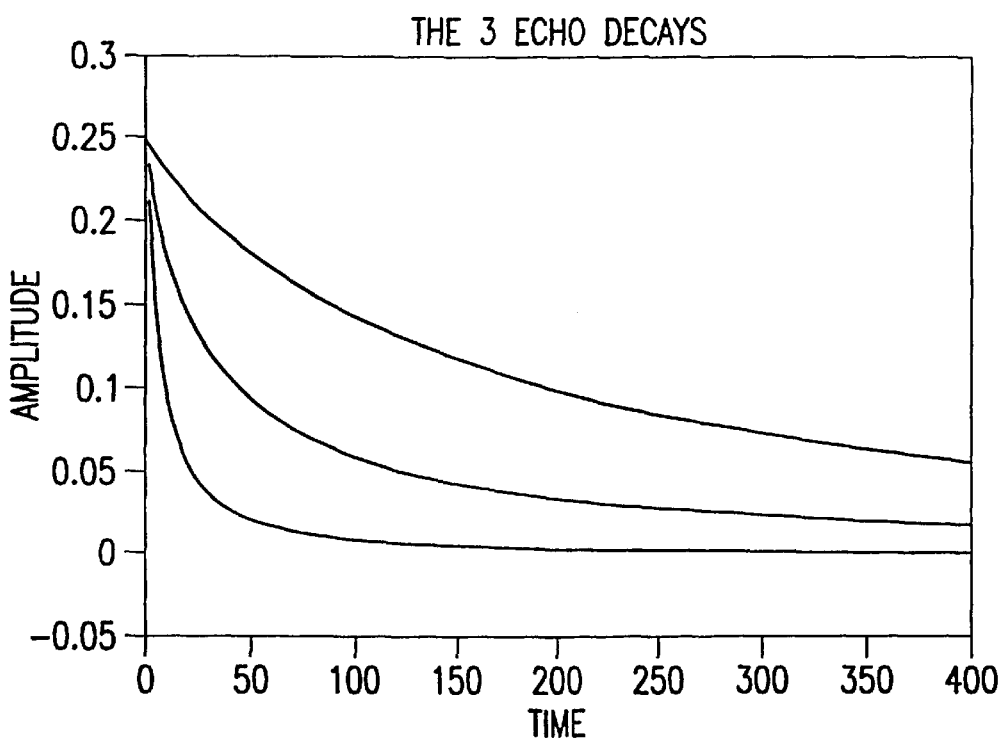

With reference to FIGS. 3A, 3B, 3C and 3D, suppose the existence of three lithology types, denoted for convenience $\sigma_i$=a, b, and c. Each lithology type has a different $T_2$-bin distribution, $C_i(T_2)$, as shown in FIG. 3A, and corresponding lithology-echo, $$M_i(t) = \sum_{T_2} C_i(T_2) e^{-t/T_2} \qquad \text{Eq. (13)}$$

for $\sigma_i$=a, b and c, as shown in FIG. 3B, where it is assumed that each lithology-type has the identical porosity of 25%.

Figure 3C:
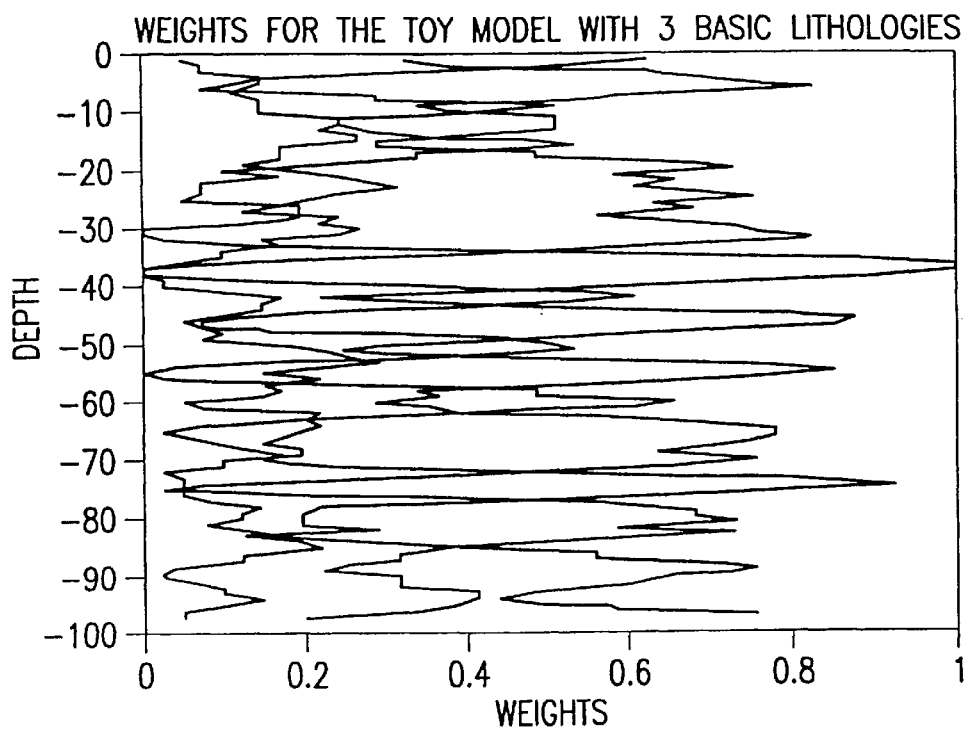
Figure 3D:
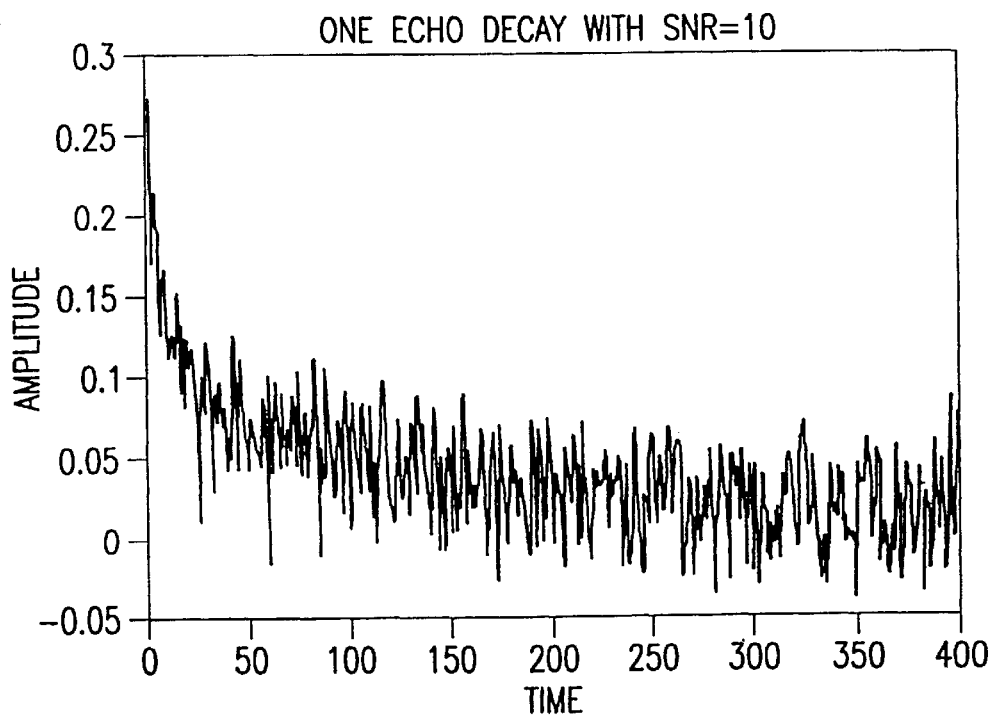

FIG. 3C shows simulated lithology-weight functions for $h_i(z)$ ($\sigma_i$=a, b and c) used for 97 logging depths. In this example, a simulated echo-train log was generated using the expression $$M^{\log}(z; t) = \sum_i h_i(z) M_i(t) + \varepsilon(z; t) \qquad \text{Eq. (14)}$$

where $\varepsilon(z;t)$ is random noise added to the signal. FIG. 3D illustrates one such echo train.

B. GEVR Processing

Figure 4A:
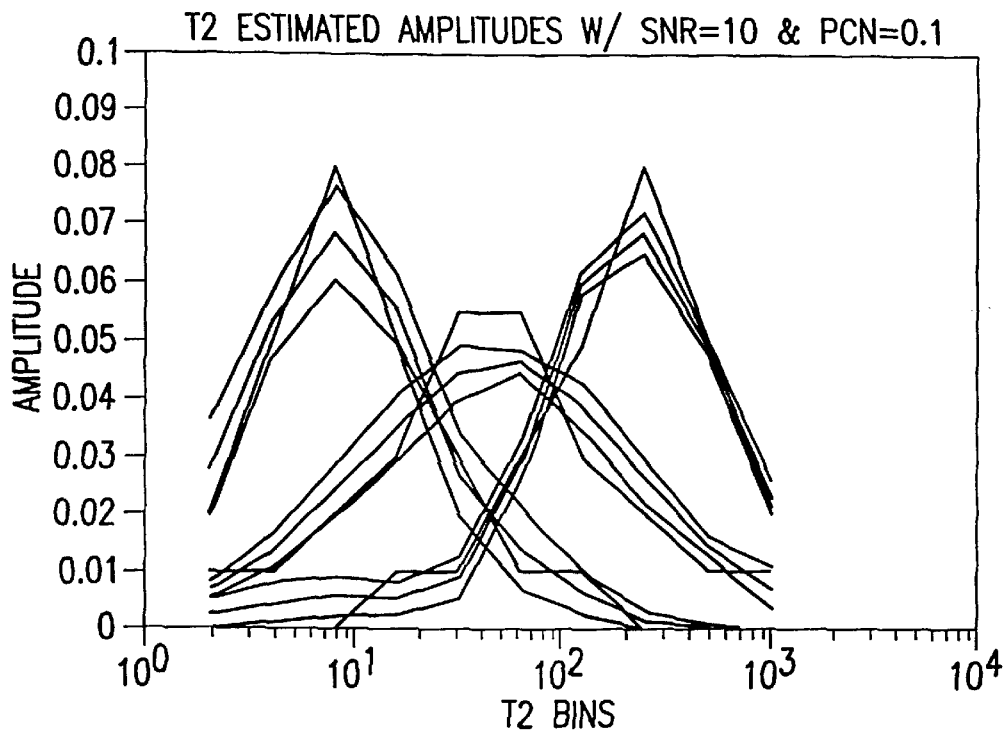
FIGS. 4A, 4B, 4C and 4D illustrate, for the simulated NMR log data and a three-layer type formation illustrated in FIGS. 3A, B, C and D, the average of the inverted $T_2$-distribution from 100 random noise realizations (FIGS. 4A, 4B and 4C) and estimated three-lithology echos with a SNR=10, where the model distributions are denoted with crossed lines.
Figure 4B:
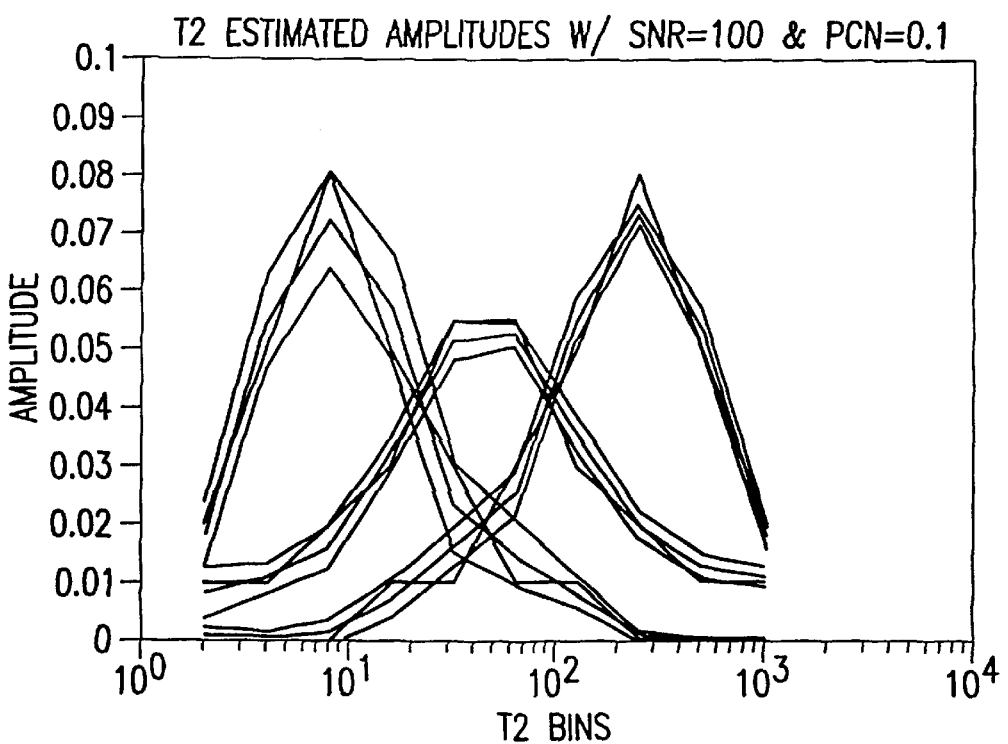
Figure 4C:
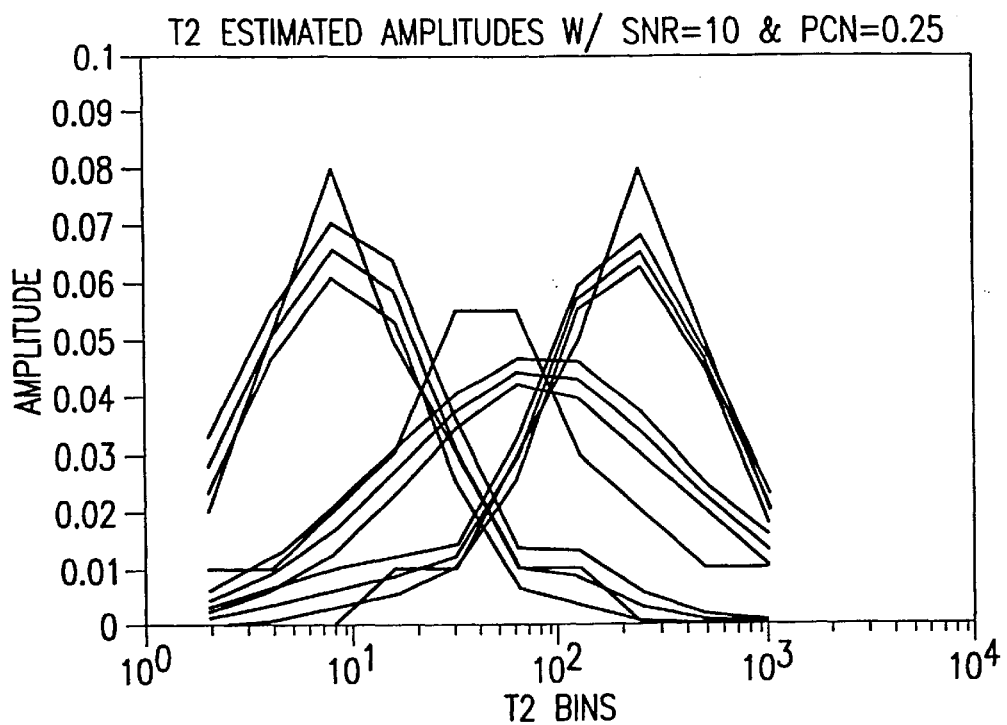
Figure 4D:
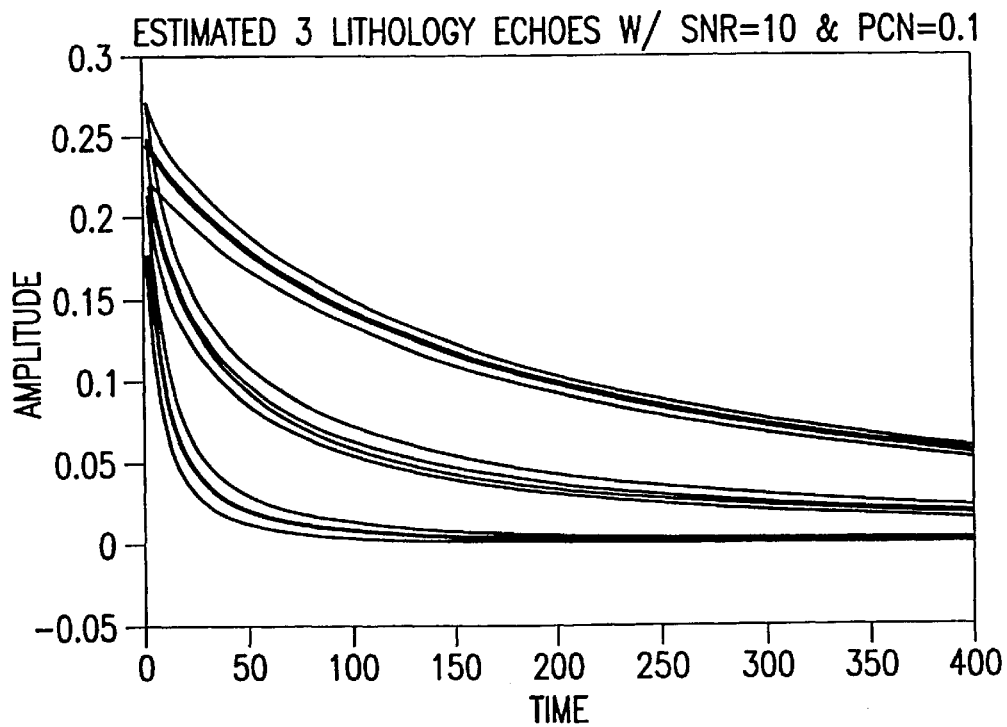

In a preferred embodiment, the lithology-weights are estimated using a fine-resolution logging tool, such as EMI and Pe, which is subject to errors. In the following example, the synthetic echo-train data was processed using the GEVR method of the present invention, assuming the lithology-weight is expressed as follows:

$$\tilde{h}_i(z) = h_i(z) + \delta_i \qquad \text{Eq. (15)}$$

where $\delta_i$ is the error in estimation of the litho-weight for the i-th lithology type. The resulting lithology-echo $\tilde{M}_i(t)$ was then compared to the input model echo $M_i(t)$ as shown in FIG. 4D, where the resulting echo is indicated in a cross (x) line. The litho-echo was also inverted to obtain the $T_2$-distribution $\tilde{C}_i(T_2)$ for each litho-type, using conventional mapping program. $\tilde{C}_i(T_2)$ depends on the random noise in the echo-data. FIGS. 4A, 4B, and 4C show the average of the inverted $T_2$-distribution from 100 random noise realizations, where the model distributions are again denoted with crossed line.

C. Error Analysis

In the simulation considered above, the total signal error is defined by $$\sigma^2 = \sum_{z,t} \left( M^{\log}(z;t) - \sum_i \tilde{h}_i(z)\tilde{M}_i(t) \right)^2 \quad \text{Eq. (16)}$$

and was computed and examined for different levels of signal error, characterized by its signal-to-noise ratio (SNR), and for different errors $\sigma_l$ in litho-weight estimates. In order to see how the GEVR processing method used in accordance with the present invention can retrieve lithology information, also computed was the lithology-echo error and $T_2$-distribution error, defined respectively by, $$\sigma_M^2 = \sum_{i,t} \left( M_i(t) - \tilde{M}_i(t) \right)^2 \text{ and } \sigma_C^2 = \sum_{i,T_2} \left( C_i(T_2) - \tilde{C}_i(T_2) \right)^2$$

In general, as the SNR increases, the error between the estimated and input lithology-echo signals decreases, as illustrated in FIG. 5A. However, when the larger error is induced in lithology-weight estimates, the larger SNR does not decrease the $T_2$-distribution error significantly, as shown in FIG. 5B. Finally, FIG. 5C illustrates a $T_2$ amplitude distribution error for the simulation example. Table 1 below further illustrates the noise properties for the simulated NMR echo example considered above.

example, in the absence of a high-resolution log, if a log measure is available that in some predictable manner reflects the average of the binary-layers, such that, if one knows both the properties of the layer-types and the law that predicts how multiple layers are averaged, one can deduce the relative fractions of the layers. One such approach is illustrated, for example, by G. Ostroff et al., "Integration of NMR and Conventional Log Data For Improved Petrophysical Evaluation of Shaly Sands", SPWLA 40th Annual Logging Symposium, May, 30–Jun. 3, 1999, the content of which is incorporated by reference for background.

Figure 7:
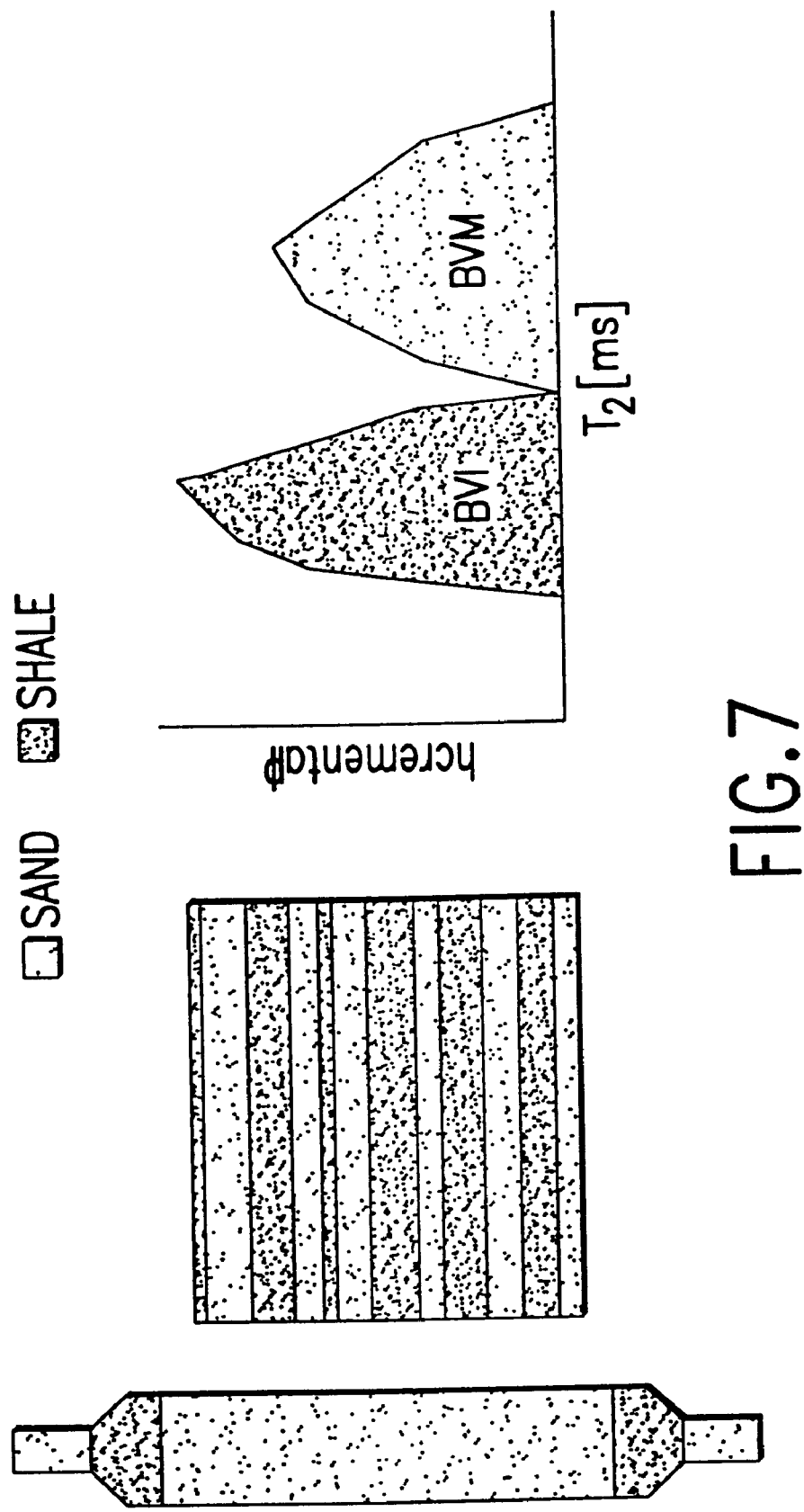
FIG. 7 is an illustration of the NMR response in a laminated two-layer sequence consisting of sand and shale.

In particular, in this approach use is made of the fact that across very thinly bedded, laminated sand-shale sequences, where the individual lamination thickness is less than that of vertical measurement resolution of the logging tool, porosity values for the individual laminations cannot be resolved using a standard NMR log. Consequently, the log total and effective log porosities $\phi_t, \phi_e$ represent the partial volume-weighted summations of the sand and shale porosity values $\phi_{shale/sand}$ integrated over the vertical measurement resolution of the logging tool, as illustrated in FIG. 7, and expressed in the following formulae:

Measured $\phi_t = [(1-V_{shale}) \cdot \phi_{tsand}] + [V_{shale} \cdot \phi_{tshale}]$
Measured $\phi_e = [(1-V_{shale}) \cdot \phi_{esand}] + [V_{shale} \cdot \phi_{eshale}]$
Measured $BVI = [(1-V_{shale}) \cdot BVI_{sand}] + [V_{shale} \cdot BVI_{shale}]$
Measured $BVM = [(1-V_{shale}) \cdot BVM_{tsand}] + [V_{shale} \cdot BVM_{tshale}]$ In the above model equations $V_{shale}$ is the laminar shale volume and not the bulk shale volume. FIG. 7 illustrates an

TABLE 1

|  | SNR = 5 | SNR = 10 | SNR = 20 | SNR = 200 |
|---|---|---|---|---|
| | | PCN = 0 | | |
| Signal Err | 0.0405 ± 0.0193 | 0.0112 ± 0.0052 | 0.0027 ± 0.0011 | 0.0004 ± 0.0007 |
| Lith. Err | 0.0094 ± 0.0064 | 0.0027 ± 0.0018 | 0.0008 ± 0.0005 | 0.0001 ± 0.0001 |
| T2 Amp. Err | 0.0023 ± 0.0006 | 0.0014 ± 0.0004 | 0.0010 ± 0.0003 | 0.0005 ± 0.0003 |
| | | PCN = 10% | | |
| Signal Err | 0.2545 ± 0.0434 | 0.2148 ± 0.0335 | 0.2118 ± 0.0337 | 0.2059 ± 0.0277 |
| Lith. Err | 0.0172 ± 0.0128 | 0.0078 ± 0.0072 | 0.0066 ± 0.0054 | 0.0059 ± 0.0085 |
| T2 Amp. Err | 0.0024 ± 0.0005 | 0.0013 ± 0.0003 | 0.0010 ± 0.0003 | 0.0004 ± 0.0005 |
| | | PCN = 20% | | |
| Signal Err | 0.8894 ± 0.1447 | 0.8335 ± 0.1456 | 0.8163 ± 0.1353 | 0.8205 ± 0.1561 |
| Lith. Err | 0.0722 ± 0.0410 | 0.0588 ± 0.0361 | 0.0572 ± 0.0381 | 0.0586 ± 0.0406 |
| T2 Amp. Err | 0.0028 ± 0.0005 | 0.0016 ± 0.0004 | 0.0012 ± 0.0004 | 0.0011 ± 0.0007 |

GEVR Processing for Field Data Applications

As discussed above, the application of the GEVR processing to actual NMR logging data, in accordance with the present invention is implemented using the following three-stage algorithm.

First, determine resolution-matched litho-weight $h_i(z)$ from high resolution tools. In accordance with a preferred embodiment, core data, if available, or high resolution log data are used to determine the resolution-matched lithology-weight $h_i(z)$. In a specific embodiment, for example, EMI resistivity, Pe, HFDT dielectric constant, and Dipmeter can be used for the high resolution log in this application. From these high resolution data, the resolution-matched litho-weight $h_i(z)$ is computed, in a specific embodiment, by taking a running-average over the poorer resolution of MRIL data.

In accordance with an alternate embodiment of the present invention, the resolution-matched litho-weight $h_i(z)$ information can be obtained using different methods. For NMR tool response in a thinly-bedded, laminated sand-shale sequence. In this embodiment, the laminations are not identified directly, but rather one estimates $V_{sh}$, which is a measure of the N/G on the scale of the logs if the formation is a laminated sand-shale sequence. If the laminar shale volume is quantified, then the pore volumetrics of the sand laminations can be re-constructed as follows:

$\phi_{tsand} = [\text{Measured } \phi_t - (V_{shale} \cdot \phi_{tshale})]/[1-V_{shale}]$
$\phi_{esand} = [\text{Measured } \phi_e - (V_{shale} \cdot \phi_{eshale})]/[1-V_{shale}]$
$BVI_{sand} = [\text{Measured } BVI - (V_{shale} \cdot BVI_{tshale})]/[1-V_{shale}]$
$BVM_{sand} = [\text{Measured } BVM - (V_{shale} \cdot BVM_{shale})]/[1-V_{shale}]$ Next, determine lithology-specific echo train $M_i(t)$. Once the resolution-matched litho-weight $h_i(z)$ is computed, the echo-train data are inverted to obtain lithology-specific echo-train Mi(t) using the equations Eq. (2), (3), and (4), described above.

Finally, invert the echo-train to a corresponding $T_2$-distribution. Conventional mapping (or inversion) processing is applied to thus obtained lithology-specific echo-train data to obtain lithology-specific $T_2$-distribution. Then, combined with litho-weights, the $T_2$-distribution is used for further log analysis. In some cases, it may be necessary to construct the echo-train data for an intermediate range of vertical resolution to match and compare to other logging tools of such resolutions. Eq. (5) is used to construct such resolution-matched echo-train from lithology-specific echo-train and resolution-matched litho-weights.

The algorithm flow chart for the field applications of the method in accordance with the present invention (a modified version of the algorithm in FIG. 6) can be expressed as follows:

Collect EMI data
    Plot EMI Identify the zone(s) of interest
    Plot Conductivity (calibrated)
    Plot Histogram (frequency of conductivity within an interval)
    Model lithology type, Define litho-thresholds (cuts)
    Generate litho-weight curve L(i;z)
NMR echo data (from a MRIL® tool)
    M(z;t)
    Run GEVR-engine
    Results: lithology-dependent echo sequences M(i;t)
    Map M(i;t) to $T_2(i)$
    Generate GEVR echos
    Map

Field Example 1

Fort Worth Test Well

1. GEVR processing with MRIL and EMI data

MRIL, EMI, and other conventional suite of logs were run in a Halliburton test well in Fortworth, Tex. FIG. 8A shows the EMI image log for the depth interval between 500 and 525 ft depth, indicating possible lamination. FIG. 8B shows the processed MRIL data ($T_2$-bin distribution and average $T_2$) and matched EMI resistivity data for the same depth interval. Note that the EMI resistivity data is sampled at every 1/10-in. interval. However, the EMI resitivity data in FIG. 8B is matched to the 4-ft resolution of MRIL.

FIG. 8C is a cross plot between the matched EMI conductivity and the average $T_2$. Strong correlation indicated in the cross plot, except for the data from 500–525 ft interval, appears to justify the use of EMI resistivity as a high-resolution lithology measurement tool. FIG. 8D is a histogram of calibrated EMI conductivity collected at every 1/10-in. interval. The histogram indicates that there are two groups of resistivity data, separated at the conductivity value of 23,000 mmho/m as the cut-off. Therefore, it can be assumed that this is a binary formation.

Next, at each measurement depth, the 1/10-in. thick layer is classified as a silt-layer or a sand-layer if the EMI conductivity is more or less than the cut-off. Then, the sand-silt ratio is computed over 1/4- or 1/2-ft interval as the ratio between the numbers of sand- and silt-layers. The litho-weight (sand fraction), $h_{sand}(z)$, thus computed is plotted in FIG. 8E.

After the GEVR processing, the two litho-echos illustrated in FIG. 8F were obtained, that correspond to two lithology types in $T_2$-distribution shown in FIG. 8G. In FIG. 8G, one lithology-type that corresponds to the high EMI conductivity has a dominant $T_2$ population at 4 ms, indicating the fast decay component in shale/silt lithology. On the other hand, another lithology-type corresponding to the low EMI conductivity has a dominant population at 60 ms, indicating slow decay component and larger pore size distribution. But it has a minor $T_2$-population also at about 2 ms. This is a reflection of the fact that resistivity alone cannot discriminate sand and shale/silt well. This is already seen in the cross plot in FIG. 8C, where some data points are found at lower $T_2$-average and lower EMI conductivity.

Figures 1, 8H:
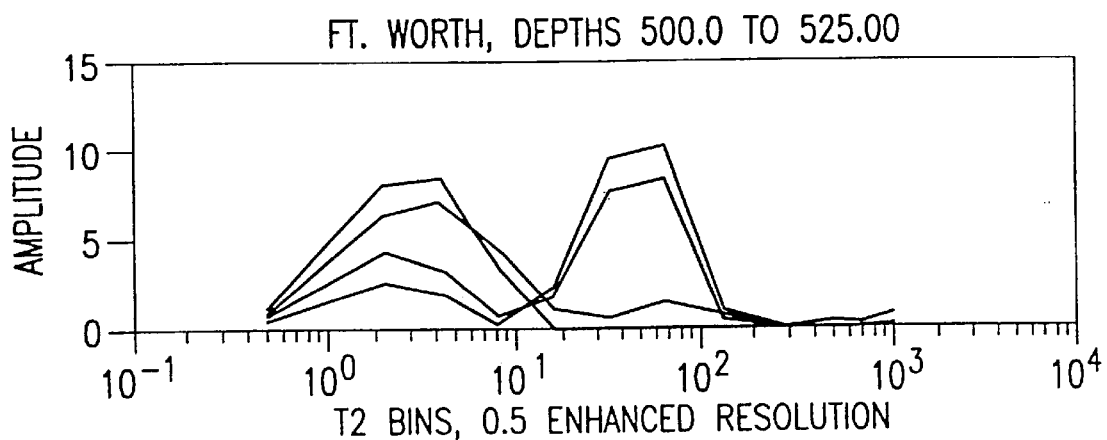
Figures 2, 8H:
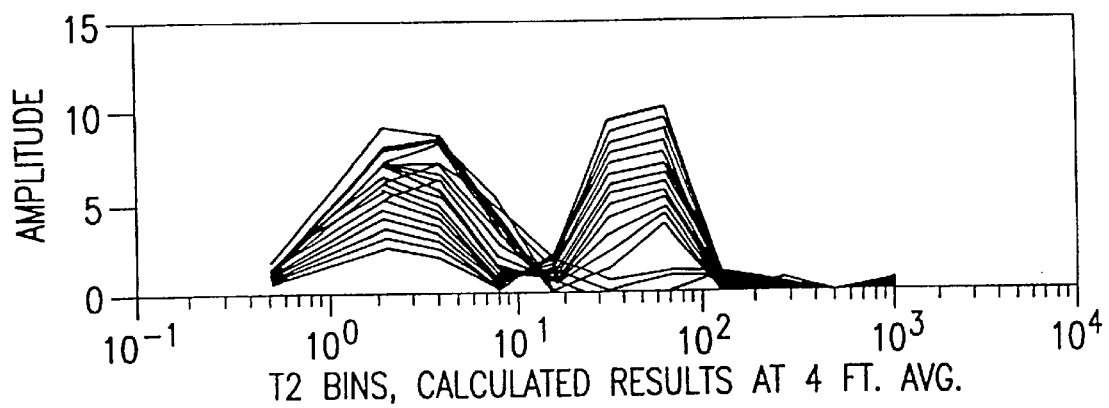
Figures 2, 8I:
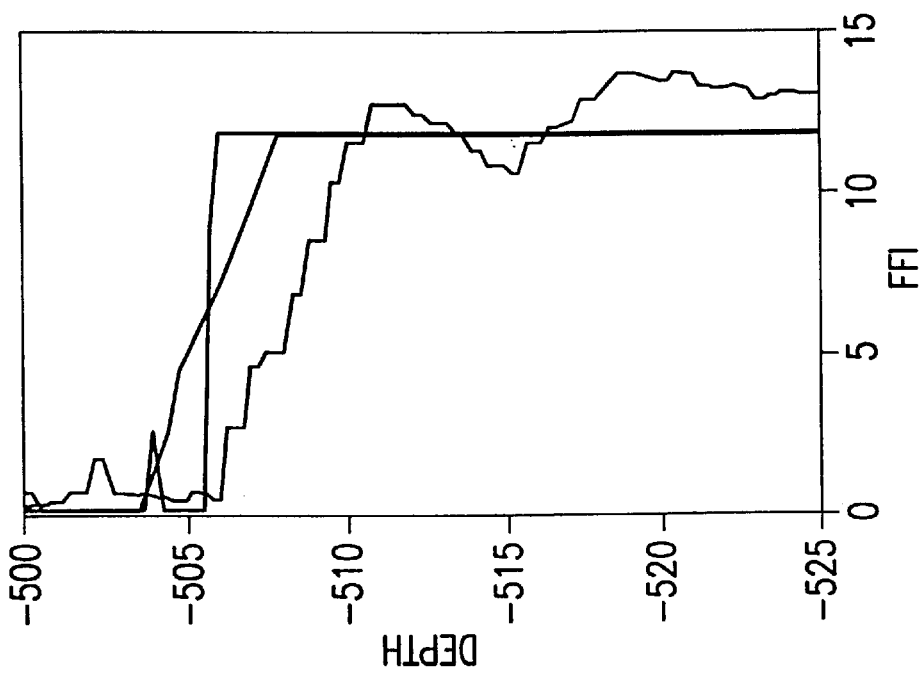
Figures 1, 8I:
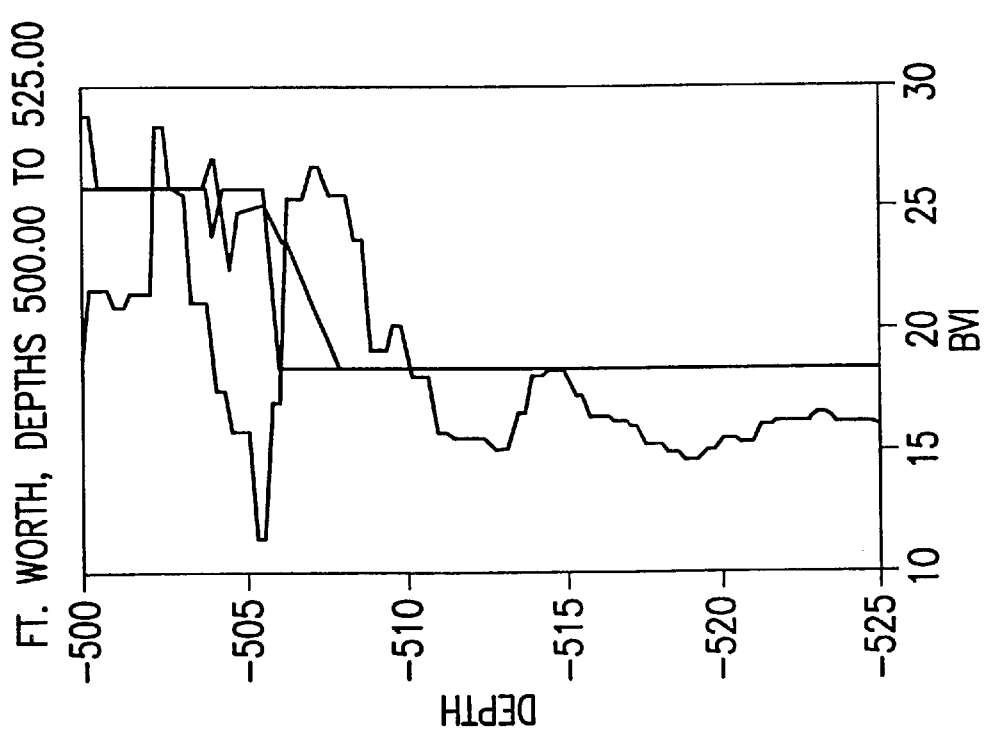

In order to check if these litho-echo trains of FIG. 8F are consistent with the original log echo-data, one can reconstruct the echo-trains using the litho-weight of FIG. 8E. The $T_2$ distributions obtained from reconstructed echo-trains are shown in FIG. 8H. Also computed were BVI and FFI from these reconstructed echo-train data and compared those from the log echo-train data. As illustrated in FIG. 8I, there is good agreement between the reconstructed and the actually measured data.

Once the litho-echo trains are obtained as in FIG. 8F, the BVI, FFI, total porosity, and the Coates permeability estimate are determined from these echo-train data for each lithological laminae. Then, using the weights obtained above, can be computed the GEVR-processed BVI, FFI, total porosity, and permeability estimates for the interval and compared with those from the log echo-train data in FIG. 8J and FIG. 8K. It should be apparent that the BVI, FFI, and total porosity should not change by the GEVR processing. On the other hand, permeability estimate is enhanced significantly after the GEVR processing.

2. GEVR processing with MRIL and Pe data

Figure 9A:
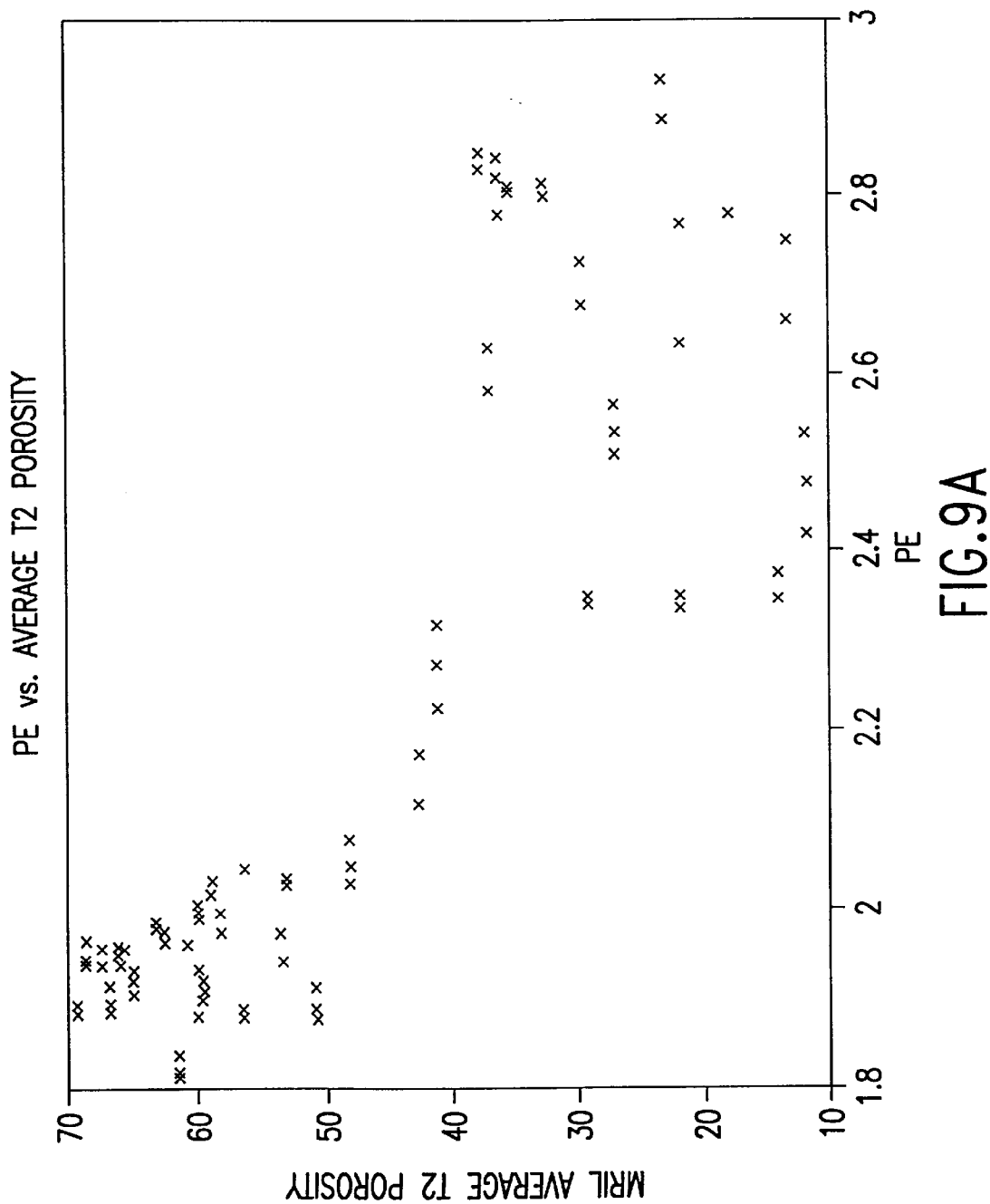
Figure 9B:
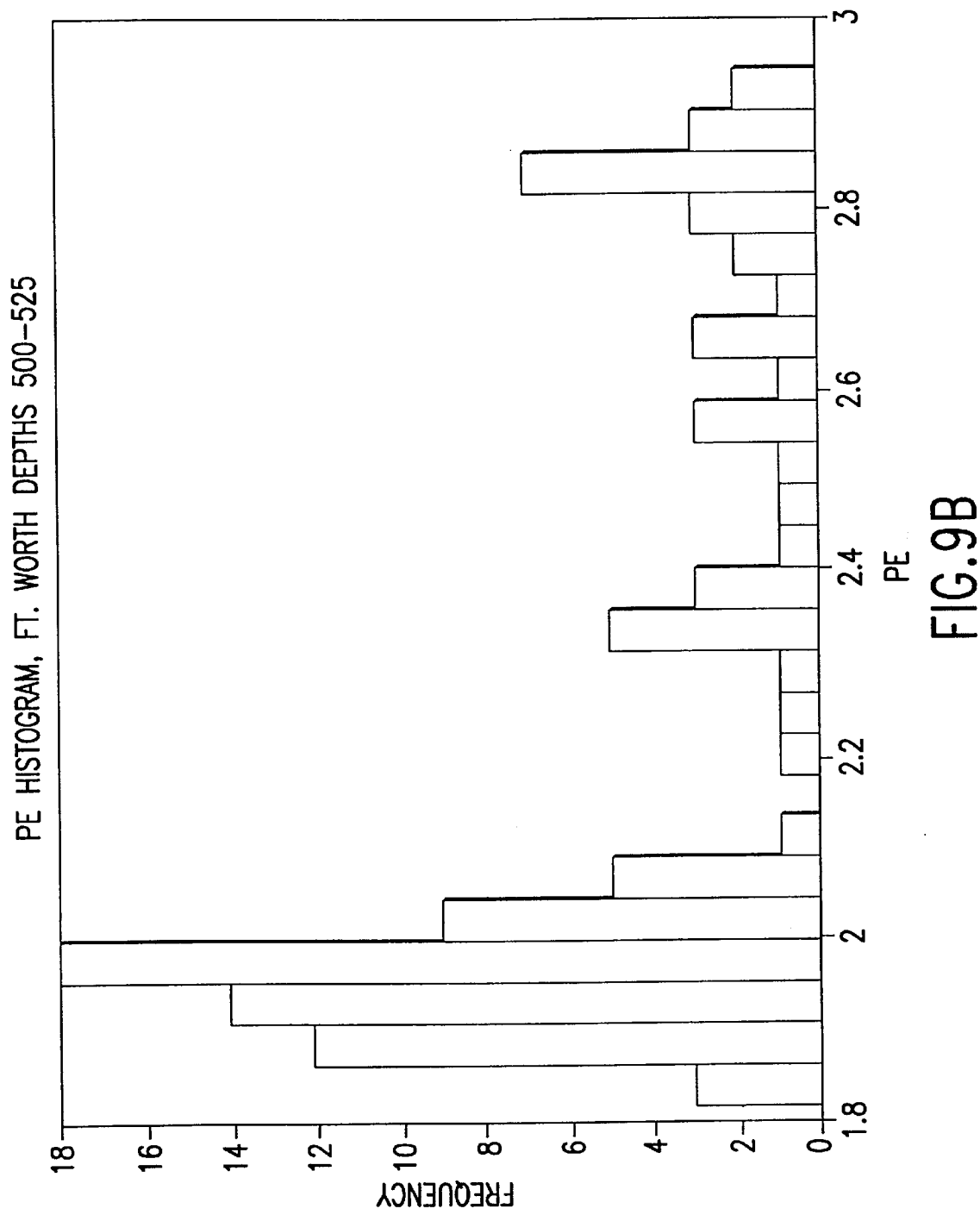
Figures 1, 9C:
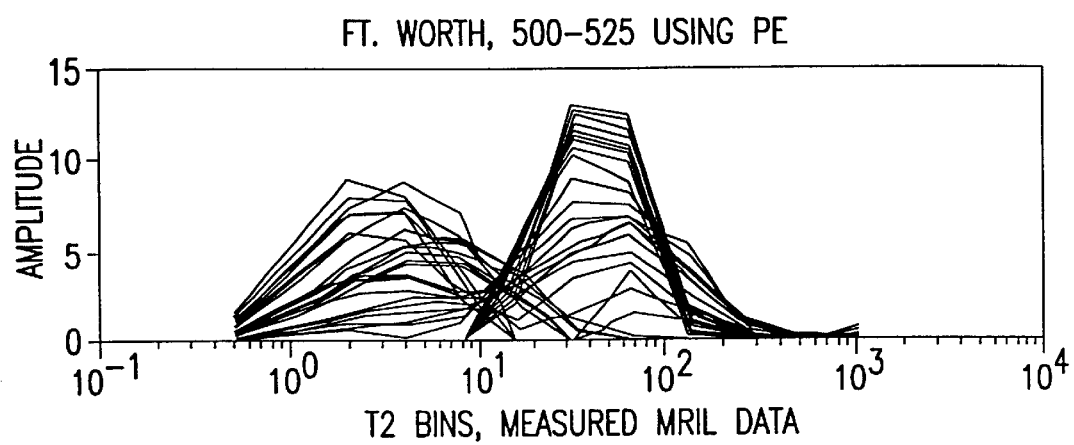
Figures 2, 9C:
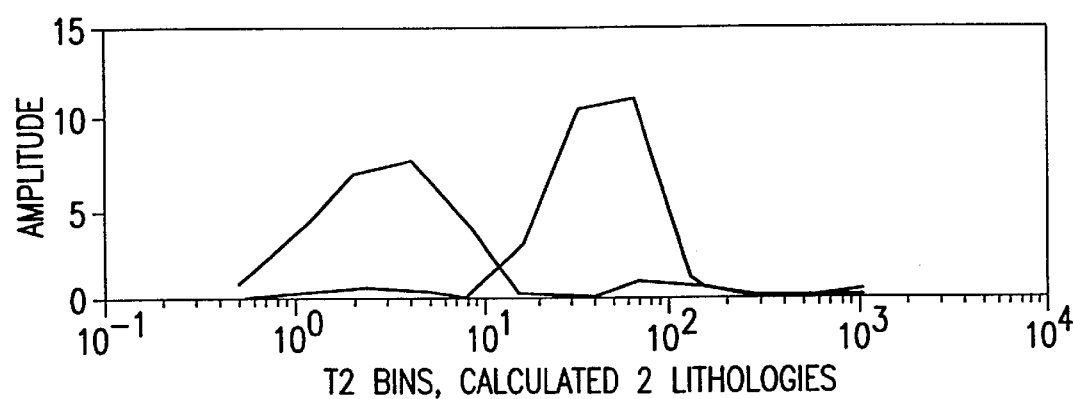

As noted above, the litho-weight information can be obtained from other logs. One such candidate is Pe-log (photoelectric log) whose 1-ft vertical resolution is still better than that of MRIL. FIG. 9A shows the cross plot of Pe and $T_2$-average for the same 500–525 ft depth interval. The Pe histogram is shown in FIG. 9B. The litho-weight was generated from the Pe data with the cutoff selected at Pe=2.2. Two lithology-types in $T_2$ distribution obtained by using the Pe-based litho-weight are shown in FIG. 9C.

Field Example 2

A Gulf of Mexico Reservoir

The GEVR processing in accordance with the present invention was also applied to the MRIL and EMI data logged in a Gulf of Mexico reservoir, as illustrated below.

Depth interval X422–X427 ft

Figures 2, 10A:
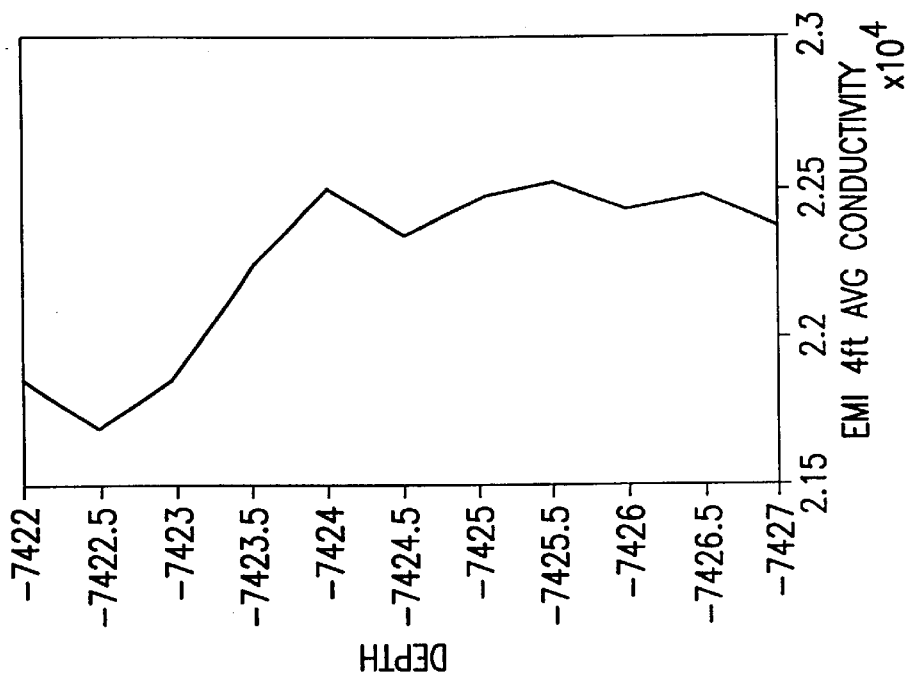
Figures 1, 10A:
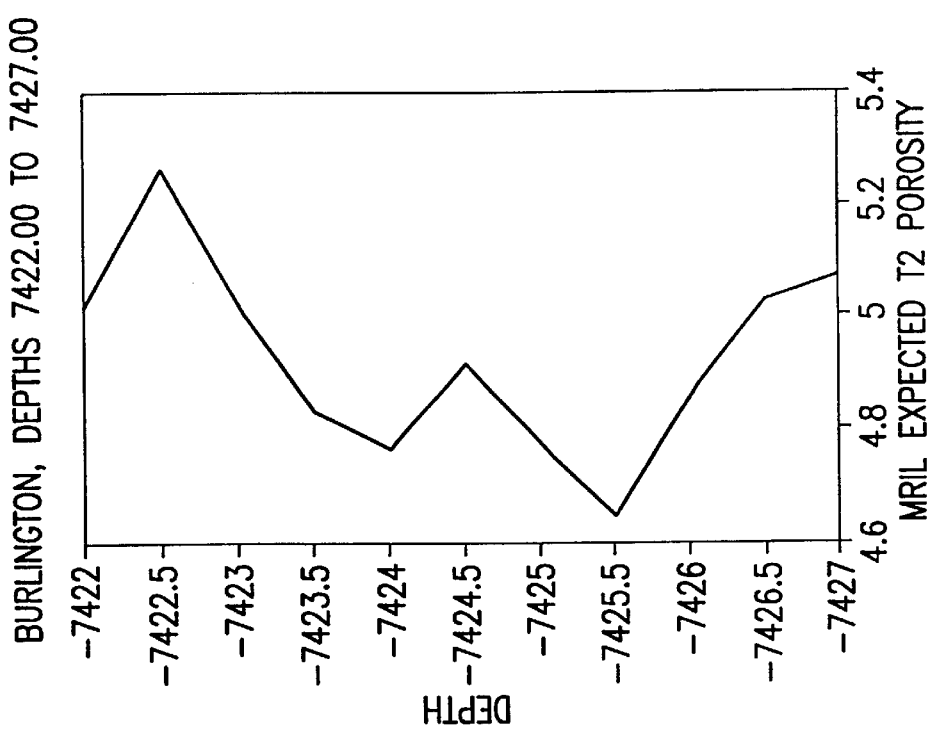
Figure 10C:
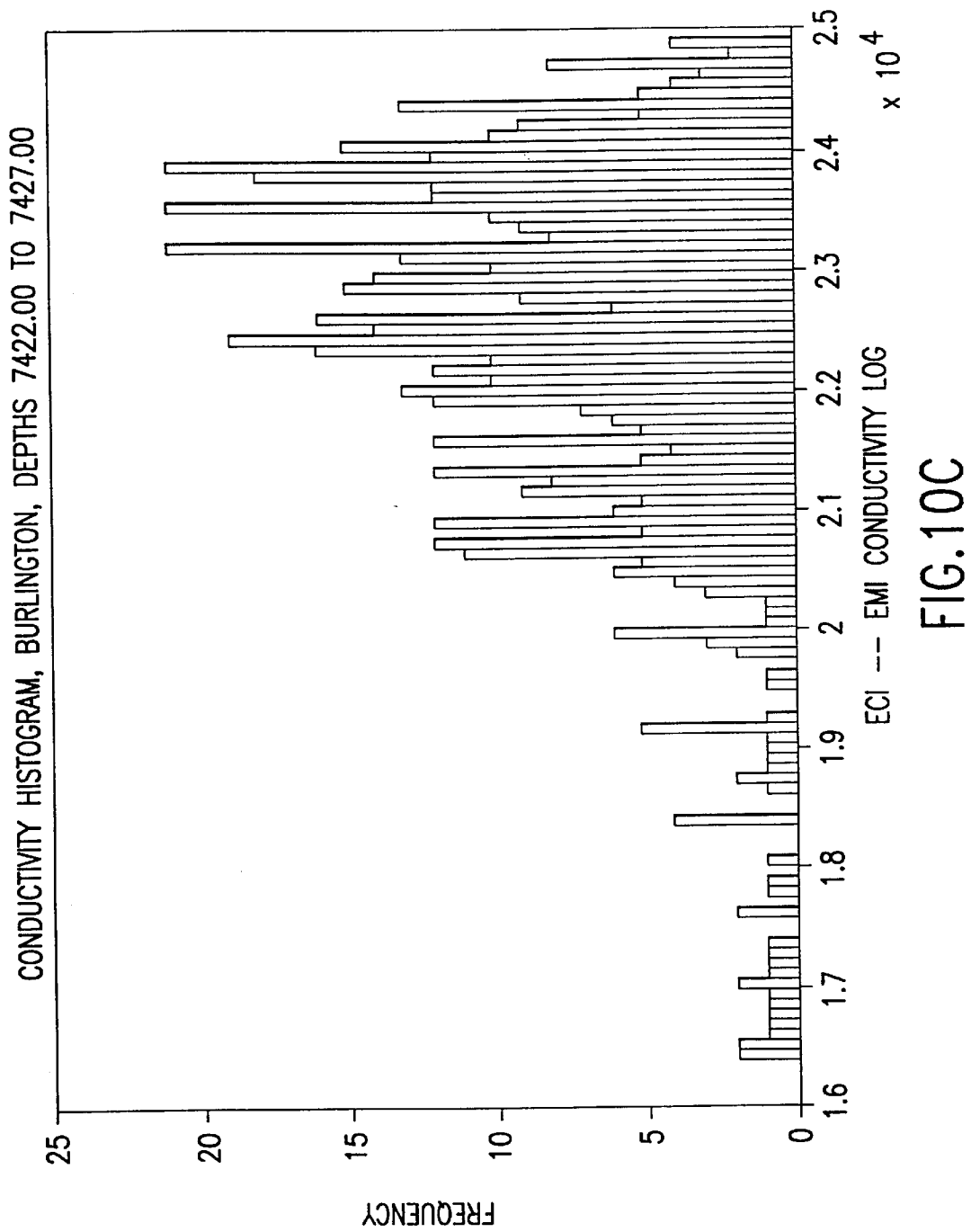

The MRIL $T_2$-average and EMI resistivity averaged over 4-ft are plotted in FIG. 10A. Their cross plot (FIG. 10B) indicates that EMI resistivity may be used as a lithology indicator as the difference in $T_2$-average often caused by lithological change. The EMI conductivity histogram of FIG. 10C may indicate the cutoff conductivity to be at 23,000 mmho/m, which is the same as in the case of Fortworth test well.

Figures 2, 10D:
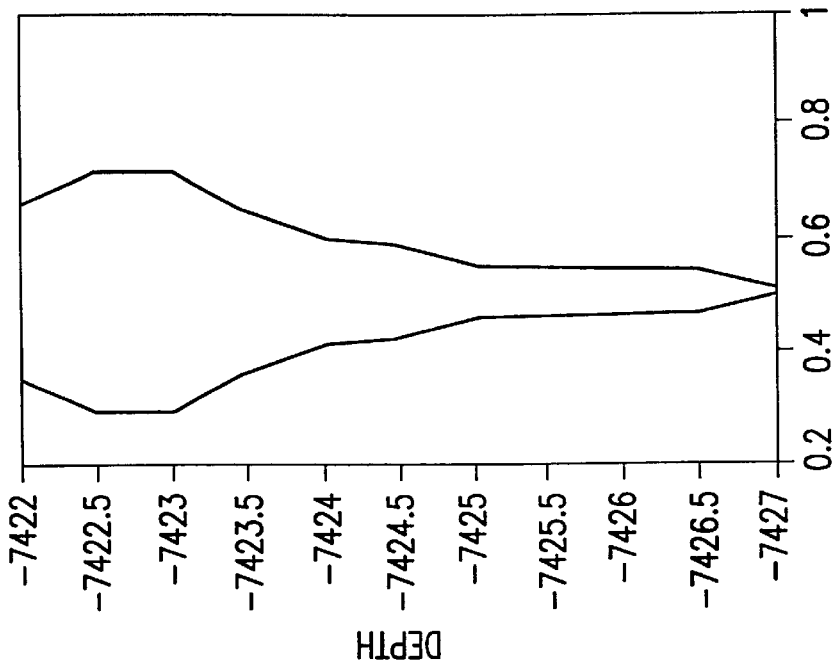
Figures 1, 10D:
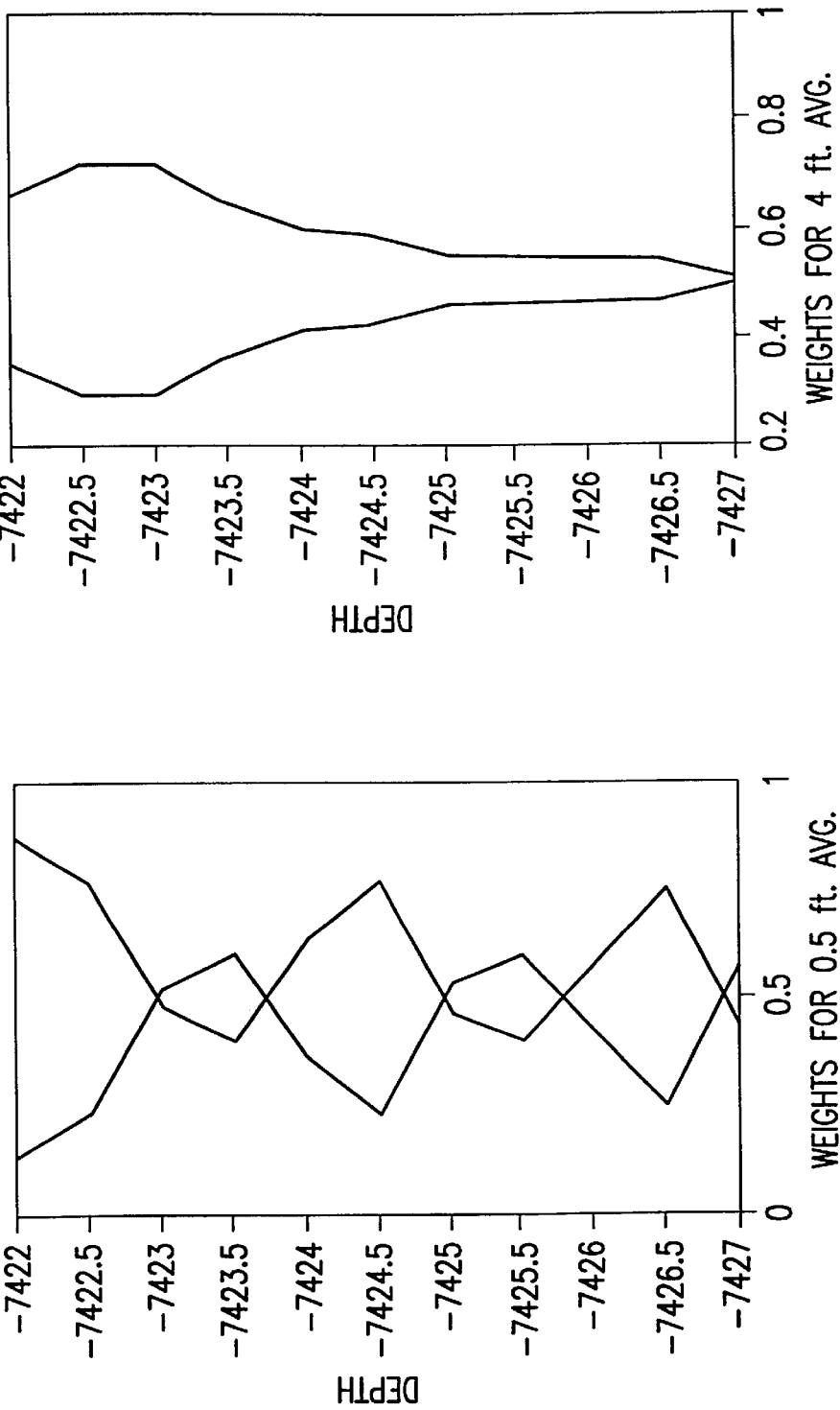

The litho-weight is derived from the EMI conductivity, as shown in FIG. 10D, where the weight is computed over 1/2-ft interval in the left and over 4-ft interval in the right. The GEVR processing resulted in two litho-echo trains for sand and silt laminae, which correspond to the following two distinctly different lithology-types in $T_2$-distribution, as shown in FIG. 10E. The more resistive laminae has $T_2$ components longer than 32 ms. The more conductive laminae has only $T_2$-components shorter than 32 ms.

Figures 1, 10F:
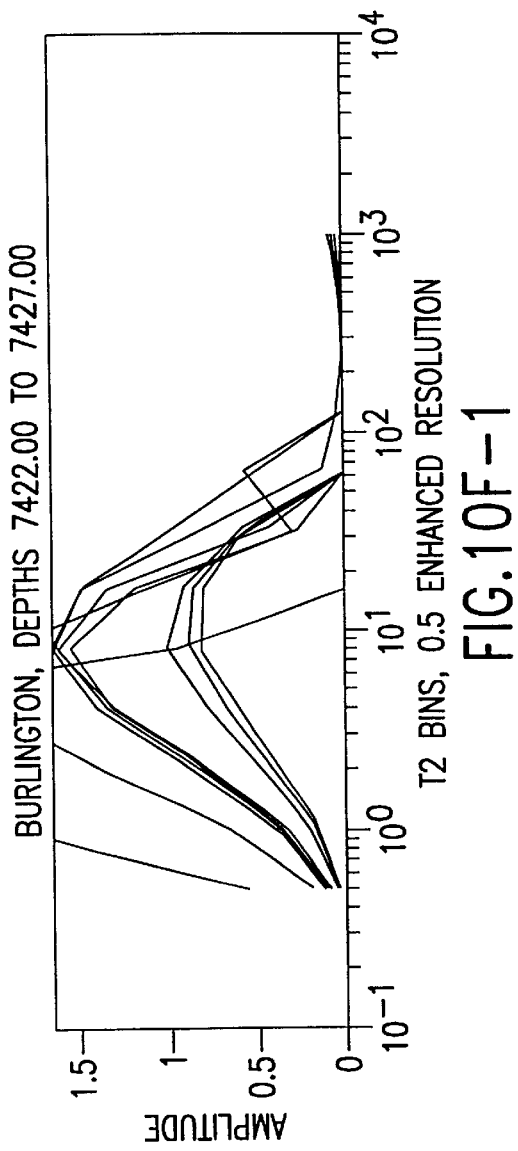
Figures 2, 10F:
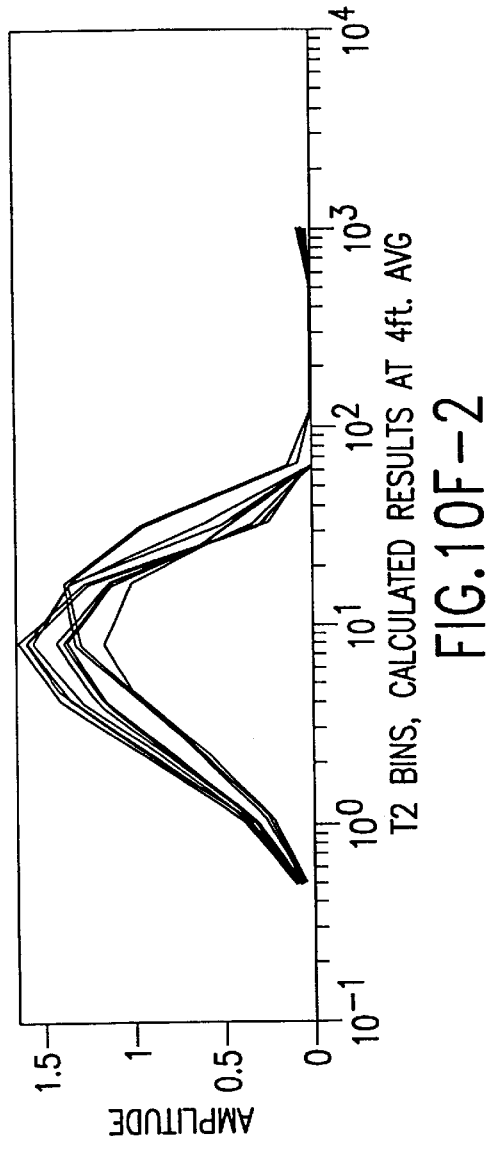
Figures 2, 10G:
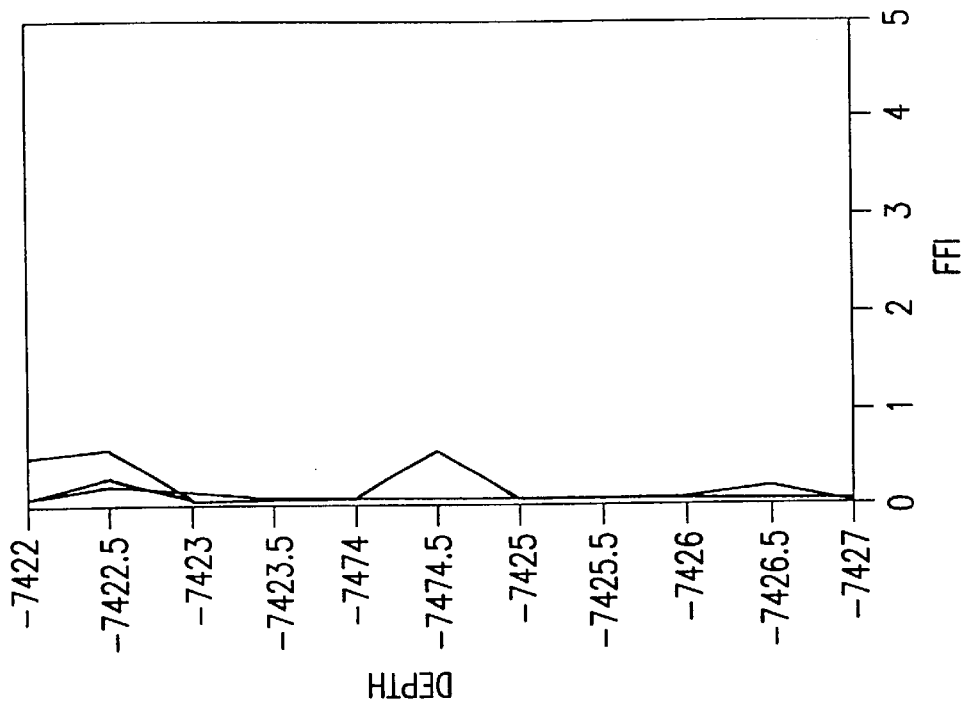
Figures 1, 10G:
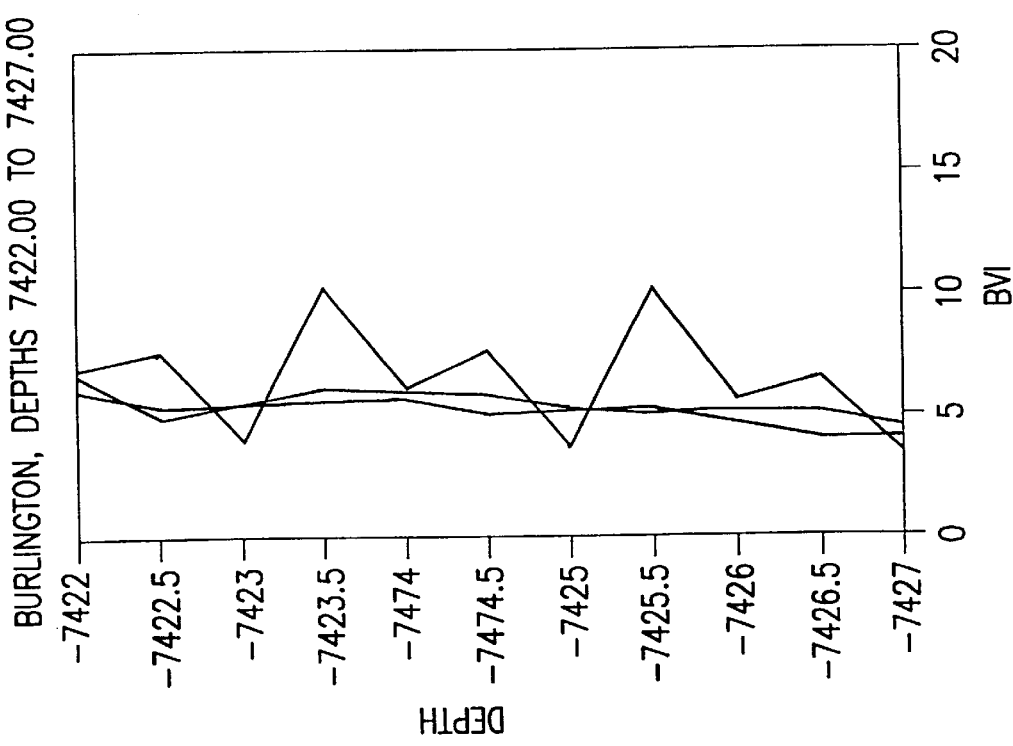

In order to check if these litho-echo trains are consistent with the original log echo-data, in this experiment applicants reconstructed echo-trains using the litho-weight of FIG. 10D. The $T_2$ distributions obtained from reconstructed echo-trains are shown in FIG. 10F. Also computed were BVI and FFI from these reconstructed echo-train data and compared those from the log echo-train data. The good agreement is illustrated in FIG. 10G.

Figures 2, 10H:
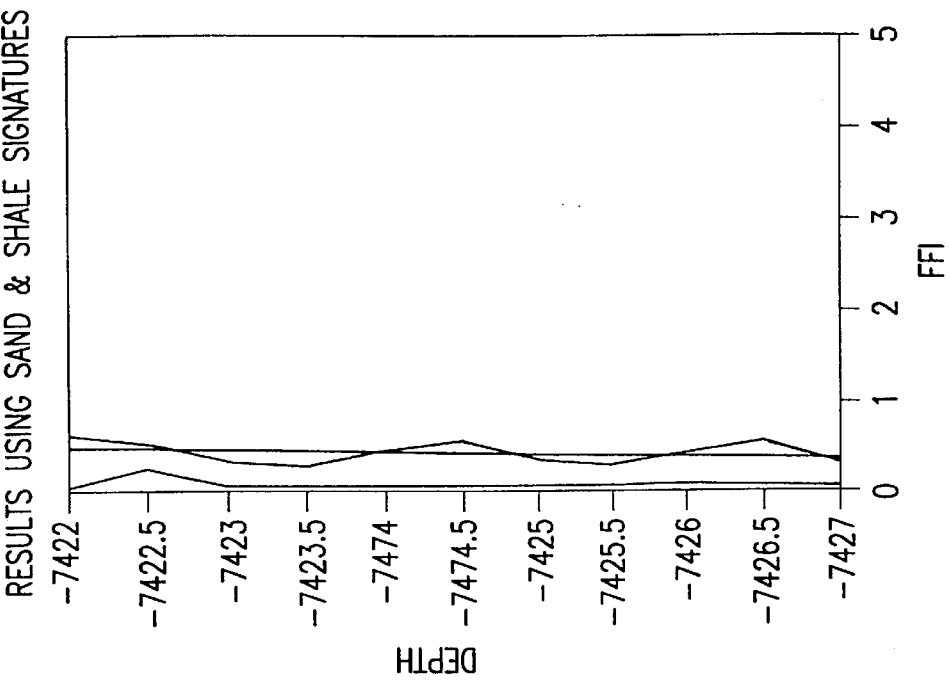
Figures 1, 10H:
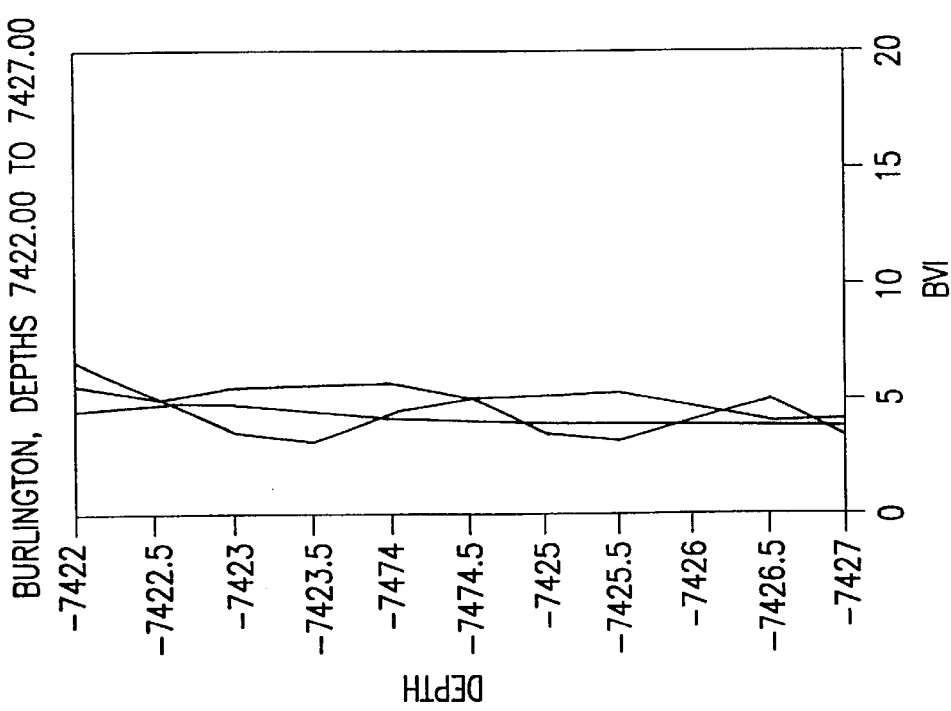
Figures 2, 10I:
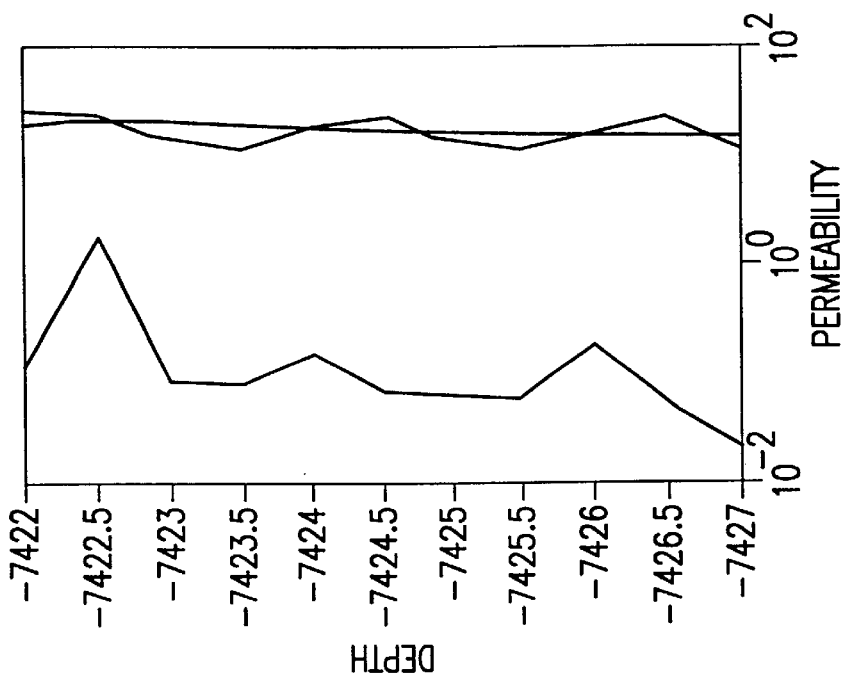
Figures 1, 10I:
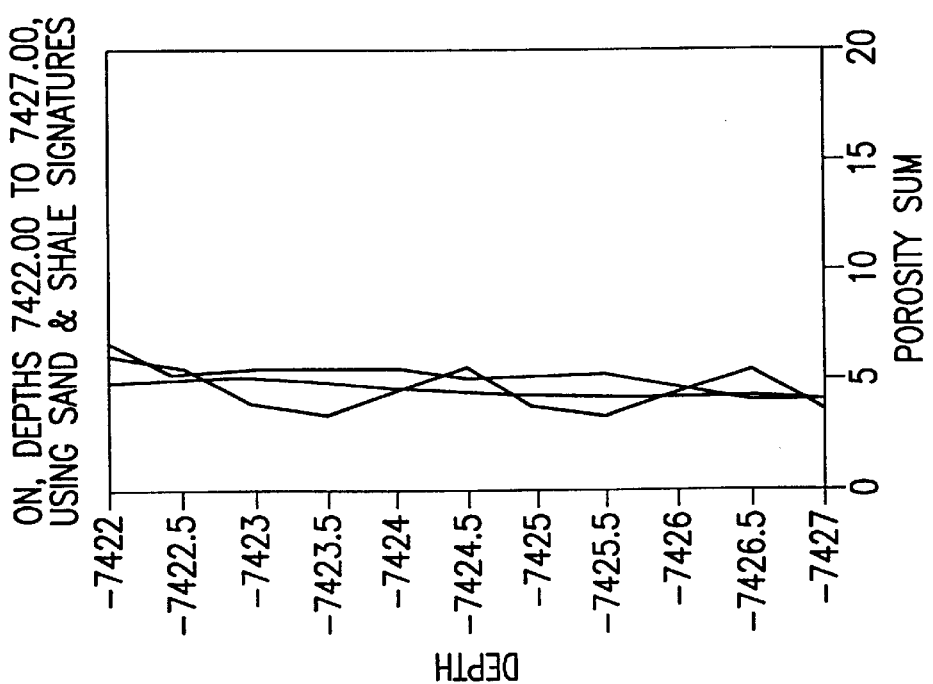

Once the litho-echo trains were obtained as above, the BVI, FFI, total porosity, and the Coates permeability estimate were determined for each lithological laminae. Then, using the weights obtained above, were computed the GEVR-processed BVI, FFI, total porosity, and permeability estimates for the interval and compared with those from the log echo-train data in FIG. 10H and FIG. 10I. As noted, the BVI, FFI, and total porosity should not change by the GEVR processing. On the other hand, permeability estimate is enhanced significantly after the GEVR processing.

Figure 10J:
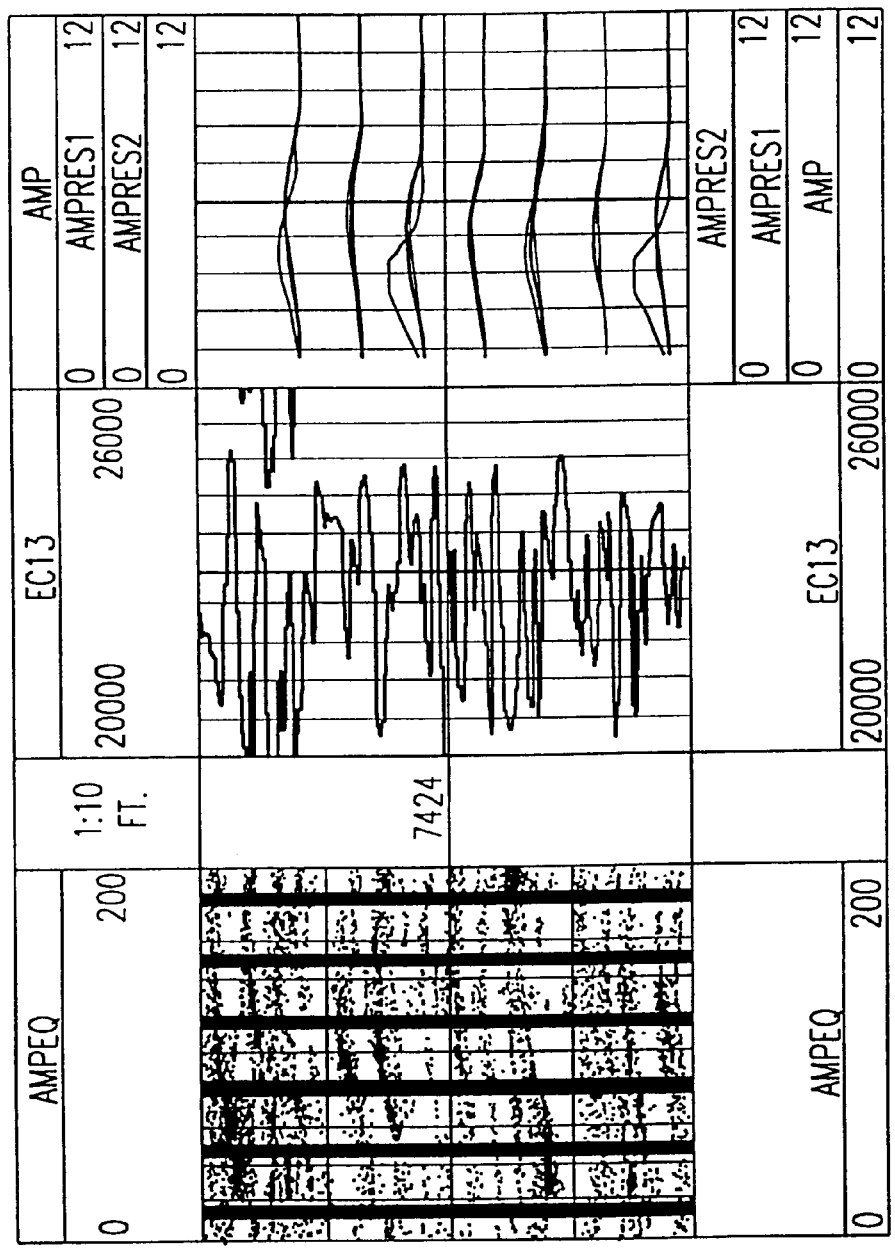
Figure 10K:
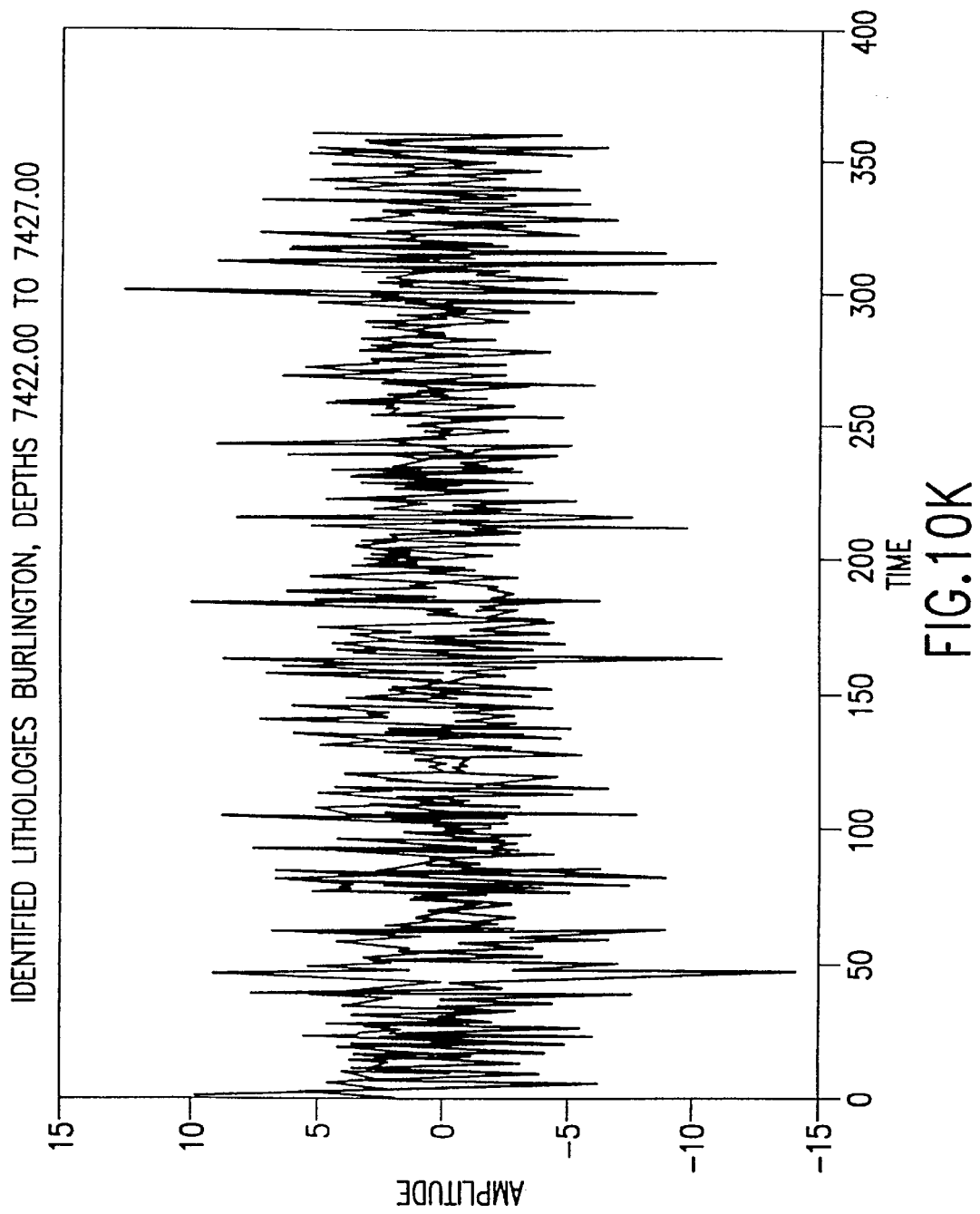

Plotted in FIG. 10J are EMI image data on the left track, EMI resistivity on the center track, and the $T_2$-distribution mapped from reconstructed echo-train on the right track. Both results reconstructed from the 4-ft average and the ½-ft average weights are shown together.

Based on the above, it should be apparent that system and method in accordance with this invention address various practical applications, including:

- estimating high-resolution formation properties for 2D data (e.g., depth-varying MRILecho-train, or PSGT Nuclear spectra) rather than simple 1D data (e.g., depth-varying BVI from MRIL, or C/O-Ratio from RMT);
- estimating the formation properties in situations where there are more than three layers types detected, and quantified, by a high-resolution logging device.

Figure 11:
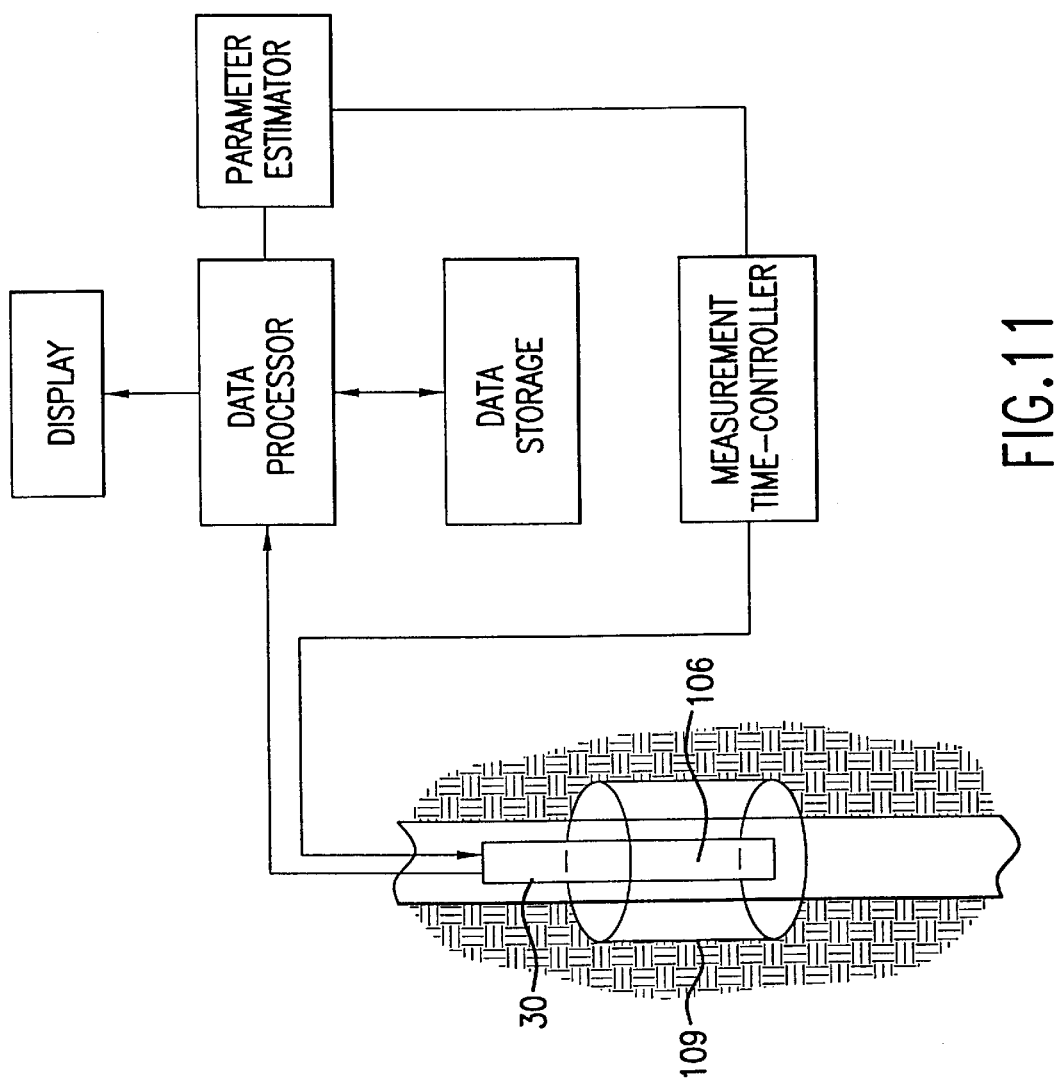
FIG. 11 is a block diagram illustration of a system in accordance with the present invention.

FIG. 11 is a block diagram of a system in accordance with a specific embodiment of the present invention, which shows individual block components for controlling data collection, processing of the collected data and displaying the measurement results. In FIG. 11 a logging tool 30 comprises an MRI probe controller and pulse echo detection electronics. Not illustrated separately in the figure, a high-resolution tool, such as an EMI tool is also lowered in a borehole in the formation 109. The output signal from the tool(s) detection electronics is processed by data processor 52 to: record high-resolution data from the EMI tool and analyze the relaxation characteristics of the sample. The output of the data processor 52 is fed to parameter estimator 54. Measurement cycle controller 55 provides an appropriate control signal to the MRI probe. The processed data from the log measurements is stored in data storage 56. Data processor 52 is connected to display 58 which is capable of providing a graphical display of one or more measurement parameters, preferably superimposed on display data from data storage 56. The components of the system of the present invention shown in FIG. 11 can be implemented in hardware or software, or any combination thereof suitable for practical purposes.

ENHANCED VERTICAL RESOLUTION USING NEURAL NETWORKS

In another important aspect, the system and method of the present invention use neural networks to enhance the vertical resolution of various log measurements. The neural network approach described below can be used in addition to or instead of the above resolution enhancement techniques.

To fully appreciate the various aspects and benefits produced by the present invention, a basic understanding of neural network technology is required. Following is a brief discussion of this technology, as applicable to the system and method of the present invention.

Artificial neural networks loosely model the functioning of a biological neural network, such as the human brain. Accordingly, neural networks are typically implemented as computer simulations of a system of interconnected neurons. In particular, neural networks are hierarchical collections of interconnected processing elements configured, for example, in a standard three-layer structure. A standard neural network has an input layer of processing elements, a middle layer of processing elements, and an output layer composed of one or more processing elements.

Turning next to the structure of a neural network, each of its processing elements receives multiple input signals, or data values, that are processed to compute a single output. The output value is calculated using a mathematical equation, known in the art as an activation function or a transfer function that specifies the relationship between input data values. As known in the art, the activation function may include a threshold, or a bias element. The outputs of elements at lower network levels are provided as inputs to elements at higher levels. The highest level element (s) produce a final system output. In the context of the present invention, a neural network may be implemented as a computer simulation that produces output based on available log measurements, human knowledge, and other factors.

As described below, the neural network used in accordance with the present invention is constructed by specifying the number, arrangement, and connection of the processing elements, which make up the network. A simple embodiment of a neural network consists of a fully connected network of processing elements. The processing elements are grouped into layers: an input layer receiving input data from one or more log measurements; a middle layer of processing; and an output layer. The number of connections, and consequently the number of connection weights, is fixed by the number of elements in each layer. There is no need to specify a particular structure—all that is required by the present invention is that a network be able to be trained and retrained, if necessary, to result in the resolution enhancement of a given log.

In a specific embodiment, the neural network approach applied in accordance with the present invention is used to enhance the vertical resolution of a NMR tool that measures formation properties through an echo train. As noted above, the MRIL® logging tools can be sampled at about ¼ ft, however, their vertical resolution may be limited by the tool specifications to about 2–4 ft. The neural network approach described below shows how the tool response can be enhanced to reproduce finer resolution data. It should be emphasized that the method can be generalized in a straight-forward manner and applied to other logging tools as well.

As noted, neural networks can be considered as black boxes that map input data to output data through nonlinear mathematical modeling. Typical applications include forecasting (prediction), function approximation, classification, and data interpolation. All of these functions can be directly used in log analysis and prediction. In the oil industry, several tools are usually run at the same area. Missing information from one log can be predicted using data from the other logs.

Neural network models can be used to map finer resolution logging tool responses to the MRIL response. The training set may be composed of inputs such as EMI (Electromagnetic Imaging), PE (PhotoElectric), and NPHI (Neutron Porosity). The output reading of the network model is generally a MRIL $T_2$ Distribution Amplitudes, as described in the above-recited patents. In accordance with a preferred embodiment, the number of output nodes equals the number of bins used.

The proposed method consists of two stages: development and enhancement. In a preferred embodiment, during the development stage the input data from one or more tools is downsampled to approximately correspond to the MRIL readings. Then the input/output data is divided into training and testing sets. As will be appreciated by people skilled in the operation of neural networks, by iterating over the desired target output in the training set, the network model can be trained to reduce the squared error difference between desired and calculated outputs. Once the network converges, the testing set may be used to validate the network accuracy.

In the second, enhancement stage used in accordance with the present invention, the input readings are averaged over a sample distance, such as 4 ft, to correspond to the "normal" resolution of the tool, i.e., resolution matching is performed. In the case of the MRIL tool, this resolution is on the order of 4 feet. Next, the input/output patterns are used to train the network and target the available MRIL readings. Finally, finer resolution readings, such as ¼ ft in the case of the MRIL tool, are used as the network inputs to produce the desired enhanced readings.

2. Processing Algorithm:

In a preferred embodiment the processing algorithm of the present invention is as follows:

(a) Stage 1: Neural Network Development
  1.1 Choose Network Architecture & Learning Algorithm
  1.2 Choose Input curves
  1.3 Down sample the input data
  1.4 Divide the input/output data into training & testing sets (using, for example, every other point)
  1.5 Train the network to map input/output to reduce the squared error
  1.6 Once the network converges, use testing data to validate (b) Stage 2: Enhanced Resolution
  2.1 Use Network Architecture & Learning Algorithm developed in stage 1
  2.2 Use same input curves as in stage 1
  2.3 Average input data for Resolution matching
  2.4 Train the network for input/output patters at MRIL resolution
  2.5 Once the network converges, use high resolution input curves to give the desired enhanced readings The steps identified in the two stages of the process in accordance with a preferred embodiment can be practiced as illustrated in a specific example below. It should be understood, however, that the example is merely illustrative of the approach, and modifications will be apparent to those of skill in the art. Further, as noted, the application of the above algorithm is not limited to the MRIL tool and can be generalized for application to any other logs with single and/or multiple value readings.

EXAMPLE:

Data was provided from the Ft. Worth Test Well. The EMI and PE logs were used as the inputs to the network. The outputs were the 12-bin $T_2$ amplitude distribution from the MRIL log. The total processed depth used was 25 feet with readings at ¼ ft. Therefore a total of 100 data sets were used.

As part of the network development stage, the network architecture chosen had 3-layers with 2 input, 7 hidden, and 12 output neurons. The activation function used was the Sigmoid and the training method was the Levenburg-Marquadt, which are known in the art. The optimum network used was drawn form a pool of 25 randomly initialized networks with maximum of 25 iterations.

Figure 12A:
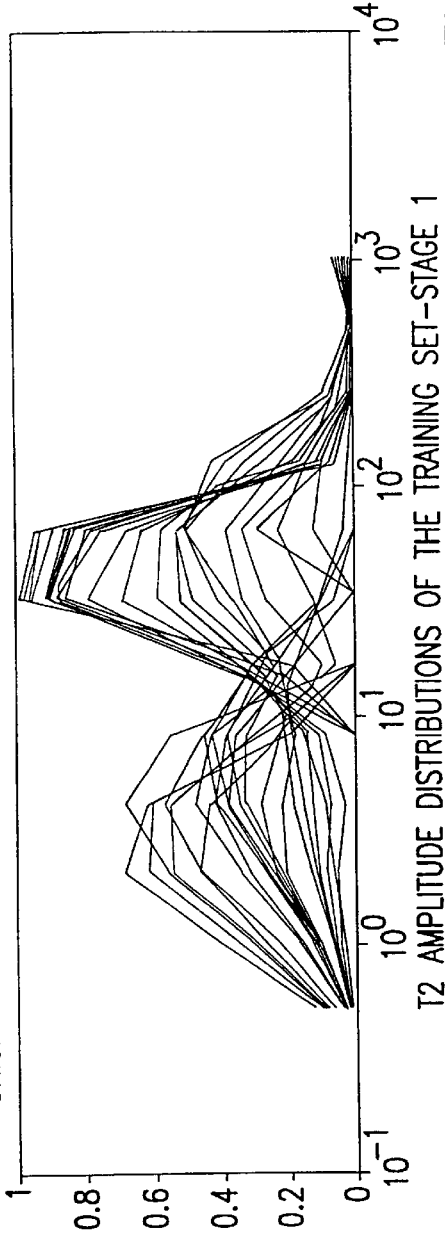
FIGS. 12 and 13 illustrate the errors for the training and testing sets in the first stage of the neural network resolution enhancement approach of the present invention.
Figure 12B:
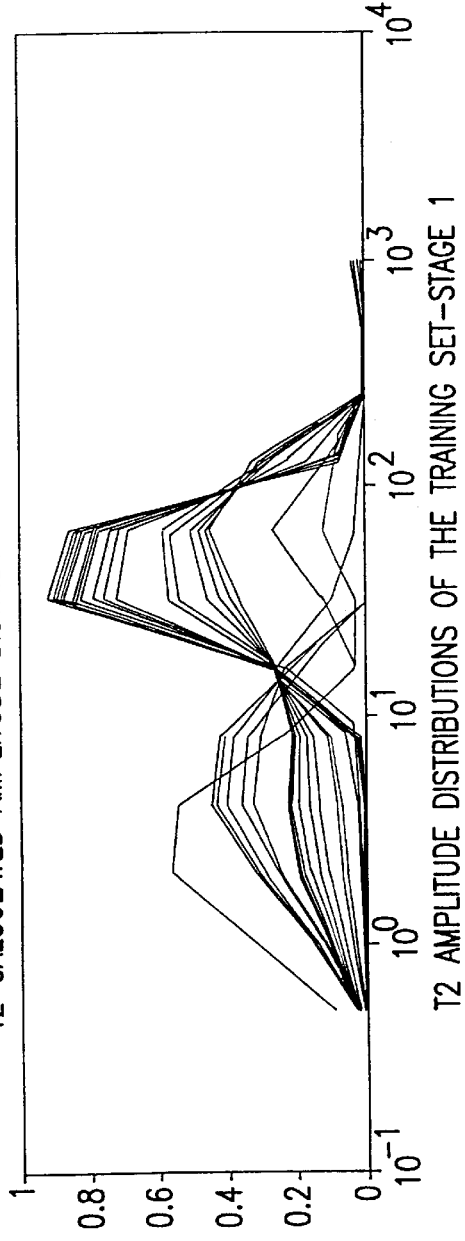
Figure 13A:
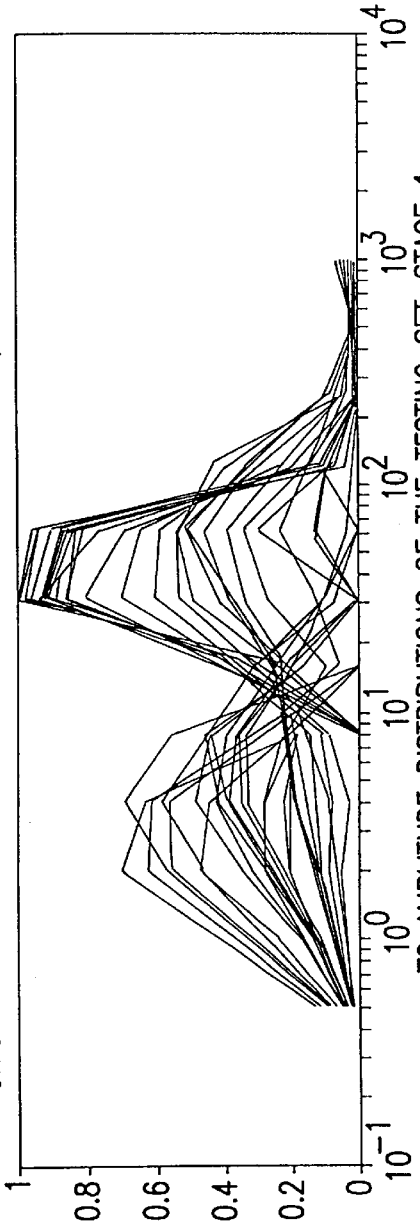
Figure 13B:
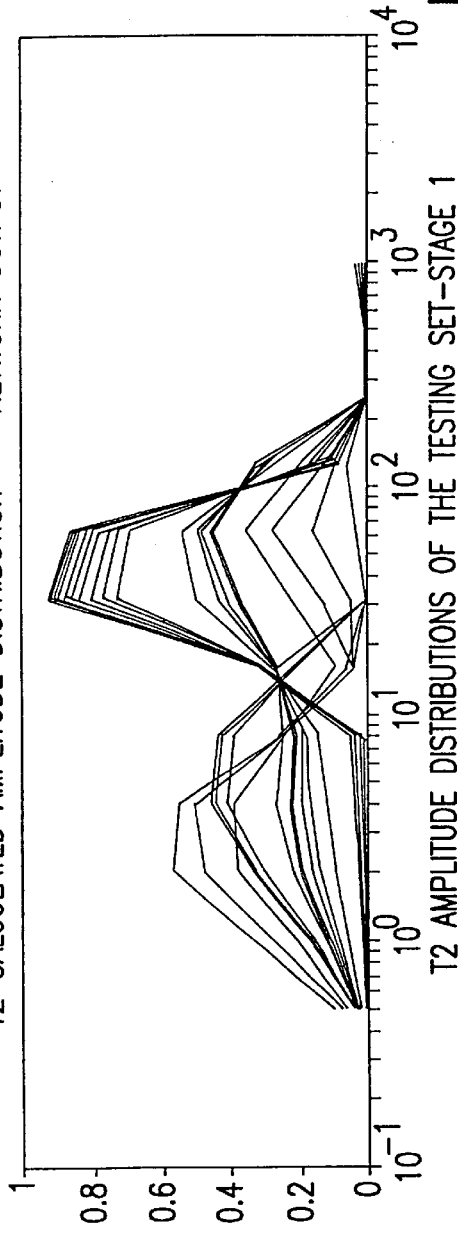

In the first stage, the data was divided into training the testing sets each with 50 data sets. After the network converged, the test data was used to validate the results. The mean square errors for the training and testing sets were 0.0021 and 0.0033. Those results are shown in FIGS. 12 and 13.

Figure 14A:
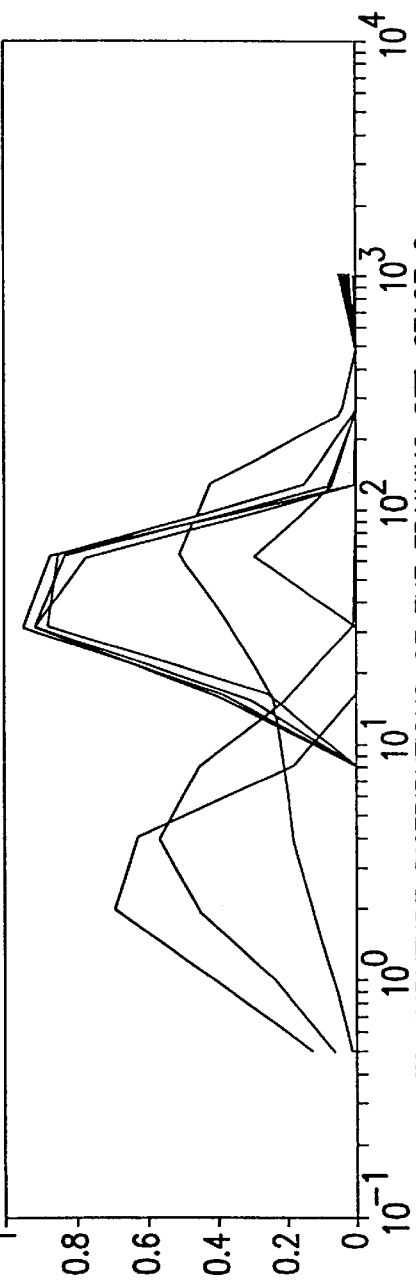
FIG. 14 illustrates the errors for input data (EMI and PE) in the second stage of the neural network resolution enhancement approach of the present invention.
Figure 14B:
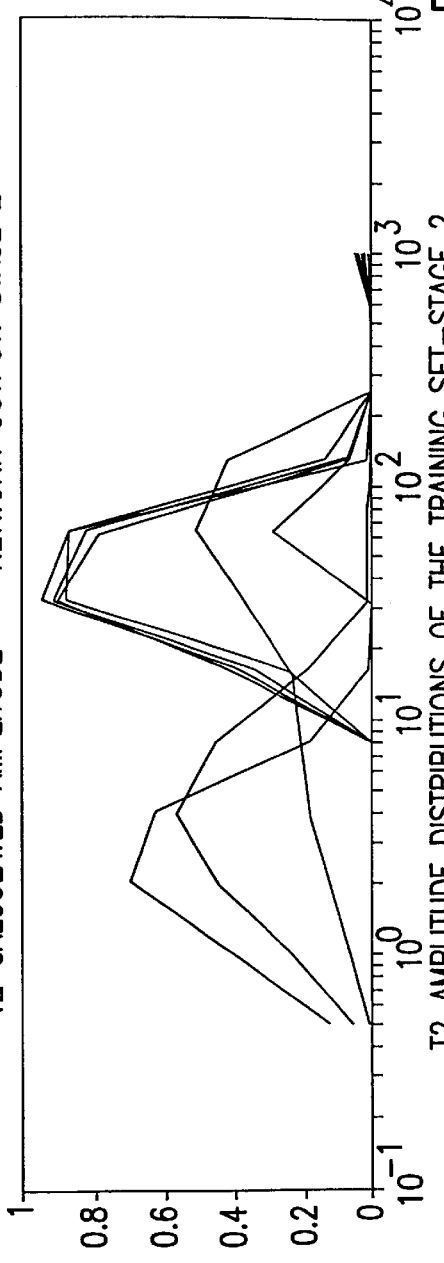
Figure 15A:
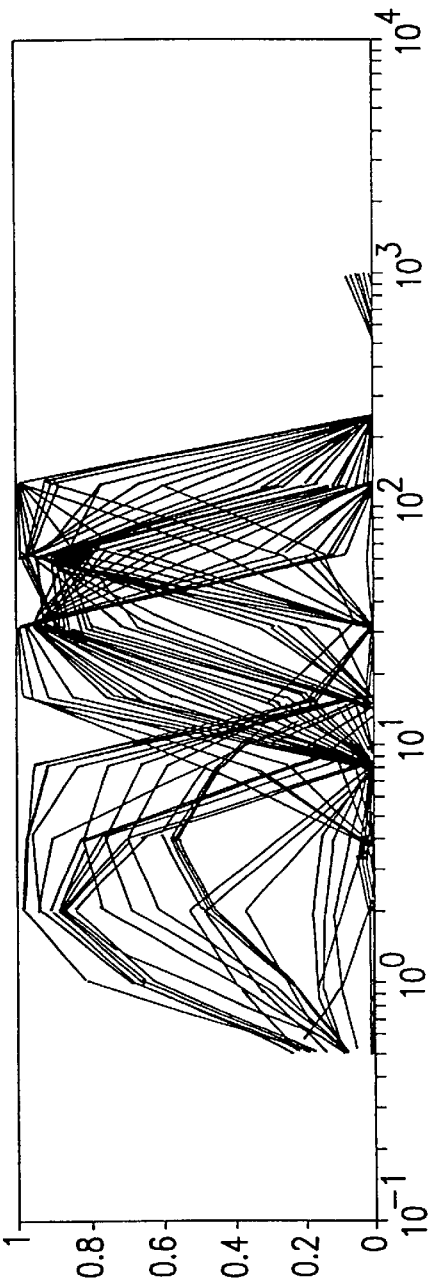
FIG. 15 illustrates the errors for the enhanced readings in accordance with the neural network resolution enhancement approach of the present invention.
Figure 15B:
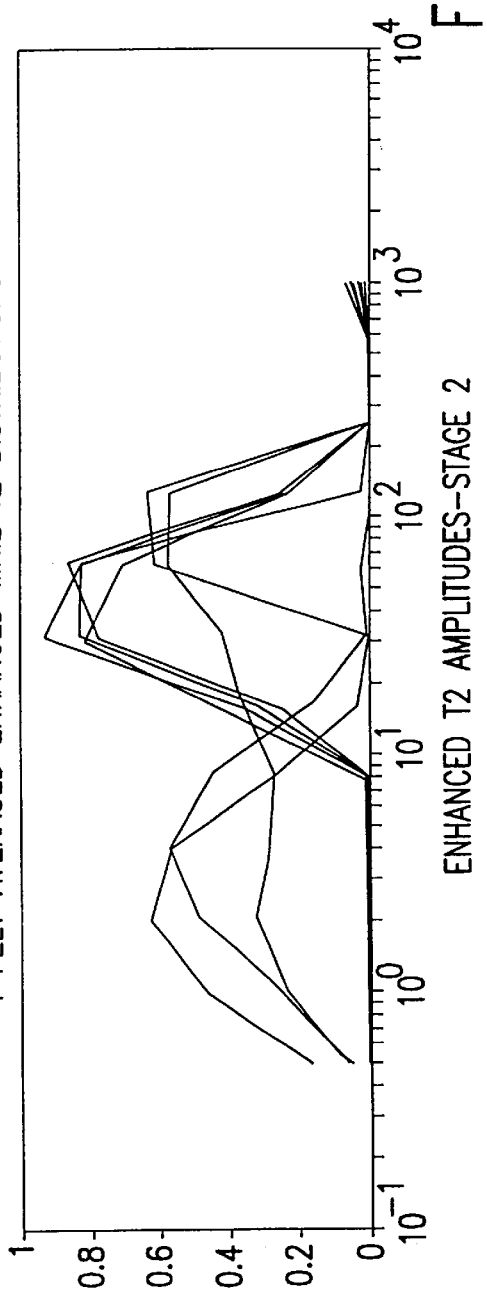
Figure 16A:
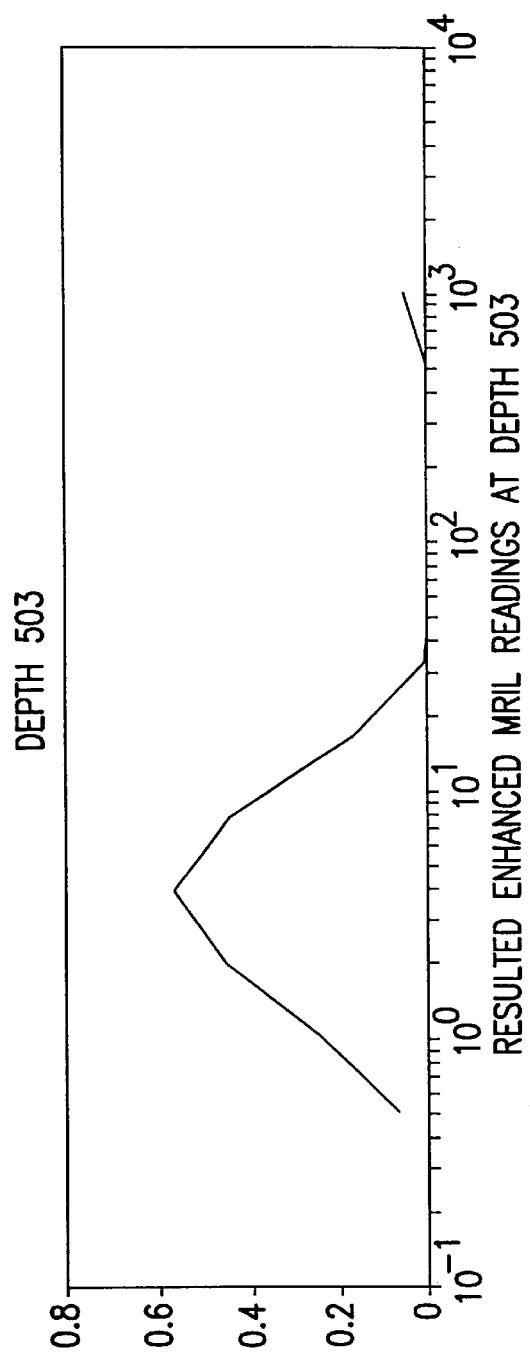
Figure 16B:
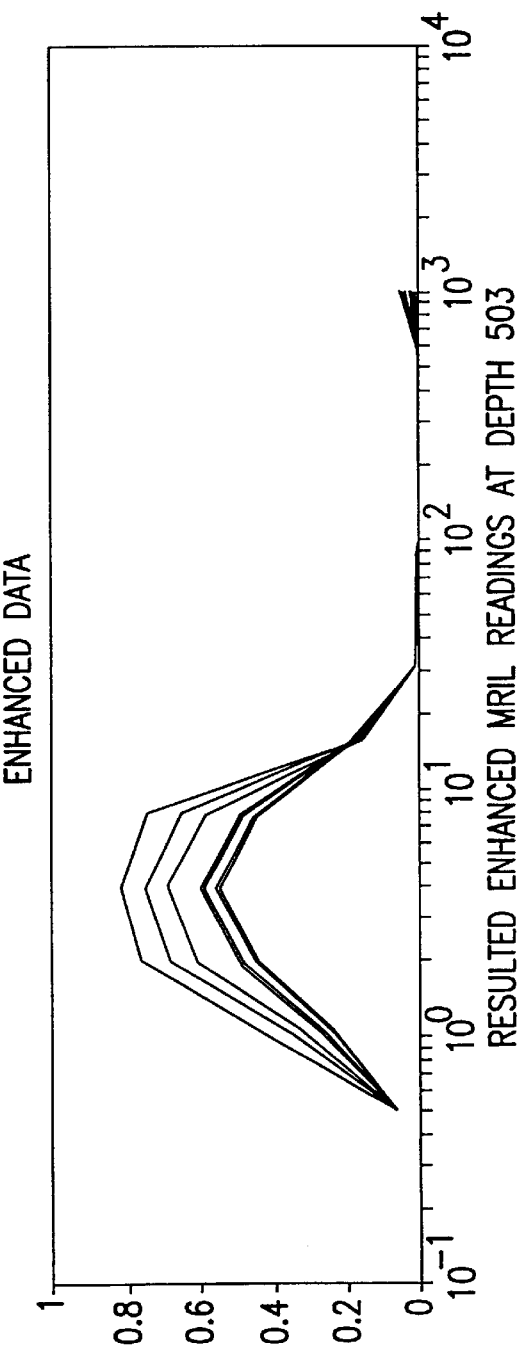
Figure 17A:
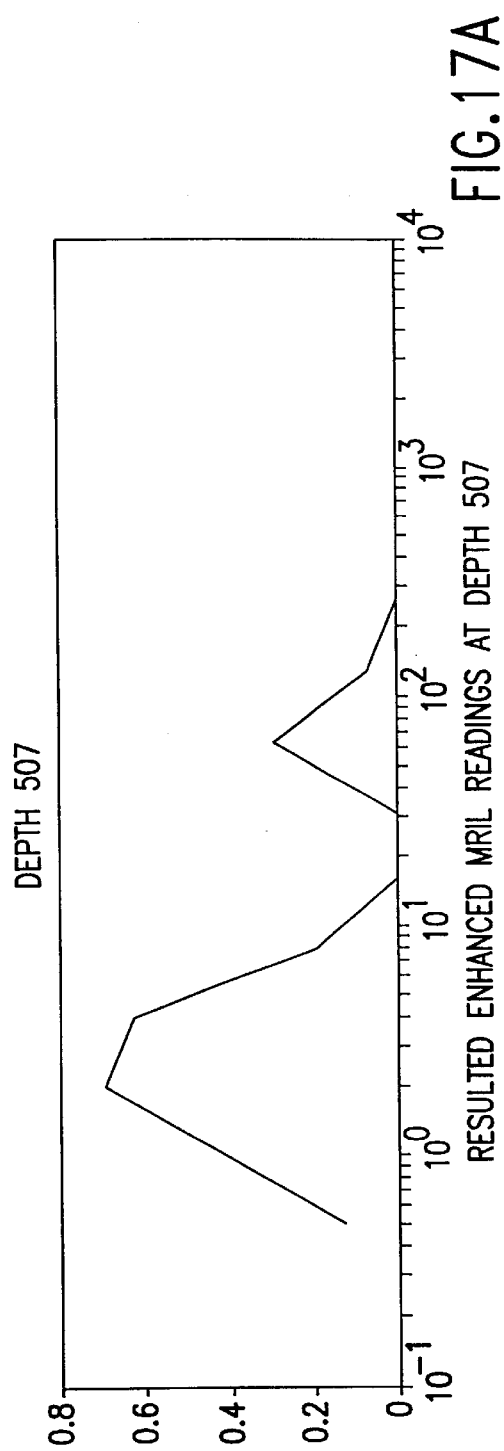
Figure 17B:
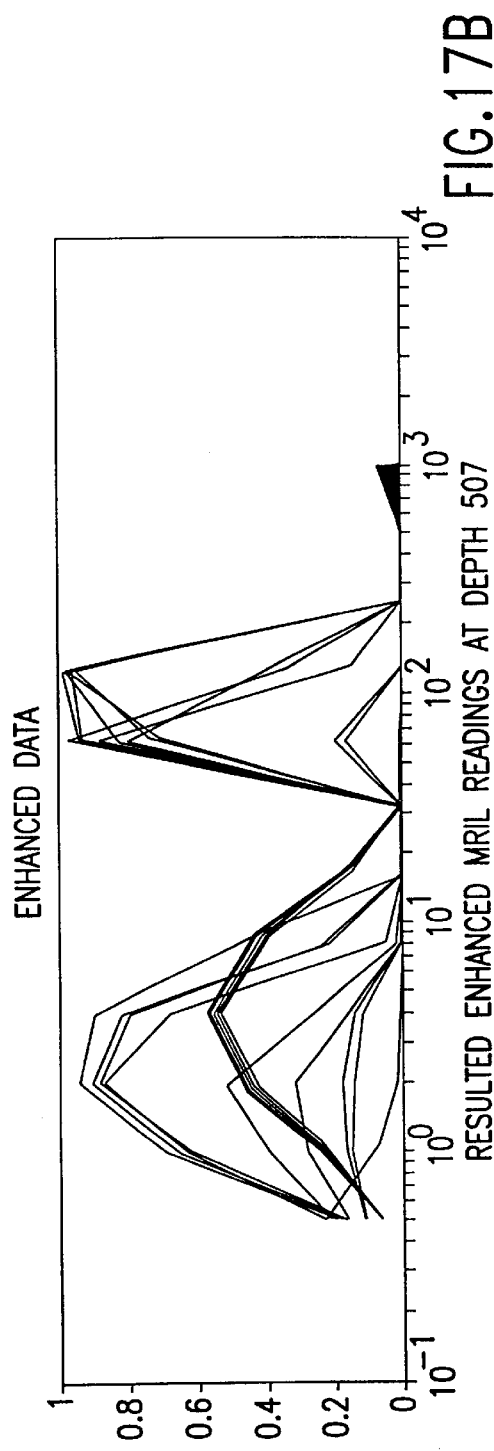
Figure 19A:
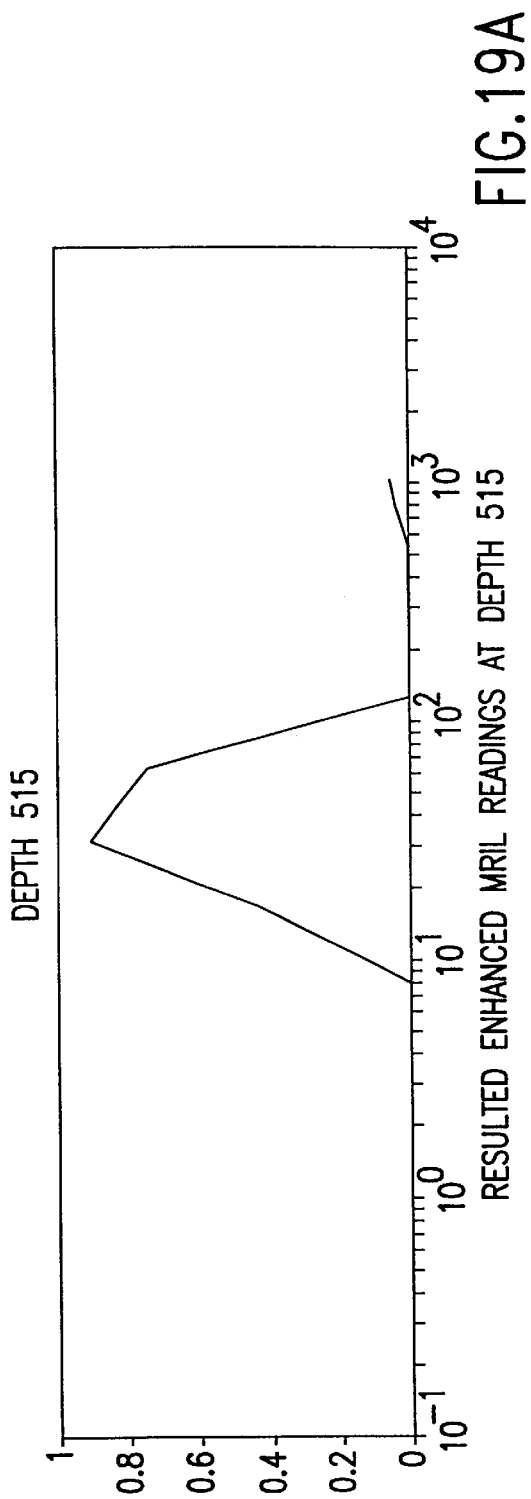
Figure 19B:
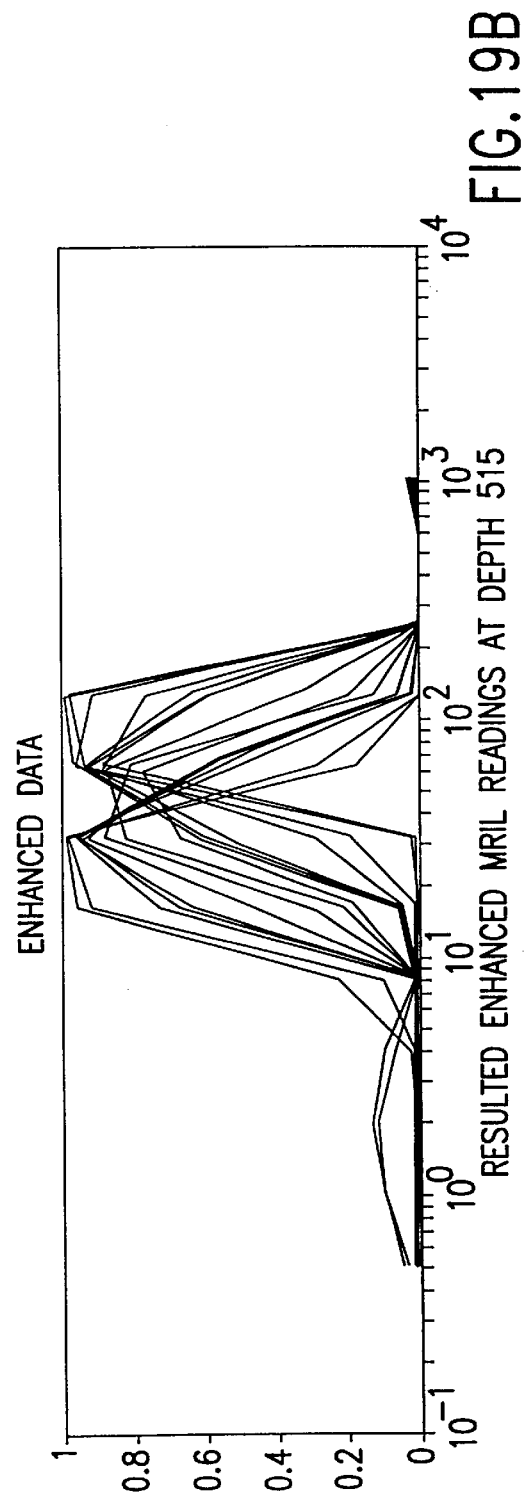

In the second stage, the data was chosen 4 ft apart to correspond to the MRIL resolution. The input data (EMI & PE) were averaged over 4 ft and used as inputs. The size of the training set was 7. The resulted mean square error of the training set was 1.4659e-04. The results are shown in FIG. 14. Finally, the ¼ ft data was input to the converged network. The results were the MRIL enhanced readings. In order to calculate the accuracy of the results, the enhanced readings were averaged over 4 ft and compared to the training outputs. The mean square error was 0.0082. The results are shown in FIG. 15. For further insight into the resulted enhanced logs, FIGS. 16, 17, 18 and 19 show the individual results at specific depths.

TABLE 2

|  | Mean Square Error | | | |
|---|---|---|---|---|
|  | Stage 1 | | Stage 2 | |
|  | Training Set | Testing Set | Training Set | Enhanced Results |
| Mean Square Error | 0.0021 | 0.0033 | 1.4659e-04 | 0.0082 |

It should be noted that generally, the specifics of the training process are largely irrelevant for the operation of the system. In fact, all that is required is that the neural network be able to be trained and retrained, if necessary. As known in the art, a large number of techniques has been proposed in the past for training feedforward neural networks. Most currently used techniques are variations of the well-known error backpropagation method. The specifics of the method need not be considered in detail here. For further reference and more detail the reader is directed to the discussion provided by Rumelhardt et al. in "Parallel Distributed Processing: Explorations in the Microstructure of Cognition," vol. 1 and 2, Cambridge: MIT Press (1986), and "Explorations in Parallel Distributed Processing, A Handbook of Models, Programs, and Exercises," which are incorporated herein by reference for background.

Figure 20:
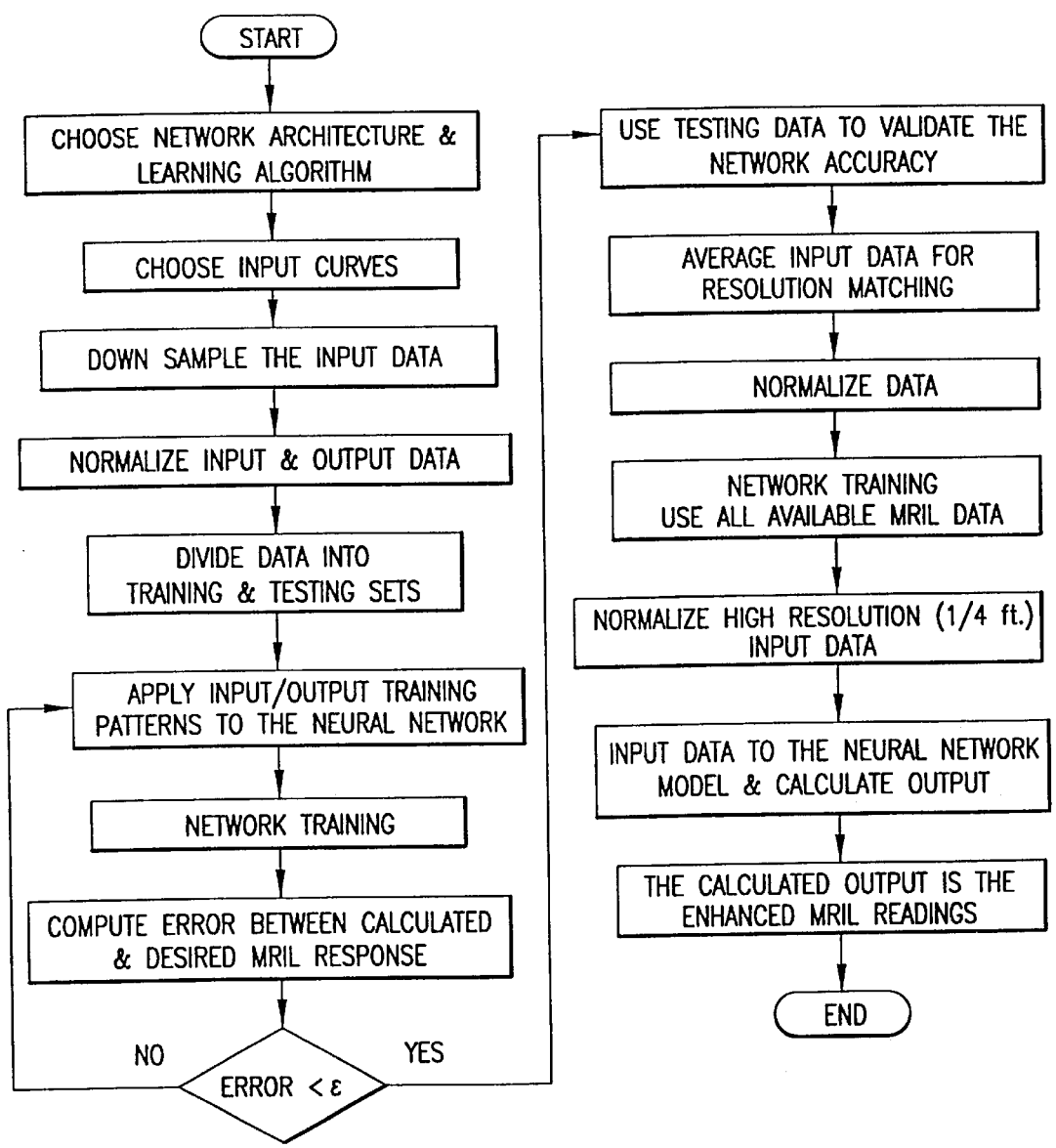
FIG. 20 is a block diagram illustrating the steps in a preferred embodiment of the neural network resolution enhancement approach in accordance with the present invention.

A more detailed illustration of the method of the present invention using neural networks is illustrated in FIG. 20. It should be noted again that while the figure refers to the MRIL tool, the practical application of the approach is not so limited, and can be applied to the log data of any number of tools used for petrophysical exploration.

While the invention has been described with reference to the preferred embodiments, it will be appreciated by those of ordinary skill in the art that modifications can be made to the structure and form of the invention without departing from its spirit and scope which is defined in the following claims.

What is claimed is:

1. A method for determining petrophysical properties of layered geologic formations, comprising:

classifying layers in a portion of a geologic formation into two or more discrete layer types;

providing numerical data about layer compositions in said portion of the formation using one or more log measurements;

inputting provided numerical data to a neural network trained to detect patterns of classified layers; and enhancing the resolution of at least one log measurement using the output of the trained neural network;

wherein one of said log measurements is performed using a high-resolution tool, the high-resolution tool being a Photoelectric (Pe) Tool.

2. The method of claim 1, wherein the step of providing numerical data uses at least two log measurements, and the enhanced-resolution log measurement is obtained from a log recording multiple values at a given depth in the formation.

3. The method of claim 2, wherein the enhanced-resolution log measurement is a nuclear magnetic resonance (NMR) log measurement.

4. The method of claim 1, wherein said two or more discrete layer types comprise sand and shale layer types.

5. The method of claim 1 further comprising the step of determining petrophysical properties of layers in said portion of the formation from the enhanced resolution log measurement.

6. The method of claim 5, wherein petrophysical properties of layers are in the group comprising: permeability, bulk volume irreducible (BVI) and free fluid index (FFI).

7. The method of claim 1, wherein a second high-resolution log measurement is used, the second high-resolution log measurement being obtained from an Electric Micro Imaging (EMI) tool.

8. The method of claim 7, wherein the enhanced-resolution log measurement is obtained from a log recording multiple values at a given depth in the formation.

9. A method for determining petrophysical properties of layered geologic formations, comprising:
  classifying layers in a portion of a geologic formation into two or more discrete layer types;
  providing numerical data about layer compositions in said portion of the formation using one or more log measurements;
  inputting provided numerical data to a neural network trained to detect patterns of classified layers; and
  enhancing the resolution of at least one log measurement using the output of the trained neural network;
  determining petrophysical properties of layers in said portion of the formation from the enhanced resolution log measurement, wherein petrophysical properties of the layers are in the group comprising: permeability, bulk volume irreducible (BVI) and free fluid index (FFI).

10. The method of claim 9, wherein the step of providing numerical data uses at least two log measurements, and the enhanced-resolution log measurement is obtained from a log recording multiple values at a given depth in the formation.

11. The method of claim 9, wherein the step of providing numerical data uses a first and a second log measurements, and the first log measurement has resolution high compared with the resolution of the second log measurement.

12. The method of claim 11, wherein the first log measurement is obtained from a log recording a single value at a given depth in the formation, and a second log measurement is obtained from a log recording multiple values at a given depth in the formation.

13. The method of claim 9, wherein the enhanced-resolution log measurement is a nuclear magnetic resonance (NMR) log measurement.

14. The method of claim 11, wherein the first log measurement is obtained from an Electric Micro Imaging (EMI) tool.

15. The method of claim 11, wherein the first log measurement is obtained from a Photoelectric (Pe) tool.

16. A method for determining petrophysical properties of layered geologic formations, comprising:
  classifying layers in a portion of a geologic formation into two or more discrete layer types;
  providing numerical data about layer compositions in said portion of the formation using one or more log measurements;
  inputting provided numerical data to a neural network trained to detect patterns of classified layers; and
  enhancing the resolution of at least one log measurement using the output of the trained neural network, wherein layers in the formation are thin compared with the vertical resolution of a tool used to obtain NMR echo train data.

17. The method of claim 16 further comprising the step of determining petrophysical properties of layers in said portion of the formation from the enhanced resolution log measurement.

18. The method of claim 16, wherein petrophysical properties of layers are in the group comprising: permeability, bulk volume irreducible (BVI) and free fluid index (FFI).

19. The method of claim 16, wherein the step of providing numerical data uses at least two log measurements, and the enhanced-resolution log measurement is obtained from a log recording multiple values at a given depth in the formation.

20. The method of claim 16, wherein the step of providing numerical data uses a first and a second log measurements, and the first log measurement has resolution high compared with the resolution of the second log measurement.

21. The method of claim 20, wherein the first log measurement is obtained from an Electric Micro Imaging (EMI), a Photoelectric (Pe) tool or a combination thereof.

22. The method of claim 21, wherein the enhanced-resolution log measurement is a NMR log measurement.

23. The method of claim 16, wherein said two or more discrete layer types comprise sand and shale layer types.

24. The method of claim 20 further comprising the step of training the neural network.

25. A system for interpretation of geological formations, comprising a specially programmed computer having:
  a first memory for storing one or more actual time-dependent measurement logs of a geological formation;
  a second memory for storing at least one measurement model based on a formation description, said formation description comprising two or more layer compositions;
  a neural network trainable to recognize patterns of layer compositions;
  a processor for generating enhanced lithology-specific measurement log data representations corresponding to said two or more geological layer types from an actual time-dependent measurement log of a geological formation processed using the neural network; and
  display for communicating to a user the enhanced lithology-specific measurement log data representations, wherein said formation description is provided by the output of a Photoelectric (Pe) tool.

26. The system of claim 25 further comprising a third memory for storing one or more measurement logs of a geological formation obtained from tool(s) recording single values at a given depth in the formation.

27. The system of claim 25, wherein said formation description is also provided by the output of an EMI tool.

28. The system of claim 25, wherein the neural network is a feedforward neural network.

29. The system of claim 28, wherein the neural network has a three-layer network architecture.

30. The method of claim 24, wherein the step of training the neural network comprises averaging high-resolution data from the first log measurement to match the resolution of the NMR logging tool.

* * * * *